US007939251B2

(12) United States Patent
Holcomb et al.

(10) Patent No.: US 7,939,251 B2
(45) Date of Patent: May 10, 2011

(54) SENP1 AS A MARKER FOR CANCER

(75) Inventors: Cherie Holcomb, Oakland, CA (US);
Russell Higuchi, Alameda, CA (US)

(73) Assignee: Roche Molecular Systems, Inc.,
Pleasanton, CA (US)

( * ) Notice: Subject to any disclaimer, the term of this patent is extended or adjusted under 35 U.S.C. 154(b) by 6 days.

(21) Appl. No.: 11/120,544

(22) Filed: May 2, 2005

(65) Prior Publication Data

US 2006/0014171 A1    Jan. 19, 2006

Related U.S. Application Data

(60) Provisional application No. 60/569,220, filed on May 6, 2004, provisional application No. 60/599,318, filed on Aug. 5, 2004.

(51) Int. Cl.
*C12Q 1/68* (2006.01)
(52) U.S. Cl. ............................................. 435/6
(58) Field of Classification Search ........................ None
See application file for complete search history.

(56) References Cited

U.S. PATENT DOCUMENTS

| 5,487,972 | A | * | 1/1996 | Gelfand et al. | 435/6 |
| 5,837,453 | A |  | 11/1998 | Harley et al. |  |
| 5,846,723 | A | * | 12/1998 | Kim et al. | 435/6 |
| 6,551,774 | B1 |  | 4/2003 | West et al. |  |
| 6,582,904 | B2 |  | 6/2003 | Dahm |  |
| 6,596,527 | B1 | * | 7/2003 | Yeh et al. | 435/226 |
| 6,607,898 | B1 |  | 8/2003 | Kopreski et al. |  |
| 2003/0045491 | A1 |  | 3/2003 | Reinhard et al. |  |
| 2003/0170631 | A1 |  | 9/2003 | Houghton et al. |  |
| 2004/0029114 | A1 |  | 2/2004 | Mack et al. | 435/6 |
| 2004/0076955 | A1 | * | 4/2004 | Mack et al. | 435/6 |
| 2006/0057623 | A1 |  | 3/2006 | Yeh |  |

FOREIGN PATENT DOCUMENTS

| EP | 1 108 789 A2 | 6/2001 |
| EP | 09100310 | 9/2009 |
| JP | 2003-506032 A | 2/2003 |
| WO | WO 00/79267 A2 | 12/2000 |
| WO | WO 01/09292 * | 2/2001 |
| WO | WO 01/09292 A2 * | 2/2001 |
| WO | WO 01/09292 A3 | 2/2001 |
| WO | WO 01/22920 A2 | 4/2001 |
| WO | WO 2004/031411 A3 | 4/2004 |
| WO | WO 2004/031412 A2 | 4/2004 |
| WO | WO 2004/031412 A3 | 4/2004 |
| WO | WO 2004/031414 A3 | 4/2004 |
| WO | WO 2004/048938 A3 | 6/2004 |
| WO | 2005108603 A1 | 11/2005 |

OTHER PUBLICATIONS

Konety et al (Journal of Urology, Feb. 2001, 165:600-611).*
GenBank Accession No. NM_014554 (NCBI Sequence Viewer, p. 1-6).*
GenBank Accession No. NM_014554 (NCBI Sequence Viewer, printed Jun. 3, 2008, p. 1-6).*
Stein et al (Cancer Research, Apr. 2004, 64:2805-2816).*
Freshney (Culture of Animal Cells, A Manual of Basic Technique, Alan R. Liss, Inc., 1983, New York, 4 pages).*
Dermer (Bio/Technology, 1994, 12:320).*
Shariat et al (Reviews in Urology, 2008, 10:120-135).*
Weikert et al (Int J Cancer, 2005, 117:274-280).*
Hanke et al (Clinical Chemistry, 2007, 53:2070-2077).*
Dey, Pranab; "Urinary markers of bladder carcinoma"; 2004, *Clinica Chimica Acta*, vol. 340, pp. 57-65.
Gong, Limin et al.; "Differential Regulation of Sentrinized Proteins by a Novel Sentrin-Specific Protease"; 2000, *The Journal of Biological Chemistry*, vol. 275, No. 5, pp. 3355-3359.
Reesink-Peters, N. et al.; "Detection of telomerase, its components, and human papillomavirus in cervical scrapings as a tool for triage in women with cervical dysplasia"; 2003, *J. Clin. Pathol.* vol. 56, pp. 31-35.
Villalva, Claire et al.; "Isolation of differentially expressed genes in NPM-ALK-positive anaplastic large cell lymphoma"; 2002, *British Journal of Haematology* vol. 118, pp. 791-798.
Wege, Henning et al.; "SYBR Green real-time telomeric repeat amplification protocol for the rapid quantification of telomerase"; 2003, *Nucleic Acids Research*, vol. 31, No. 2 e3, 7 pages.
Wright, Woodring E. et al.; "Modifications of a telomeric repeat amplification protocol (TRAP) result in increased reliability, linearity and sensitivity"; 1995, *Nucleic Acids Research*, vol. 23, No. 18, pp. 3794-3795.
Search Report, PCT/EP2005/004839, Apr. 5, 2005.
Botezatu, Irina et al.; "Genetic Analysis of DNA Excreted in Urine: A New Approach for Detecting Specific Genomic DNA Sequences from Cells Dying in an Organism"; 2000, *Clinical Chemistry*, vol. 46, No. 8, pp. 1078-1084.
Bryzgunova, Olga E. et al.; "Isolation and Comparative Study of Cell-Free Nucleic Acids from Human Urine"; 2006, *Ann. N.Y. Acad. Sci.*, vol. 1075, pp. 334-340.
Cheng, Jinke et al.; "SENP1 Enhances Androgen Receptor-Dependent Transcription through Desumoylation of Histone Deacetylase 1"; 2004, *Molecular and Cellular Biology*, vol. 24, No. 13, pp. 6021-6028.
Dolicanin, Zana et al.; "Biomarkers for Detection, Treatment Decision and Prognosis of the Urinary Bladder Cancer"; 2007, *Medicine and Biology*, vol. 14, No. 1, pp. 1-5.
Giannopoulos, Aris et al.; "Comparative Evaluation of the BTAstat Test, NMP22, and Voided Urine Cytology in the Detection of Primary and Recurrent Bladder Tumors"; 2000, *Urology*, vol. 55, No. 6, pp. 871-875.
Landman, Jaime et al.; "Sensitivity and Specificity of NMP-22, Telomerase, and BTA in the Detection of Human Bladder Cancer"; 1998, *Urology*, vol. 52, No. 3, pp. 398-402.
Lo, Dennis Y.M.; "Molecular Testing of Urine: Catching DNA on the Way Out"; 2000, *Clinical Chemistry*, vol. 46, No. 8, pp. 1039-1040.
Hanke, Merle et al.; "Detailed Technocal Analysis of Urine RNA-Based Tumor Diagnostics Reveals ETS2/Urokinase Plasminogen Activator to Be a Novel Marker for Bladder Cancer"; 2007, *Clinical Chemistry*, vol. 53, No. 12, pp. 2070-2077.

(Continued)

*Primary Examiner* — Laura B Goddard
(74) *Attorney, Agent, or Firm* — Kilpatrick Townsend & Stockton LLP

(57) ABSTRACT

The present invention provides methods of detecting cancer cells by detecting the quantity of SENP1 and/or telomerase in a sample.

10 Claims, 11 Drawing Sheets

OTHER PUBLICATIONS

Hewitt, Stephen M. et al.; "Discovery of Protein Biomarkers for Renal Diseases"; 2004, *J Am Soc Nephrol.*, vol. 15, pp. 1677-1689.

Holyoake, Andrew et al.; "Development of a Multiplex RNA Urine Test for the Detection and Stratification of Transitional Cell Carcinoma of the Bladder"; 2008, *Clinical Cancer Research*, vol. 14, pp. 742-749.

Ito, Hideaki et al.; "Detection of Human Telomerase Reverse Transcriptase Messenger RNA in Voided Urine Samples as a Useful Diagnostic Tool for Bladder Cancer"; 1998, *Clinical Cancer Research*, vol. 4, pp. 2807-2810.

Kavaler, Elizabeth et al.; "Detecting Human Bladder Carcinoma Cells in Voided Urine Samples by Assaying for the Presence of Telomerase Activity"; 1998, *Cancer*, vol. 82, No. 4, pp. 708-714.

Kim, Nam W. et al.; "Specific Association of Human Telomerase Activity with Immortal Cells and Cancer"; 1994, *Science*, vol. 266, pp. 2011-2015.

Muller, Markus et al.; "Comparison of Human Telomerase RNA and Telomerase Activity in Urine for Diagnosis of Bladder Cancer"; 1998, *Clinical Cancer Research*, vol. 4, pp. 1949-1954.

Muller, Markus et al.; "Telomerase: Its clinical relevance in the diagnosis of bladder cancer"; 2002, *Oncogene*, vol. 21, pp. 650-655.

Ramakumar, Sanjay et al.; "Comparison of Screening Methods in the Detection of Bladder Cancer"; 1999, *The Journal of Urology*, vol. 161, pp. 388-394.

Tinzl, Martina et al.; "$DD3^{PCA3}$ RNA Analysis in Urine—A New Perspective for Detecting Prostate Cancer"; 2004, *European Urology*, vol. 46, pp. 182-187.

Weiner, H.G. et al.; "Can Urine Bound Diagnostic Tests Replace Cystoscopy in the Management of Bladder Cancer"; 1998, *The Journal of Urology*, vol. 59, pp. 1876-1880.

Shay, J. W. et al.; "A Survey of Telomerase Activity in Human Cancer"; 1997, *European Journal of Cancer*, vol. 33, No. 5, pp. 787-791.

Yokota, Jun et al.; 1998, *Illustrated Medicine and Science Series, Solving the Mechanisms of Canceration, First Edition*, pp. 90-95.

Adachi, Hiroyuki et al.; "Niban gene is commonly expressed in the renal tumors: a new candidate marker for renal carcinogenesis"; 2004, *Oncogene*, vol. 23, pp. 3495-3500.

European Search Report dated Oct. 22, 2010, issued in related European Patent Application No. 10175616.1.

* cited by examiner

SEQUENCE LISTING

<160> NUMBER OF SEQ ID NOS: 20

<210> SEQ ID NO 1
<211> LENGTH: 1932
<212> TYPE: DNA
<213> ORGANISM: Homo sapiens
<220> FEATURE:
<223> OTHER INFORMATION: sentrin/SUMO-specific protease 1 (SENP1)

<400> SEQUENCE: 1

```
atggatgata ttgctgatag gatgaggatg gatgctggag aagtgacttt agtgaaccac      60
aactccgtat tcaaaaccca cctcctgcca caaacaggtt ttccagagga ccagctttcg     120
ctttctgacc agcagatttt atcttccagg caaggacatt tggaccgatc ttttacatgt     180
tccacaagaa gtgcagctta taatccaagc tattactcag ataatccttc ctcagacagt     240
tttcttggct caggcgattt aagaaccttt ggccagagtg caaatggcca atggagaaat     300
tctaccccat cgtcaagctc atctttacaa aaatcaagaa acagccgaag tctttacctc     360
```

-continued

```
gaaacccgaa agacctcaag tggattatca aacagttttg cgggaaagtc aaaccatcac    420
tgccatgtat ctgcatatga aaatcttttt cctattaaac ctgttccaag tccatcttgg    480
agtggttcat gtcgtcgaag tcttttgagc cccaagaaaa ctcagaggcg acatgttagt    540
acagcagaag agacagttca agaagaagaa agagagattt acagacagct gctacagatg    600
gtcacaggga acagtttac tatagccaaa cccaccacac attttccttt acacctgtct     660
cgatgtctta gttccagtaa aaatactttg aaagactcac tgtttaaaaa tggaaactct    720
tgtgcatctc agatcattgg ctctgatact tcatcatctg atctgccag cattttaact     780
aaccaggaac agctgtccca cagtgtatat tccctatctt cttataccc agatgttgca     840
tttggatcca agattctgg tactcttcat catccccatc atcaccactc tgttccacat     900
cagccagata acttagcagc ttcaaataca caatctgaag gatcagactc tgtgatttta    960
ctgaaagtga agattccca gactccaact cccagttcta ctttcttcca ggcagagctg    1020
tggatcaaag aattaactag tgtttatgat tctcgagcac gagaaagatt gcgccagatt    1080
gaagaacaga aggcattggc cttacagctt caaaaccaga gattgcagga gcgggaacat    1140
tcagtacatg attcagtaga actacatctt cgtgtacctc ttgaaaagga gattcctgtt    1200
actgttgtcc aagaaacaca aaaaaaaggt cataaattaa ctgatagtga agatgaattt    1260
cctgaaatta cagaggaaat ggagaaagaa ataaagaatg tatttcgtaa tgggaatcag    1320
gatgaagttc tcagtgaagc atttcgcctg accattacac gcaaagatat tcaaactcta    1380
aaccatctga attggctcaa tgatgagatc atcaatttct acatgaatat gctgatggag    1440
cgaagtaaag agaagggctt gccaagtgtg catgcattta ataccttttt cttcactaaa    1500
ttaaaaacgg ctggttatca ggcagtgaaa cgttggacaa agaaagtaga tgtattttct    1560
gttgacattc ttttggtgcc cattcacctg ggagtacact ggtgtctagc tgttgtggac    1620
tttagaaaga gaatattac ctattacgac tccatgggtg gataaacaa tgaagcctgc     1680
agaatactct tgcaatacct aaagcaagaa agcattgaca agaaaggaa agagtttgac    1740
accaatggct ggcagctttt cagcaagaaa agccagattc ctcagcagat gaatggaagt    1800
gactgtggga tgtttgcctg caaatatgct gactgtatta ccaaagacag accaatcaac    1860
ttcacacagc aacacatgcc atacttccgg aagcggatgg tctgggagat cctccaccga    1920
aaactcttgt ga                                                         1932
```

<210> SEQ ID NO 2
<211> LENGTH: 643
<212> TYPE: PRT
<213> ORGANISM: Homo sapiens
<220> FEATURE:
<223> OTHER INFORMATION: sentrin/SUMO-specific protease 1 (SENP1)

<400> SEQUENCE: 2

```
Met Asp Asp Ile Ala Asp Arg Met Arg Met Asp Ala Gly Glu Val Thr
  1               5                  10                  15

Leu Val Asn His Asn Ser Val Phe Lys Thr His Leu Leu Pro Gln Thr
                 20                  25                  30

Gly Phe Pro Glu Asp Gln Leu Ser Leu Ser Asp Gln Gln Ile Leu Ser
             35                  40                  45

Ser Arg Gln Gly His Leu Asp Arg Ser Phe Thr Cys Ser Thr Arg Ser
         50                  55                  60

Ala Ala Tyr Asn Pro Ser Tyr Tyr Ser Asp Asn Pro Ser Ser Asp Ser
 65                  70                  75                  80
```

-continued

```
Phe Leu Gly Ser Gly Asp Leu Arg Thr Phe Gly Gln Ser Ala Asn Gly
                85                  90                  95

Gln Trp Arg Asn Ser Thr Pro Ser Ser Ser Ser Leu Gln Lys Ser
            100                 105                 110

Arg Asn Ser Arg Ser Leu Tyr Leu Glu Thr Arg Lys Thr Ser Ser Gly
            115                 120                 125

Leu Ser Asn Ser Phe Ala Gly Lys Ser Asn His His Cys His Val Ser
    130                 135                 140

Ala Tyr Glu Lys Ser Phe Pro Ile Lys Pro Val Pro Ser Pro Ser Trp
145                 150                 155                 160

Ser Gly Ser Cys Arg Arg Ser Leu Leu Ser Pro Lys Lys Thr Gln Arg
                165                 170                 175

Arg His Val Ser Thr Ala Glu Glu Thr Val Gln Glu Glu Glu Arg Glu
            180                 185                 190

Ile Tyr Arg Gln Leu Leu Gln Met Val Thr Gly Lys Gln Phe Thr Ile
            195                 200                 205

Ala Lys Pro Thr Thr His Phe Pro Leu His Leu Ser Arg Cys Leu Ser
    210                 215                 220

Ser Ser Lys Asn Thr Leu Lys Asp Ser Leu Phe Lys Asn Gly Asn Ser
225                 230                 235                 240

Cys Ala Ser Gln Ile Ile Gly Ser Asp Thr Ser Ser Ser Gly Ser Ala
                245                 250                 255

Ser Ile Leu Thr Asn Gln Glu Gln Leu Ser His Ser Val Tyr Ser Leu
            260                 265                 270

Ser Ser Tyr Thr Pro Asp Val Ala Phe Gly Ser Lys Asp Ser Gly Thr
            275                 280                 285

Leu His His Pro His His His Ser Val Pro His Gln Pro Asp Asn
    290                 295                 300

Leu Ala Ala Ser Asn Thr Gln Ser Glu Gly Ser Asp Ser Val Ile Leu
305                 310                 315                 320

Leu Lys Val Lys Asp Ser Gln Thr Pro Thr Pro Ser Ser Thr Phe Phe
                325                 330                 335

Gln Ala Glu Leu Trp Ile Lys Glu Leu Thr Ser Val Tyr Asp Ser Arg
            340                 345                 350

Ala Arg Glu Arg Leu Arg Gln Ile Glu Glu Gln Lys Ala Leu Ala Leu
            355                 360                 365

Gln Leu Gln Asn Gln Arg Leu Gln Glu Arg Glu His Ser Val His Asp
    370                 375                 380

Ser Val Glu Leu His Leu Arg Val Pro Leu Glu Lys Glu Ile Pro Val
385                 390                 395                 400

Thr Val Val Gln Glu Thr Gln Lys Lys Gly His Lys Leu Thr Asp Ser
                405                 410                 415

Glu Asp Glu Phe Pro Glu Ile Thr Glu Glu Met Glu Lys Glu Ile Lys
            420                 425                 430

Asn Val Phe Arg Asn Gly Asn Gln Asp Glu Val Leu Ser Glu Ala Phe
    435                 440                 445

Arg Leu Thr Ile Thr Arg Lys Asp Ile Gln Thr Leu Asn His Leu Asn
    450                 455                 460

Trp Leu Asn Asp Glu Ile Ile Asn Phe Tyr Met Asn Met Leu Met Glu
465                 470                 475                 480

Arg Ser Lys Glu Lys Gly Leu Pro Ser Val His Ala Phe Asn Thr Phe
                485                 490                 495

Phe Phe Thr Lys Leu Lys Thr Ala Gly Tyr Gln Ala Val Lys Arg Trp
            500                 505                 510
```

```
Thr Lys Lys Val Asp Val Phe Ser Val Asp Ile Leu Leu Val Pro Ile
        515                 520                 525

His Leu Gly Val His Trp Cys Leu Ala Val Val Asp Phe Arg Lys Lys
        530                 535                 540

Asn Ile Thr Tyr Tyr Asp Ser Met Gly Gly Ile Asn Asn Glu Ala Cys
545                 550                 555                 560

Arg Ile Leu Leu Gln Tyr Leu Lys Gln Glu Ser Ile Asp Lys Lys Arg
                565                 570                 575

Lys Glu Phe Asp Thr Asn Gly Trp Gln Leu Phe Ser Lys Lys Ser Gln
                580                 585                 590

Ile Pro Gln Gln Met Asn Gly Ser Asp Cys Gly Met Phe Ala Cys Lys
                595                 600                 605

Tyr Ala Asp Cys Ile Thr Lys Asp Arg Pro Ile Asn Phe Thr Gln Gln
        610                 615                 620

His Met Pro Tyr Phe Arg Lys Arg Met Val Trp Glu Ile Leu His Arg
625                 630                 635                 640

Lys Leu Leu

<210> SEQ ID NO 3
<211> LENGTH: 1132
<212> TYPE: PRT
<213> ORGANISM: Homo sapiens
<220> FEATURE:
<223> OTHER INFORMATION: human telomerase reverse transcriptase (TERT)

<400> SEQUENCE: 3

Met Pro Arg Ala Pro Arg Cys Arg Ala Val Arg Ser Leu Leu Arg Ser
1                   5                  10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
        210                 215                 220

Gly Gly Ser Ala Ser Arg Ser Leu Pro Leu Pro Lys Arg Pro Arg Arg
225                 230                 235                 240
```

```
Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670
```

-continued

Pro Gly Leu Leu Gly Ala Ser Val Leu Gly Leu Asp Ile His Arg
675                 680                 685

Ala Trp Arg Thr Phe Val Leu Arg Val Arg Ala Gln Asp Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                    725                 730                 735

Asn Thr Tyr Cys Val Arg Arg Tyr Ala Val Val Gln Lys Ala Ala His
                740                 745                 750

Gly His Val Arg Lys Ala Phe Lys Ser His Val Ser Thr Leu Thr Asp
755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                    805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
                835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                    885                 890                 895

Val Val Asn Leu Arg Lys Thr Val Val Asn Phe Pro Val Glu Asp Glu
                    900                 905                 910

Ala Leu Gly Gly Thr Ala Phe Val Gln Met Pro Ala His Gly Leu Phe
            915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                    965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu Leu Leu Gln
                995                 1000                1005

Ala Tyr Arg Phe His Ala Cys Val Leu Gln Leu Pro Phe His Gln Gln
    1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
            1045                1050                1055

Gly Ala Lys Gly Ala Ala Gly Pro Leu Pro Ser Glu Ala Val Gln Trp
            1060                1065                1070

Leu Cys His Gln Ala Phe Leu Leu Lys Leu Thr Arg His Arg Val Thr
    1075                1080                1085

Tyr Val Pro Leu Leu Gly Ser Leu Arg Thr Ala Gln Thr Gln Leu Ser
    1090                1095                1100

```
Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
            1125                1130
```

<210> SEQ ID NO 4
<211> LENGTH: 4015
<212> TYPE: DNA
<213> ORGANISM: Homo sapiens
<220> FEATURE:
<223> OTHER INFORMATION: human telomerase reverse transcriptase (TERT)

<400> SEQUENCE: 4

```
gcagcgctgc gtcctgctgc gcacgtggga agccctggcc ccggccaccc ccgcgatgcc     60
gcgcgctccc cgctgccgag ccgtgcgctc cctgctgcgc agccactacc gcgaggtgct    120
gccgctggcc acgttcgtgc ggcgcctggg ccccagggc tggcggctgg tgcagcgcgg    180
ggacccggcg gctttccgcg cgctggtggc ccagtgcctg gtgtgcgtgc cctgggacgc    240
acggccgccc ccgccgccc cctccttccg ccaggtgtcc tgcctgaagg agctggtggc    300
ccgagtgctg cagaggctgt gcgagcgcgg cgcgaagaac gtgctggcct tcggcttcgc    360
gctgctggac ggggcccgcg ggggcccccc cgaggccttc accaccagcg tgcgcagcta    420
cctgcccaac acggtgaccg acgcactgcg ggggagcggg gcgtggggc tgctgctgcg    480
ccgcgtgggc gacgacgtgc tggttcacct gctggcacgc tgcgcgctct tgtgctggt    540
ggctcccagc tgcgcctacc aggtgtgcgg ccgccgctg taccagctcg gcgctgccac    600
tcaggcccgg ccccgccac acgctagtgg accccgaagg cgtctgggat gcgaacgggc    660
ctggaaccat agcgtcaggg aggccggggt cccctgggc ctgccagccc cgggtgcgag    720
gaggcgcggg ggcagtgcca gccgaagtct gccgttgccc aagaggccca ggcgtggcgc    780
tgccccctgag ccggagcgga cgcccgttgg gcagggtcc tgggcccacc cgggcaggac    840
gcgtggaccg agtgaccgtg gtttctgtgt ggtgtcacct gccagacccg ccgaagaagc    900
cacctctttg gagggtgcgc tctctggcac gcgccactcc cacccatccg tgggccgcca    960
gcaccacgcg ggccccccat ccacatcgcg gccaccacgt ccctgggaca cgccttgtcc   1020
cccggtgtac gccgagacca agcacttcct ctactcctca ggcgacaagg agcagctgcg   1080
gccctccttc ctactcagct ctctgaggcc cagcctgact ggcgctcgga ggctcgtgga   1140
gaccatcttt ctgggttcca ggccctggat gccagggact ccccgcaggt tgccccgcct   1200
gccccagcgc tactgcaaa tgcggcccct gtttctggag ctgcttggga accacgcgca   1260
gtgcccctac ggggtgctcc tcaagacgca ctgcccgctg cgagctgcgg tcaccccagc   1320
agccggtgtc tgtgcccggg agaagcccca gggctctgtg gcggccccg aggaggagga   1380
cacagacccc cgtcgcctgg tgcagctgct ccgccagcac agcagcccct ggcaggtgta   1440
cggcttcgtg cgggcctgcc tgcgccggct ggtgccccca ggcctctggg gctccaggca   1500
caacgaacgc gcttcctca ggaacaccaa gaagttcatc tccctgggga gcatgccaa    1560
gctctcgctg caggagctga cgtggaagat gagcgtgcgg gactgcgctt ggctgcgcag   1620
gagcccaggg gttggctgtg ttccggccgc agagcaccgt ctgcgtgagg atcctggc    1680
caagttcctg cactggctga tgagtgtgta cgtcgtcgag ctgctcaggt ctttcttta    1740
tgtcacggag accacgtttc aaaagaacag gctcttttc taccggaaga gtgtctggag   1800
caagttgcaa agcattggaa tcagacagca cttgaagagg gtgcagctgc gggagctgtc   1860
ggaagcagag gtcaggcagc atcgggaagc caggcccgcc ctgctgacgt ccagactccg   1920
```

```
cttcatcccc aagcctgacg ggctgcggcc gattgtgaac atggactacg tcgtgggagc    1980
cagaacgttc cgcagagaaa agagggccga gcgtctcacc tcgagggtga aggcactgtt    2040
cagcgtgctc aactacgagc gggcgcggcg ccccggcctc ctgggcgcct ctgtgctggg    2100
cctggacgat atccacaggg cctggcgcac cttcgtgctg cgtgtgcggg cccaggaccc    2160
gccgcctgag ctgtactttg tcaaggtgga tgtgacgggc gcgtacgaca ccatccccca    2220
ggacaggctc acggaggtca tcgccagcat catcaaaccc cagaacacgt actgcgtgcg    2280
tcggtatgcc gtggtccaga aggccgccca tgggcacgtc cgcaaggcct tcaagagcca    2340
cgtctctacc ttgacagacc tccagccgta catgcgacag ttcgtggctc acctgcagga    2400
gaccagcccg ctgagggatg ccgtcgtcat cgagcagagc tcctccctga atgaggccag    2460
cagtggcctc ttcgacgtct tcctacgctt catgtgccac cacgccgtgc gcatcagggg    2520
caagtcctac gtccagtgcc aggggatccc gcagggctcc atcctctcca cgctgctctg    2580
cagcctgtgc tacggcgaca tggagaacaa gctgtttgcg gggattcggc gggacgggct    2640
gctcctgcgt ttggtggatg atttcttgtt ggtgacacct cacctcaccc acgcgaaaac    2700
cttcctcagg accctggtcc gaggtgtccc tgagtatggc tgcgtggtga acttgcggaa    2760
gacagtggtg aacttccctg tagaagacga ggccctgggt ggcacggctt ttgttcagat    2820
gccggcccac ggcctattcc cctggtgcgg cctgctgctg gatacccgga ccctggaggt    2880
gcagagcgac tactccagct atgcccggac ctccatcaga gccagtctca ccttcaaccg    2940
cggcttcaag gctgggagga acatgcgtcg caaactcttt ggggtcttgc ggctgaagtg    3000
tcacagcctg tttctggatt tgcaggtgaa cagcctccag acggtgtgca ccaacatcta    3060
caagatcctc ctgctgcagg cgtacaggtt tcacgcatgt gtgctgcagc tcccatttca    3120
tcagcaagtt tggaagaacc ccacattttt cctgcgcgtc atctctgaca cggcctccct    3180
ctgctactcc atcctgaaag ccaagaacgc agggatgtcg ctgggggcca agggcgccgc    3240
cggccctctg ccctccgagg ccgtgcagtg gctgtgccac caagcattcc tgctcaagct    3300
gactcgacac cgtgtcacct acgtgccact cctggggtca ctcaggacag cccagacgca    3360
gctgagtcgg aagctcccgg ggacgacgct gactgccctg gaggccgcag ccaacccggc    3420
actgccctca gacttcaaga ccatcctgga ctgatggcca cccgcccaca gccaggccga    3480
gagcagacac cagcagccct gtcacgccgg gctctacgtc ccaggagggg aggggcggcc    3540
cacacccagg cccgcaccgc tgggagtctg aggcctgagt gagtgtttgg ccgaggcctg    3600
catgtccggc tgaaggctga gtgtccggct gaggcctgag cgagtgtcca gccaagggct    3660
gagtgtccag cacacctgcc gtcttcactt ccccacaggc tggcgctcgg ctccacccca    3720
gggccagctt ttcctcacca ggagcccggc ttccactccc cacataggaa tagtccatcc    3780
ccagattcgc cattgttcac ccctcgccct gccctccttt gccttccacc cccaccatcc    3840
aggtggagac cctgagaagg accctgggag ctctgggaat ttggagtgac caaaggtgtg    3900
ccctgtacac aggcgaggac cctgcacctg gatgggggtc cctgtgggtc aaattggggg    3960
gaggtgctgt gggagtaaaa tactgaatat atgagttttt cagttttgaa aaaaa         4015

<210> SEQ ID NO 5
<211> LENGTH: 451
<212> TYPE: DNA
<213> ORGANISM: Homo sapiens
<220> FEATURE:
<223> OTHER INFORMATION: human telomerase RNA component (TERC)
```

-continued

```
<400> SEQUENCE: 5
gggttgcgga gggtgggcct gggaggggtg gtggccattt tttgtctaac cctaactgag        60
aagggcgtag gcgccgtgct tttgctcccc gcgcgctgtt tttctcgctg actttcagcg       120
ggcggaaaag cctcggcctg ccgccttcca ccgttcattc tagagcaaac aaaaaatgtc       180
agctgctggc ccgttcgccc ctcccgggga cctgcggcgg gtcgcctgcc cagcccccga       240
accccgcctg gaggccgcgg tcggcccggg gcttctccgg aggcacccac tgccaccgcg       300
aagagttggg ctctgtcagc cgcgggtctc tcggggcga gggcgaggtt caggcctttc       360
aggccgcagg aagaggaacg gagcgagtcc ccgcgcgcgg cgcgattccc tgagctgtgg       420
gacgtgcacc caggactcgg ctcacacatg c                                      451

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:SENP1
      forward "sense" primer

<400> SEQUENCE: 6
caagaagtgc agcttataat ccaa                                               24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:SENP1
      reverse "antisense" primer

<400> SEQUENCE: 7
gtctttcggg tttcgaggta a                                                  21

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:SENP1 TaqMan
      probe

<400> SEQUENCE: 8
ctcagacagt tttcttggct caggcg                                             26

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:PPP1CA
      forward primer

<400> SEQUENCE: 9
gagcacacca ggtggtagaa                                                    20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:PPP1CA
      reverse primer
```

-continued

```
<400> SEQUENCE: 10
gggcttgagg atctggaaa                                                    19

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:PPP1CA probe

<400> SEQUENCE: 11
gagtttgaca atgctggcgc catgatgagt                                        30

<210> SEQ ID NO 12
<211> LENGTH: 5
<212> TYPE: PRT
<213> ORGANISM: Artificial Sequence
<220> FEATURE:
<223> OTHER INFORMATION: Description of Artificial
      Sequence:substrate/inhibitor specific for SENP1
      protease, SENP1 antagonist

<400> SEQUENCE: 12

Glu Gln Thr Gly Gly
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:nuclear
      localization signal sequence (NLS1)

<400> SEQUENCE: 13

Pro Lys Lys Thr Gln Arg Arg
 1               5

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence:small
      ubiquitin-like modifier (SUMO) protein Sm31
      C-terminal sequence

<400> SEQUENCE: 14

Thr Ile Asp Val Phe Gln Gln Gln Thr Gly Gly Val Pro Glu Ser Ser
 1               5                  10                  15

Leu Ala Gly His Ser Phe
            20

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:small
      ubiquitin-like modifier (SUMO) protein Sm32
      C-terminal sequence

<400> SEQUENCE: 15

Thr Ile Asp Val Phe Gln Gln Gln Thr Gly Gly Val Tyr
 1               5                  10
```

```
<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence:small
      ubiquitin-like modifier (SUMO) protein Sm33
      C-terminal sequence

<400> SEQUENCE: 16

Val Ile Glu Val Tyr Gln Glu Gln Thr Gly Gly His Ser Thr Val
 1               5                  10                  15

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence:small
      ubiquitin-like modifier (SUMO) protein Smt3
      C-terminal sequence

<400> SEQUENCE: 17

Ile Ile Glu Ala His Arg Glu Gln Ile Gly Gly Ala Thr Tyr
 1               5                  10

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence:TERT forward
      primer

<400> SEQUENCE: 18
tgggcacgtc cgca                                                         14

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence:TERT reverse
      primer

<400> SEQUENCE: 19
ggcgtggtgg cacatgaa                                                     18

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence:TERT TaqMan
      probe

<400> SEQUENCE: 20
tcatcgagca gagctcctcc ctgaatgagg                                        30
```

SENP1 AS A MARKER FOR CANCER

CROSS-REFERENCE TO RELATED PATENT APPLICATIONS

The present patent application claims benefit of priority to U.S. Provisional Patent Application Nos. 60/569,220, filed May 6, 2004 and 60/599,318, filed Aug. 5, 2004, each of which is incorporated by reference for all purposes.

BACKGROUND OF THE INVENTION

Most cells in the normal adult human body do not divide. Cancer cells, however, escape growth regulation and divide unrestrained. To do this, they must replicate their chromosomes including the ends of these chromosomes, called telomeres.

Activation of the enzyme, telomerase, which adds telomeric sequence to chromosomal ends (reviewed in Collins, K., *Curr. Opin Cell Biol.* 12:378-383 (2000)) can overcome this senescence. See, Bodnar, A. G., et al., *Science* 279:349-352 (1998); reviewed in De Lange, T., *Science* 279:334-335 (1998)). Cell lines with active telomerase become immortalized. In vivo, previously senescent cells with active telomerase grow into tumors. Telomerase activity has been detected in essentially all major types of cancer (Shay, J. W. and Bacchetti, S., *Eur. J. Cancer,* 33:787-791 (1997); Cong, Y. S., et al., *Microbiol Mol. Biol. Rev.* 66:407-425 (2002)). Hanahan and Weinberg have named the expression of the telomerase catalytic subunit as one of the six key events common to cancer (*Cell* 100: 57-70 (2000)). Expression of the genes coding for telomerase (TERT and TERC) has been proposed as a molecular marker for the diagnosis, monitoring, and prognosis of cancer.

However, not all tumors of a given cancer type contain detectable levels of telomerase activity. See, e.g., Shay, J. W. and Bacchetti, S. *Eur. J. Cancer,* 33:787-791 (1997); Yan, P. et al. *Cancer Res.* 59: 3166-3170 (1999). It is therefore important to identify molecular markers that identify tumors immortalized by a telomerase independent mechanism.

BRIEF SUMMARY OF THE INVENTION

The present invention provides data demonstrating that there is an association of bladder cancer, breast cancer, colon cancer, kidney cancer, lung cancer, ovarian cancer, pancreatic cancer, and small intestine cancer and the quantity of SENP1 expression. Thus, SENP1 provides a useful marker for the detection of bladder cancer, breast cancer, colon cancer, kidney cancer, lung cancer, ovarian cancer, pancreatic cancer, and small intestine cancer cancers.

In some embodiments, the present invention provides methods of detecting SENP1 expression in a biological sample. In some embodiments, the methods comprise determining the quantity of SENP1 in a biological sample from an individual having or suspected of having a cancer selected from the group consisting of breast cancer, colon cancer, kidney cancer, lung cancer, ovarian cancer, pancreatic cancer, and small intestine cancer.

In some embodiments, the methods comprise determining the quantity of SENP1 in a biological sample from an individual; and recording a diagnosis of a cancer selected from the group consisting of breast cancer, colon cancer, kidney cancer, lung cancer, ovarian cancer, pancreatic cancer, and small intestine cancer.

In some embodiments, the methods comprise determining the quantity of SENP1 in a biological sample from an individual, wherein the biological sample is selected from the group consisting of a breast biopsy, a colon biopsy, a kidney biopsy, a lung biopsy, an ovary biopsy, a pancreas biopsy, a small intestine biopsy, a bronchial lavage and a stool. In some embodiments, the methods further comprise recording a diagnosis of a cancer selected from the group consisting of breast cancer, colon cancer, kidney cancer, lung cancer, ovarian cancer, pancreatic cancer, and small intestine cancer.

In some embodiments, the method further comprises obtaining the biological sample from the individual.

In some embodiments, the methods further comprise recording a diagnosis of a cancer selected from the group consisting of breast cancer, colon cancer, kidney cancer, lung cancer, ovarian cancer, pancreatic cancer, and small intestine cancer. In some embodiments, the quantity of SENP1 is detected by detecting a polynucleotide encoding SENP1 in the sample. In some embodiments, the sequence of the polynucleotide is determined. In some embodiments, the detection step comprises amplifying the polynucleotide in an amplification reaction. In some embodiments, the amplification reaction comprises at least two different oligonucleotides comprising a sequence at least 90% identical to at least 10 contiguous nucleotides of SEQ ID NO:1, or a complement thereof, such that during the amplification reaction the oligonucleotides prime amplification of at least a fragment of SEQ ID NO:1. In some embodiments, the amplification reaction is a quantitative amplification reaction. In some embodiments, the amplification product of the amplification reaction is detected in a step comprising hybridizing a detectably-labeled oligonucleotide to the product. In some embodiments, the detectably-labeled oligonucleotide comprises a fluorescent moiety. In some embodiments, the detectably-labeled oligonucleotide comprises a quencher moiety. In some embodiments, the amplification reaction comprises a template-dependent nucleic acid polymerase with 5'-3' exonuclease activity under conditions that allow the polymerase to fragment the detectably-labeled oligonucleotide. In some embodiments, the amplification reaction is a reverse transcriptase polymerase chain reaction (RT-PCR). In some embodiments, the RT-PCR reaction is a quantitative RT-PCR reaction. In some embodiments, the quantity of the polynucleotide is normalized.

In some embodiments, the quantity of SENP1 is determined by detecting a SENP1 polypeptide in the sample. In some embodiments, the polypeptide is detected by contacting the polypeptide with an antibody.

In some embodiments, SENP1 is detected by detecting SENP1 activity.

In some embodiments, the method further comprises determining the quantity of telomerase in the biological sample. In some embodiments, telomerase is detected by detecting telomerase activity. In some embodiments, telomerase activity is detected by detecting elongation of an oligonucleotide comprising two or more repeats of TTAGG.

In some embodiments, telomerase is detected by detecting a component of telomerase in the sample. In some embodiments, the component is human telomerase RNA (TERC). In some embodiments, the component is human telomerase reverse transcriptase protein (TERT). In some embodiments, telomerase is detected by detecting human telomerase reverse transcriptase protein (TERT) mRNA. In some embodiments, the method comprises amplifying a SENP1 polynucleotide and a telomerase polynucleotide in a multiplex amplification reaction. In some embodiments, the telomerase polynucleotide is human telomerase RNA (TERC). In some embodiments, the telomerase polynucleotide is human telomerase reverse transcriptase protein (TERT) mRNA. In some embodiments, the method further comprises comparing the quantity of SENP1 and telomerase in the sample to a SENP1 standard and a telomerase standard, respectively, wherein the SENP1 standard represents SENP1 in non-cancer cells and the telomerase standard represents telomerase quantities in non-cancer cells. In some embodiments, the standards are pre-determined values.

In some embodiments, the individual is a human. In some embodiments, the method further comprises recording a prognosis for cancer treatment and/or survival for the individual. In some embodiments, the method further comprises recording the progression of cancer in the individual.

The present invention also provides methods for identifying an SENP1 antagonist. In some embodiments, the methods comprise contacting a plurality of agents to a cell expressing SENP1, wherein the cell does not express telomerase and the cell expresses a neoplastic phenotype, and selecting an agent that inhibits a neoplastic phenotype, thereby identifying an SENP1 antagonist. In some embodiments, the cell does not express TERT. In some embodiments, the methods further comprise testing the effect of the selected agent on cancer cells selected from the group consisting of breast cancer, colon cancer, kidney cancer, lung cancer, ovarian cancer, pancreatic cancer, and small intestine cancer. In some embodiments, the neoplastic phenotype is neoplastic cell growth. In some embodiments, the neoplastic phenotype is expression of a polypeptide or RNA associated with neoplastic growth. In some embodiments, the cell endogenously expresses SENP1. In some embodiments, the cell comprises an exogenous expression cassette encoding SENP1.

The present invention also provides methods of treating an individual having a cancer. In some embodiments, the methods comprise administering to a human a therapeutic amount of an antagonist of SENP1, wherein the individual has a cancer characterized by increased expression of SENP1 compared to non-cancer cells. In some embodiments, the cancer is selected from the group consisting of bladder cancer, breast cancer, colon cancer, kidney cancer, lung cancer, ovarian cancer, pancreatic cancer, and small intestine cancer. In some embodiments, the antagonist is identified by the steps of: contacting a plurality of agents to a cell expressing SENP1, wherein the cell does not express telomerase and the cell expresses a neoplastic phenotype, and selecting an agent that inhibits a neoplastic phenotype, thereby identifying an SENP1 antagonist.

The present invention also provides inhibitors of SENP1 protease activity. In some embodiments, the inhibitors comprise an amino acid sequence comprising Glu-Gln-Thr-Gly-Gly (SEQ ID NO:12), or a mimetic thereof, wherein the final Gly terminates in an aldehyde. In some embodiments, the inhibitor comprises a nuclear localization signal sequence. In some embodiments, the nuclear localization signal sequence comprises Pro-Lys-Lys-Thr-Gln-Arg-Arg (SEQ ID NO:13).

The present invention also provides for determination of the quantity of SENP1 and telomerase in a biological sample from an individual. In some embodiments, the quantity of SENP1 is detected by detecting a polynucleotide encoding SENP1 in the sample. In some embodiments, the polynucleotide is RNA.

In some embodiments, the sequence of the polynucleotide is determined. In some embodiments, the detection step comprises amplifying the polynucleotide in an amplification reaction. In some embodiments, the amplification reaction comprises at least two different oligonucleotides comprising a sequence at least 90% identical to at least 10 contiguous nucleotides of SEQ ID NO:1, or a complement thereof, such that during the amplification reaction the oligonucleotides prime amplification of at least a fragment of SEQ ID NO:1. In some embodiments, the amplification reaction is a quantitative amplification reaction. In some embodiments, the amplification product of the amplification reaction is detected in a step comprising hybridizing a detectably-labeled oligonucleotide to the product. In some embodiments, the detectably-labeled oligonucleotide comprises a fluorescent moiety. In some embodiments, the detectably-labeled oligonucleotide comprises a quencher moiety. In some embodiments, the amplification reaction comprises a template-dependent nucleic acid polymerase with 5'-3' exonuclease activity under conditions that allow the polymerase to fragment the detectably-labeled oligonucleotide.

In some embodiments, the amplification reaction is a reverse transcriptase polymerase chain reaction (RT-PCR). In some embodiments, the RT-PCR reaction is a quantitative RT-PCR reaction.

In some embodiments, the quantity of the polynucleotide is normalized.

In some embodiments, the quantity of SENP1 is determined by detecting a SENP1 polypeptide in the sample. In some embodiments, the polypeptide is detected by contacting the polypeptide with an antibody In some embodiments, SENP1 is detected by detecting SENP1 activity.

In some embodiments, telomerase is detected by detecting telomerase activity. In some embodiments, telomerase activity is detected by detecting elongation of an oligonucleotide comprising two or more repeats of TTAGG.

In some embodiments, telomerase is detected by detecting a component of telomerase in the sample. In some embodiments, the component is human telomerase RNA (TERC). In some embodiments, the component is human telomerase reverse transcriptase protein (TERT).

In some embodiments, telomerase is detected by detecting human telomerase reverse transcriptase protein (TERT) mRNA.

In some embodiments, the method comprises amplifying a SENP1 polynucleotide and a telomerase polynucleotide in a multiplex amplification reaction. In some embodiments, the telomerase polynucleotide is human telomerase RNA (TERC). In some embodiments, the telomerase polynucleotide is human telomerase reverse transcriptase protein (TERT) mRNA.

In some embodiments, the methods further comprise comparing the quantity of SENP1 and telomerase in the sample to a SENP1 standard and a telomerase standard representing SENP1 and telomerase quantities in non-cancer cells. In some embodiments, the standards are pre-determined values.

In some embodiments, the individual is a human.

In some embodiments, the biological sample comprises a bodily fluid. In some embodiments, the bodily fluid is blood. In some embodiments, the bodily fluid is urine. In some embodiments, the sample is from a tissue biopsy. In some embodiments, the method further comprises obtaining a biological sample from the individual.

In some embodiments, the individual has or is suspected of having cancer. In some embodiments, the cancer is bladder cancer.

In some embodiments, the method further comprises recording a diagnosis of the presence or absence of cancer in the individual. In some embodiments, the method further comprises recording a prognosis for cancer treatment and/or survival for the individual. In some embodiments, the method further comprises recording the progression of cancer in the individual. In some of these embodiments, the cancer is bladder cancer.

The present invention also provides kits for detecting a cancer cell in a biological sample from an individual. In some embodiments, the kit comprises a) at least one oligonucleotide comprising a sequence at least 90% identical to at least 10 contiguous nucleotides of SEQ ID NO:1, or a complement thereof, such that when the oligonucleotide and a polynucleotide comprising SEQ ID NO:1 are submitted to an amplification reaction, the oligonucleotide primes amplification of at least a fragment of SEQ ID NO:1;

b) a detectably-labeled oligonucleotide comprising a sequence at least 90% identical to at least 10 contiguous nucleotides of SEQ ID NO:1, or a complement thereof;

c) at least one oligonucleotide comprising a sequence at least 90% identical to at least 10 contiguous nucleotides of:
   i) human telomerase RNA (TERC);
   ii) human telomerase reverse transcriptase protein (TERT) mRNA;
   iii) a complement of TERC; or
   iv) a complement of TERT;
such that when the oligonucleotide and TERC or TERT mRNA are submitted to an amplification reaction, the oligonucleotide primes amplification of at least a fragment of TERC or TERT mRNA; and d) a detectably-labeled oligonucleotide comprising a sequence at least 90% identical to at least 10 contiguous nucleotides of:
   i) human telomerase RNA (TERC);
   ii) human telomerase reverse transcriptase protein (TERT) mRNA;
   iii) a complement of TERC; or
   iv) a complement of TERT.

In some embodiments, the kits comprise at least two different oligonucleotides comprising a sequence at least 90% identical to at least 10 contiguous nucleotides of SEQ ID NO:1, or a complement thereof, such that when the oligonucleotides and a polynucleotide comprising SEQ ID NO:1 are submitted to an amplification reaction, the oligonucleotides prime amplification of at least a fragment of SEQ ID NO:1; and at least two different oligonucleotides comprising a sequence at least 90% identical to at least 10 contiguous nucleotides of:
   i) human telomerase RNA (TERC);
   ii) human telomerase reverse transcriptase protein (TERT) mRNA;
   iii) a complement of TERC; or
   iv) a complement of TERT;
such that when the oligonucleotides and TERC or TERT mRNA are submitted to an amplification reaction, the oligonucleotides prime amplification of at least a fragment of TERC or TERT mRNA.

In some embodiments, the kit further comprises reverse transcriptase. In some embodiments, the kit further comprises a thermostable DNA polymerase.

In some embodiments, the detectably-labeled oligonucleotides comprises a fluorescent moiety. In some embodiments, the detectably-labeled oligonucleotides comprises quencher moiety.

The present invention also provides reaction mixture. In some embodiments, the reaction mixture comprises:

a) at least one oligonucleotide comprising a sequence at least 90% identical to at least 10 contiguous nucleotides of SEQ ID NO:1, or a complement thereof, such that when the oligonucleotide and a polynucleotide comprising SEQ ID NO:1 are submitted to an amplification reaction, the oligonucleotide primes amplification of at least a fragment of SEQ ID NO:1;

b) a detectably-labeled oligonucleotide comprising a sequence at least 90% identical to at least 10 contiguous nucleotides of SEQ ID NO:1, or a complement thereof;

c) at least one oligonucleotide comprising a sequence at least 90% identical to at least 10 contiguous nucleotides of:
   i) human telomerase RNA (TERC);
   ii) human telomerase reverse transcriptase protein (TERT) mRNA;
   iii) a complement of TERC; or
   iv) a complement of TERT;
such that when the oligonucleotide and TERC or TERT mRNA are submitted to an amplification reaction, the oligonucleotide primes amplification of at least a fragment of TERC or TERT mRNA; and d) a detectably-labeled oligonucleotide comprising a sequence at least 90% identical to at least 10 contiguous nucleotides of:
   i) human telomerase RNA (TERC);
   ii) human telomerase reverse transcriptase protein (TERT) mRNA;
   iii) a complement of TERC; or
   iv) a complement of TERT.

In some embodiments, the reaction mixture comprises at least two different oligonucleotides comprising a sequence at least 90% identical to at least 10 contiguous nucleotides of SEQ ID NO:1, or a complement thereof, such that when the oligonucleotides and a polynucleotide comprising SEQ ID NO:1 are submitted to an amplification reaction, the oligonucleotides prime amplification of at least a fragment of SEQ ID NO:1; and at least two different oligonucleotides comprising a sequence at least 90% identical to at least 10 contiguous nucleotides of:
   i) human telomerase RNA (TERC);
   ii) human telomerase reverse transcriptase protein (TERT) mRNA;
   iii) a complement of TERC; or
   iv) a complement of TERT;
such that when the oligonucleotides and TERC or TERT mRNA are submitted to an amplification reaction, the oligonucleotides prime amplification of at least a fragment of TERC or TERT mRNA.

In some embodiments, the reaction mixture further comprises a reverse transcriptase. In some embodiments, the reaction mixture further comprises a thermostable DNA polymerase. In some embodiments, the reaction mixture further comprises the detectably-labeled oligonucleotides comprises a fluorescent moiety. In some embodiments, the reaction mixture further comprises the detectably-labeled oligonucleotides comprises quencher moiety.

The present invention also provides for determination of the quantity of SENP1 and telomerase in a biological sample from an individual. In some embodiments, the quantity of SENP1 is detected by detecting a polynucleotide encoding SENP1 in the sample. In some embodiments, the polynucleotide is RNA.

In some embodiments, the sequence of the polynucleotide is determined. In some embodiments, the detection step comprises amplifying the polynucleotide in an amplification reaction. In some embodiments, the amplification reaction comprises at least two different oligonucleotides comprising a sequence at least 90% identical to at least 10 contiguous nucleotides of SEQ ID NO:1, or a complement thereof, such that during the amplification reaction the oligonucleotides prime amplification of at least a fragment of SEQ ID NO:1. In some embodiments, the amplification reaction is a quantitative amplification reaction. In some embodiments, the amplification product of the amplification reaction is detected in a step comprising hybridizing a detectably-labeled oligonucleotide to the product. In some embodiments, the detectably-labeled oligonucleotide comprises a fluorescent moiety. In some embodiments, the detectably-labeled oligonucleotide comprises a quencher moiety. In some embodiments, the amplification reaction comprises a template-dependent nucleic acid polymerase with 5'-3' exonuclease activity under conditions that allow the polymerase to fragment the detectably-labeled oligonucleotide.

In some embodiments, the amplification reaction is a reverse transcriptase polymerase chain reaction (RT-PCR). In some embodiments, the RT-PCR reaction is a quantitative RT-PCR reaction.

In some embodiments, the quantity of the polynucleotide is normalized.

In some embodiments, the quantity of SENP1 is determined by detecting a SENP1 polypeptide in the sample. In some embodiments, the polypeptide is detected by contacting the polypeptide with an antibody In some embodiments, SENP1 is detected by detecting SENP1 activity.

In some embodiments, telomerase is detected by detecting telomerase activity. In some embodiments, telomerase activity is detected by detecting elongation of an oligonucleotide comprising two or more repeats of TTAGG.

In some embodiments, telomerase is detected by detecting a component of telomerase in the sample. In some embodiments, the component is human telomerase RNA (TERC). In some embodiments, the component is human telomerase reverse transcriptase protein (TERT).

In some embodiments, telomerase is detected by detecting human telomerase reverse transcriptase protein (TERT) mRNA.

In some embodiments, the method comprises amplifying a SENP1 polynucleotide and a telomerase polynucleotide in a multiplex amplification reaction. In some embodiments, the telomerase polynucleotide is human telomerase RNA (TERC). In some embodiments, the telomerase polynucleotide is human telomerase reverse transcriptase protein (TERT) mRNA.

In some embodiments, the methods further comprise comparing the quantity of SENP1 and telomerase in the sample to a SENP1 standard and a telomerase standard representing SENP1 and telomerase quantities in non-cancer cells. In some embodiments, the standards are pre-determined values.

In some embodiments, the individual is a human.

In some embodiments, the biological sample comprises a bodily fluid. In some embodiments, the bodily fluid is blood. In some embodiments, the bodily fluid is urine. In some embodiments, the sample is from a tissue biopsy. In some embodiments, the method further comprises obtaining a biological sample from the individual.

In some embodiments, the individual has or is suspected of having cancer.

In some embodiments, the cancer is bladder cancer.

In some embodiments, the method further comprises recording a diagnosis of the presence or absence of cancer in the individual. In some embodiments, the method further comprises recording a prognosis for cancer treatment and/or survival for the individual. In some embodiments, the method further comprises recording the progression of cancer in the individual. In some of these embodiments, the cancer is bladder cancer.

DEFINITIONS

Figure 1:
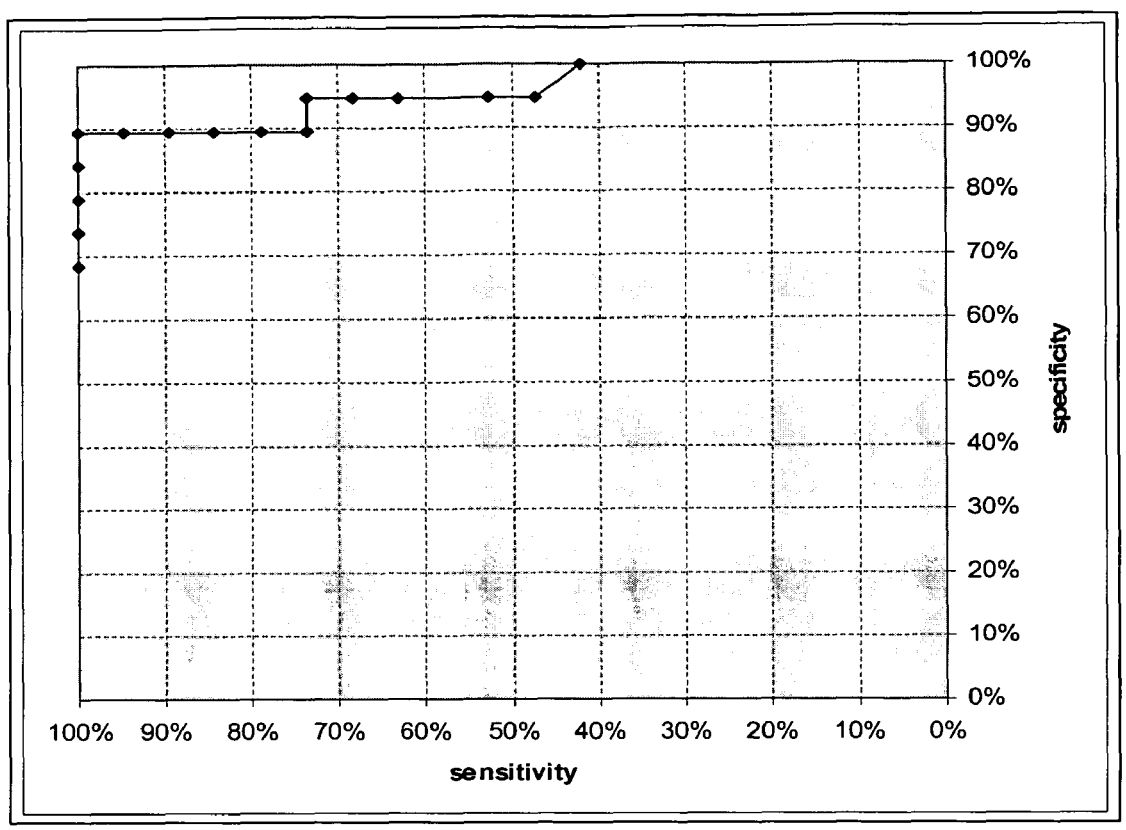
FIG. 1 depicts a typical receiver-operator curve of SENP1 mRNA from telomerase negative bladder cancer patient urine sediment and from healthy subject's urine sediment.

"SENP1" refers to a sentrin/SUMO-specific protease polypeptide or a polynucleotide encoding the polypeptide. Exemplary SENP1 polynucleotides include, e.g., Genbank accession number NM_014554 (SEQ ID NO:1). Exemplary SENP1 polypeptides include, e.g., the polypeptide depicted in Genbank accession number NP_055369 (SEQ ID NO:2). "SENP1" is intended to encompass allelic variants of those sequences specifically provided herein, as well as fragments and mutations thereof. SENP1 polynucleotides will generally be at least 90%, 95% or 99% identical to SEQ ID NO:1 or 90%, 95% or 99% identical to DNA sequences encoding SEQ ID NO:2. SENP1 polynucleotides include, e.g., mRNA encoding SENP1 polypeptides as well as DNA sequences (e.g., cDNA or genomic DNA) encoding SENP1 polypeptides. SENP1 polypeptides will generally be at least 90%, 95% or 99% identical to SEQ ID NO:2.

"Telomerase" refers to a ribo-protein complex that maintains the ends of chromosomes (telomeres) or polynucleotides encoding components of the ribo-protein. See, e.g., Shippen-Lentz et al., Science 247:546 (1990); Greiden et al., Nature 337:331 (1989). Telomerse includes two main components: telomerase reverse transcriptase protein (encoded by the gene, TERT) and the telomerase RNA component (encoded by the gene, TERC). The equivalent human components are known as TERT (e.g., protein sequence: NP_003210 (SEQ ID NO:3), encoded by, e.g., nucleotide sequence: NM_003219 (SEQ ID NO:4)) and TERC (NR_001566 (SEQ ID NO:5)). Splice variants of the RNA encoding TERT are intended to be encompassed by this definition.

"Contacting a plurality of agents to a cell" refers to contacting at least two agents to a cell or cells. While multiple agents may be contacted to one cell or pool of cells, the phrase also encompasses contacting a first agent to a first cell or pool of cells and a second agent to a second cell or pool of cells, e.g., such that each cell or pool of cell is contacted by a single agent.

"Determining the quantity of SENP1 or telomerase" refers to using any technique known to those of skill in the art to quantify the amount of SENP1 or telomerase polypeptide or polynucleotide (e.g., structural RNA, mRNA or cDNA) or SENP1 or telomerase activity in a sample.

A "neoplastic phenotype" refers to the phenotype of a neoplastic cell. Exemplary phenotypes include, e.g., cell growth on soft agar; anchorage independence; reduced contact inhibition and/or density limitation of growth; cellular proliferation; cellular transformation; growth factor or serum independence; accumulation of tumor specific marker levels; invasiveness into Matrigel; tumor growth and metastasis in vivo; mRNA and protein expression patterns of cells undergoing metastasis; and other characteristics of cancer cells.

An "amplification reaction" refers to any reaction (e.g., chemical or enzymatic) that results in increased copies of a template nucleic acid sequence or increased signal indicating the presence of the template nucleic acid. "Selective amplification" or "selectively amplifying" refers to amplification of particular sequences in a population of sequences.

The term "biological sample" encompasses a variety of sample types obtained from an organism and can be used in a diagnostic or monitoring assay. The term encompasses urine, urine sediment, blood, saliva, and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, sedimentation, or enrichment for certain components. The term encompasses a clinical sample, and also includes cells in cell culture, cell supernatants, cell lysates, serum, plasma, biological fluids, and tissue samples.

An "antagonist" refers to a molecule which, when contacted to a cell expressing SENP1, inhibits SENP1 activity or expression. Antagonists are compounds that, e.g., bind to, partially or totally block activity, decrease, prevent, delay activation, inactivate, desensitize, or down regulate the activity or expression of SENP1.

As used herein, the terms "nucleic acid," "nucleotide," "polynucleotide" and "oligonucleotide" refer to primers, probes, oligomer fragments to be detected, oligomer controls and unlabeled blocking oligomers and is generic to polydeoxyribonucleotides (containing 2-deoxy-D-ribose), to polyribonucleotides (containing D-ribose), and to any other N-glycoside of a purine or pyrimidine base, or modified purine or pyrimidine bases.

A nucleic acid, nucleotide, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The terms encompass peptide-nucleic acids (PNAs) and intercalating nucleic acids (INAs).

A nucleic acid, nucleotide, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, $N^6$-methyl-adenine, $N^6$-tert-butyl-benzyl-adenine, imidazole, substituted imidazoles, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or dervatized base moities may be found in U.S. Pat. Nos. 6,001,611, 5,955,589, 5,844,106, 5,789,562, 5,750,343, 5,728,525, and 5,679,785, each of which is incorporated herein by reference in its entirety.

Furthermore, a nucleic acid, nucleotide, polynucleotide or oligonucleotide can comprise one or more modified sugar moieties including, but not limited to, arabinose, 2-fluoroarabinose, xylulose, and hexose.

It is not intended that the present invention be limited by the source of a nucleic acid, nucleotide, polynucleotide or oligonucleotide. A nucleic acid, nucleotide, polynucleotide or oligonucleotide can be from a human or non-human mammal, or any other organism, or derived from any recombinant source, synthesized in vitro or by chemical synthesis. A nucleic acid, nucleotide, polynucleotide or oligonucleotide may be DNA, RNA, cDNA, DNA-RNA, locked nucleic acid (LNA), peptide nucleic acid (PNA), a hybrid or any mixture of the same, and may exist in a double-stranded, single-stranded or partially double-stranded form. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, and the like.

There is no intended distinction in length between the terms nucleic acid, nucleotide, polynucleotide and oligonucleotide, and these terms will be used interchangeably. These terms include double- and single-stranded DNA, as well as double- and single-stranded RNA. While oligonucleotides may be any length, they may have fewer than 500 nucleotides, e.g., 5-100, 10-100, 10-30, 15-30, or 15-50 nucleotides.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The phrase "selectively (or specifically) hybridizes to" refers to the binding, duplexing, or hybridizing of a molecule predominantly (e.g., at least 50% of the hybridizing molecule) to a particular nucleotide sequence under stringent hybridization conditions when that sequence is present in a complex mixture (e.g., total cellular or library DNA or RNA). Polynucleotide primers specifically hybridize to a polynucleotide template in an amplification reaction (e.g., at an annealing temperature of about 60° C.) when the primers amplify the template in a reaction mixture comprising a complex mixture of polynucleotides (e.g., isolated from a cell) to produce an amplification product that is at least the most predominant amplification product and is preferably the only significant (e.g., representing at least 90-95% of all amplification products in the sample) amplification product of the reaction.

The phrase "stringent hybridization conditions" refers to conditions under which a probe will predominantly hybridize to its target subsequence in a complex mixture of nucleic acids. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Exemplary cycle conditions for both high and low stringency amplifications include, but are not limited to, a denaturation phase of about 30 seconds to about 2 minutes at 90° C.-95° C., an annealing phase of about 5 seconds to about 2 minutes at 50° C.-70° C., and an extension phase of about 1 minute to about 5 minutes at about 70° C.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to V$_H$-C$_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised against SENP1 can be selected to obtain only those polyclonal antibodies that are specifically immunoreactive with SENP1 and not with other proteins, except for polymorphic variants and alleles of SENP1. This selection may be achieved by subtracting out antibodies that cross-react with SENP1 molecules from other species or that cross-react with non-SENP1 proteins. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The terms "identical" or "100% identity," in the context of two or more nucleic acids or polypeptide sequences, refer to two or more sequences or subsequences that are the same sequences. Two sequences are "substantially identical" or a certain percent identity if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides oligonucleotides that are substantially identical to at least 5, 6, 7, 8, 9, 10, 11, 12, 13, 14, 15, 16, 17, 18, 19, 20, 21, 22, 23, 24, 25, 30, 40, 50, or more contiguous nucleotides of SENP1 polynucleotides or telomerase polynucleotides or complements thereof.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 5 to 600, usually about 10 to about 100, more usually about 15 to about 50 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Two examples of algorithms that are suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands. Either program is run with the low complexity filter "off".

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

DETAILED DESCRIPTION OF THE INVENTION

I. Introduction

Not all tumors of a given cancer type contain detectable levels of telomerase activity. See, e.g., Shay, J. W. and Bacchetti, S. *Eur. J. Cancer,* 33:787-791 (1997); Yan, P. et al. *Cancer Res.* 59: 3166-3170 (1999). In general, 50-100% of tumors of different types have measurable telomerase activity (Bryan, T. M., *Nature Medicine* 3:1271-1274 (1997); Kim, N. W. et al. *Science* 266:2011-2015 (1994); Bacchetti, S. and Counter, C. M. *Int. J. Oncology* 7:423-432 (1995)). Thus, while this failure to detect telomerase activity could be due to an inability to measure low levels, it is more likely that expression of telomerase may be sufficient to cause cancer, but it is not necessary. That is, some tumors may not express active telomerase.

Indeed it has been found that some immortalized cell lines and tumors are capable of maintaining telomeres without telomerase. See, e.g., Bryan, et al. *Nature Medicine* 3: 1271-1274 (1997); Scheel, C. and Poremba, C. *Virchows Arch* 440: 573-582 (2002); McEachern, M. J., et al. *Annu. Rev. Genet.* 34: 331-58 (2000)). This alternative lengthening of telomeres (ALT), at least in some cases, occurs by homologous recombination (Dunham, M. A, et al. *Nature Genetics* 26:447-450 (2000)). Epithelial cells appear to be immortalized by ALT much less frequently than fibroblasts (Bryan, T. M., et al. *Nature Medicine* 3:1271-1274 (1997); Mehle, C., et al. *Oncogene* 13: 161-166 (1996)).

Interestingly, cancers are largely epithelial in origin, which may account for the generally high percentages of tumors which are telomerase positive. However, if telomeres of tumors in some populations of patients are maintained by a telomerase-independent mechanism, this sets the upper limit of obtainable sensitivity for any telomerase-based assay designed to diagnose or monitor recurrence of a cancer. Certain tumors would escape detection using telomerase as the only cancer marker.

The inventors recognized a need for a method of detecting tumors that do not express telomerase. The present invention is based in part on the discovery that increased expression of SENP1 is a useful marker to identify cancers that do not have detectable telomerase levels. Thus, by detecting both SENP1 and telomerase in a sample, it is possible to detect a significant number of cancers. Accordingly, the present invention provides methods of detecting the presence of cancer cells in a biological sample by determining the quantity of SENP1 and telomerase in the sample.

In addition, the present invention is based in part on the discovery that increased expression of SENP1 is a useful marker to identify cancer, including, e.g., bladder cancer, breast cancer, colon cancer, kidney cancer, lung cancer, ovarian cancer, pancreatic cancer, small intestine cancer, and bladder cancer. Moreover, the inventors have shown that the use of both SENP1 and telomerase as markers can allow for greater sensitivity and specificity for detecting selected cancers rather than use of either marker alone. Accordingly, the present invention provides methods of detecting the presence of cancer cells in a biological sample by determining the quantity of SENP1 and, optionally telomerase, in the sample. Thus, in some embodiments of the invention, both SENP1 and telomerase are detected, wherein an increase in either marker indicates the presence of, e.g., bladder cancer, breast cancer, colon cancer, kidney cancer, lung cancer, ovarian cancer, pancreatic cancer, small intestine cancer, or bladder cancer.

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 2002).

II. Detection and Quantification of SENP1 and/or Telomerase

The present invention provides for any methods of quantifying SENP1 and/or telomerase polynucleotides (including SENP1 mRNA, SENP1 cDNA, TERT mRNA, TERT cDNA, TERC RNA, TERC cDNA, etc.) and/or SENP1 and/or telomerase polypeptides and/or the activity of SENP1 and/or telomerase known to those of skill in the art either sequentially or simultaneously in one or multiple assays. Exemplary approaches for detecting SENP1 or telomerase detection include, e.g., (a) detection of SENP1 or telomerase polynucleotides, including using polynucleotide hybridization and/or amplification reaction-based assays; (b) detection of SENP1 or telomerase proteins, including using affinity agent-based assays involving an agent that specifically binds to a SENP1 or telomerase polypeptide or polynucleotide; and/or (c) detection of SENP1 or telomerase activity. All of these methods allow for subsequent direct or indirect quantification of the detected targets, i.e., SENP1 and telomerase.

Typically, the cancer-associated SENP1 polynucleotides or polypeptides detected herein will be at least about 90%, 91%, 92%, 93%, 94%, 95%, 96%, 97%, 98%, 99% or more identical to SEQ ID NO:1 or to those polynucleotides encoding SEQ ID NO:2 or to one or more of the SENP1 sequences available, e.g., from GenBank (see, e.g., SENP mRNA sequence at NM_014554 and the SENP1 polypeptide at NP_055369). Similarly, telomerase polynucleotides (e.g., TERT RNA or TERC) or polypeptides (e.g., TERT) detected herein will be at least about 90%, 91%, 92%, 93%, 94%, 95%, 96%, 97%, 98%, 99% or more identical to a telomerase polynucleotide or polypeptide. The detected SENP or telomerase polynucleotides or polypeptides can represent functional or nonfunctional forms of the cancer-associated polynucleotide or polypeptide, or any variant, derivative, or fragment thereof. Typically, the level and/or presence of cancer-associated polynucleotides or polypeptides in a biological sample will be detected.

Methods of detecting telomerase expression may include the same type methods as used for detecting SENP1 (e.g., both telomerase and SENP1 polynucleotides are detected) or different methods (e.g., SENP1 polynucleotides and telomerase activity are detected). However, for user convenience, it can be desirable to use the same detection assay for both telomerase and SENP1. For example, in some embodiments, quantitative multiplex reverse transcription-polymerase chain reaction (RT-PCR) reactions can be used to quantify both SENP1 and telomerase expression in a sample. In some embodiments, real-time quantitative RT-PCR is performed.

A. Detection of mRNA Expression

Detection assays may be carried out on preparations containing mRNA or cDNA generated from isolated mRNA in a manner that reflects the relative levels of mRNA transcripts in the sample. Methods of detecting telomerase RNA have been described and can generally be adapted for detecting SENP1. See, e.g., U.S. Pat. Nos. 6,582,964; 5,846,723; 6,607,898; U.S. patent Publication No. 2002/0012969; and Angelopoulou et al., *Anticancer Res.* 23(6C):4821-9 (2003).

1. Amplification-Based Assays a. Detection Methods

In some embodiments, levels of RNA can be determined using amplification reactions, such as PCR. For example, using one or more oligonucleotide primers can be used to amplify a region of a SENP1 polynucleotide (e.g., a SENP1 or telomerase cDNA). Amplification reactions useful for the present invention include, but are not limited to, polymerase chain reaction (PCR) and ligase chain reaction (LCR) (see U.S. Pat. Nos. 4,683,195 and 4,683,202; *PCR Protocols. A Guide to Methods and Applications* (Innis et al., ed., 1990)), strand displacement amplification (SDA) (Walker, et al. *Nucleic Acids Res.* 20(7):1691-6 (1992); Walker, *PCR Methods Appl* 3(1):1-6 (1993)), transcription-mediated amplification (Phyffer, et al., *J. Clin. Microbiol.* 34:834-841 (1996); Vuorinen, et al., *J. Clin. Microbiol.* 33:1856-1859 (1995)), nucleic acid sequence-based amplification (NASBA) (Compton, *Nature* 350(6313):91-2 (1991), rolling circle amplification (RCA) (Lisby, *Mol. Biotechnol.* 12(1):75-99 (1999)); Hatch et al., *Genet. Anal.* 15(2):35-40 (1999)) branched DNA signal amplification (bDNA) (see, e.g., Iqbal et al., *Mol. Cell Probes* 13(4):315-320 (1999)) and Q-Beta Replicase (Lizardi et al., *Bio/Technology* 6:1197 (1988)).

Although any type of amplification reaction can be used, in some embodiments, PCR is used to amplify DNA templates. The PCR primers will typically be designed to specifically hybridize to the SENP1 polynucleotide, e.g., under conditions used in a PCR reaction. For example, primers typically hybridize in standard PCR buffers (such as, but not limited to, those containing 50 mM bicine, pH 8.0, 115 mM potassium acetate, 8% glycerol, 3 mM manganese acetate, 200 uM each deoxyadenosine triphosphate, deoxycytidine triphospate, deoxyguanosine triphosphate, and 500 uM of deoxyuridine triphosphate, 2 Units of uracil N-glycosylase (UNG), 10 Units of DNA polymerase, 200 nM each primer, forward and reverse, and optionally a polynucleotide probe) at about 60° C. Generally, primers are designed and/or tested to avoid significant homology or hybridization to other polynucleotides likely to be found in the biological sample (e.g., in the human genome). Alternative methods of amplification (e.g., LCR, SDA, RCA, Q-Beta, etc.) have been described and can also be employed.

In some embodiments, SENP1 or telomerase RNA can be detected using reverse transcriptase polymerase chain reaction (RT-PCR). RT-PCR methods are well known to those of skill (see, e.g., *Current Protocols in Molecular Biology* (Ausubel et al., eds., 2002)).

Amplification methods employed to detect SENP1 polynucleotides may involve a quantitative PCR methodology such as, for example, the real-time PCR, including quantitative RT-PCR. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1): 106-10, 112-5 (2003); Deiman B, et al., *Mol Biotechnol.* 20(2):163-79 (2002).

To quantify the amount of specific RNA in a sample, a standard curve may be generated from run-off transcription of a plasmid containing the gene of interest. Standard curves may be generated using the threshold values (Ct) values determined in the real-time PCR, which are related to the initial cDNA concentration used in the assay. In addition, a standard curve may be generated for a standard polynucleotide (e.g., a previously quantified sequence). This permits standardization of initial RNA content of a biological sample to the amount of standard for comparison purposes. See, e.g., THE PCR TECHNIQUE: QUANTITATIVE PCR (J. Larrick, ed., 1997).

One method for detection of amplification products is the 5' nuclease PCR assay (using e.g., COBAS TaqMan 48 Analyzer™ (Roche Molecular Systems, Pleasanton, Calif.)). See, e.g., Holland et al., *Proc. Natl. Acad. Sci. USA* 88: 7276-7280 (1991); Lee et al., *Nucleic Acids Res.* 21: 3761-3766 (1993); U.S. Pat. Nos. 6,214,979; 5,804,375; 5,487,972; and 5,210,015. This assay detects the accumulation of a specific PCR product by hybridization and cleavage of a doubly labeled fluorogenic probe during the amplification reaction. The fluorogenic probe may consist of an oligonucleotide (e.g., that hybridizes to a SENP1 or telomerase polynucleotide or its complement) labeled with both a fluorescent reporter dye and a quencher dye. During PCR, this probe is cleaved by the 5'-nuclease activity of DNA polymerase if, and only if, it hybridizes to the segment being amplified. Cleavage of the probe generates an increase in the fluorescence intensity of the reporter dye.

In some embodiments, the enzymes with 5' nuclease activity are thermostable and thermoactive nucleic acid polymerases. Such thermostable polymerases include, but are not limited to, native and recombinant forms of polymerases from a variety of species of the eubacterial genera *Thermus, Thermatoga*, and *Thermosipho*. For example, *Thermus* species polymerases that can be used in the methods of the invention include *Thermus aquaticus* (Taq) DNA polymerase, *Thermus thermophilus* (Tth) DNA polymerase, *Thermus* species Z05 (Z05) DNA polymerase, *Thermatoga maritima* DNA polymerase, *Thermatoga neapolitana* DNA polymerase and *Thermus* species sps17 (sps17), as described in U.S. Pat. Nos. 5,405,774, 5,352,600, 5,079,352, 4,889,818, 5,466,591, 5,618,711, 5,674,738, and 5,795,762.

Another method of detecting amplification products that relies on the use of energy transfer is the "molecular beacon probe" method described by Tyagi and Kramer (*Nature Biotech.* 14:303-309 (1996)), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce (Tyagi and Kramer, *Nature Biotechnol.* 14: 303-306 (1996). As a result, the amount of fluorescence will increase as the amount of PCR product increases, and thus may be used as a measure of the progress of the PCR. Those of skill in the art will recognize that other methods of quantitative amplification are also available.

Other types of probes useful for real time PCR methods include Scorpion™) probes, which are available in "uni-labeled" and "bi-labeled" formats from Proligo, C (Boulder, Colo.). See, also, Bates et al., *Mol. Plant Pathol.* 2(5):275-280 (2001).

In still another example, two primers and a probe of the invention may be used to detect and quantify a target nucleic acid using nucleic acid sequence-based amplification (NASBA). In some NASBA methods, three enzymes are used, including reverse transcriptase, T7 RNA polymerase, and RNase H. The final amplification product is single-stranded RNA with a polarity opposite that of the nucleic acid to be detected. The amplified RNA product can be detected in some embodiments through the use of a target-specific capture probe bound to magnetic particles in conjunction with a ruthenium-labeled detector probe and an instrument (NucliSens Reader; bioMerieux) capable of measuring electrochemiluminescence (ECL). Alternatively, RNA amplified by NASBA can specifically be detected in real time by including molecular beacon probes in the amplification reaction, as described above. Further guidance on use of the primers and probes of the invention may be found in articles by Compton, *Nature* 350:91-92 (1991) and Kievits et al., *J. Virol. Methods* 35:273-86 (1991).

Another example of methods that use a nucleic acid primer and a probe to detect and quantify a target nucleic acid involves the use of nanoparticles. In such methods, two oligonucleotides, such as a primer or probe of the invention, that can hybridize to different regions of a nucleic acid to be detected are covalently linked to a nanoparticle. The nanoparticles are contacted with a target nucleic acid under hybridization conditions. If the nucleic acid is present, the nucleic acid will bind to the oligonucleotides attached to the nanoparticles, producing a large molecular weight complex that can be detected. The complex can be detected by any method known to one of skill in the art without limitation. In certain embodiments, the complex is detected by precipitation of the complex. Further guidance on methods of using nanoparticles in connection with the primers and probes of the invention may be found in Taton et al., *Science* 289(5485): 1757-60 (2000) and U.S. Pat. Nos. 6,506,564, 6,495,324, 6,417,340, 6,399,303, and 6,361,944.

In yet another example, rolling circle amplification ("RCA") can be used as part of a method for detecting and quantifying a target nucleic acid. In certain embodiments of RCA methods, a DNA circle is amplified by polymerase extension of a complementary primer. Any of the primers or probes of the invention can be used in such methods. Methods of ciruclarizing DNA are well known in the art, and include, for example, ligating the ends of a DNA molecule together under conditions which favor intramolecular ligation. The single-stranded product concatamer product can then be detected by any method of detecting a nucleic acid known to one of skill in the art without limitation. For example, the concatamer product can be detected using a detectably-labeled probe of the invention. Other examples of methods of detecting a nucleic acid of known sequence are extensively described herein. In other embodiments of RCA, a second primer can be used that is complementary to the concatemer product. This primer allows exponential amplication of the sequences present in the circular DNA template. The products of the amplification can still be detected, for example, by using a detectably-labeled probe of the invention. Further guidance on using the primers and probes of the invention in RCA methods for detecting a target nucleic acid may be found in U.S. Pat. Nos. 6,344,329, 6,350,580, 6,221,603, 6,210,884, 5,648,245, and 5,714,320 and WO95/35390.

In another example of such methods, a target nucleic acid can be detected and quantified using Strand Displacement Amplification ("SDA"). In such methods, amplified nucleic acids are detected by incorporation of a single-stranded primer that comprises a fluorescent moiety, a quencher moiety, and an engineered restriction site separating the two moieties. One of skill in the art can easily recognize how to modify any of the primers or probes of the invention for use in SDA.

In a first amplification reaction used in SDA, the primer is used to amplify a target nucleic acid in the presence of, for example, thio-dCTP, thereby incorporating the primer into the amplification product. Then, a restriction endonuclease can be used to nick the restriction site in the primer. The restriction endonuclease cannot cut both strands of the amplification product because of the incorporation of thio-dCTP in the amplification product. Finally, the 3' end of the primer created by the nick can be used to prime a new polymerization reaction, thereby displacing the portion of the strand 3' to the nick from the template strand. Displacement of the strand separates the fluorescent moiety from the quencher moiety, thereby preventing quenching of fluorescence emitted by the fluorescent moiety. A SENP1 or telomerase polynucleotide can thereby be detected and/or quantified by measuring the presence and/or amount of fluorescence. Further guidance on selection and modification of primers and probes for use in SDA may be found in Little et al., *Clin. Chem.* 45-777-784 (1999) and U.S. Pat. Nos. 6,528,254 and 6,528,632.

In another example, a SENP1 or telomerase polynucleotide may be detected and quantified using transcription-mediated amplification ("TMA"). TMA is an RNA transcription amplification system that uses RNA polymerase and reverse transcriptase to amplify the nucleic acids to be detected. In the method, a primer of the invention with a promoter for RNA polymerase is used to prime reverse transcription of a target RNA. The RNAse activity of reverse transcriptase then degrades the RNA template, releasing the cDNA strand. Second strand synthesis is primed with a second primer of the invention and catalyzed by reverse transcriptase. RNA polymerase then recognizes the promoter synthesized in the second strand and catalyzes multiple cycles of RNA transcription from the second strand. The RNA product can then be detected or can serve as template for another round of amplification.

The RNA product of TMA can then be detected and quantified by any method known to one of skill in the art. In certain embodiments, the RNA product can be detected with a probe of the invention. In other embodiments, the RNA product can be detected with a probe of the invention that has been labeled with an acridine-ester label (Gen-Probe, Inc., San Diego, Calif.). Such labels can be chemically removed from unhybridized probe while labels on hybridized probes remain undisturbed. Thus, in such embodiments, presence of a target nucleic acid can be detected by detecting the presence of the acridine-ester label. Further guidance in using the primers and probes of the invention in TMA-based methods may be found in Arnold et al., *Clin. Chem.* 35:1588-1594 (1989), Miller et al., *J. Clin. Microbiol.* 32-393-397 (1994), and U.S. Pat. Nos. 6,335,166 and 6,294,338.

In other embodiments, any assay known by one of skill in the art that uses a single nucleic acid primer or probe that can hybridize to a nucleic acid to detect the nucleic acid can be used to detect a SENP1 or telomerase polynucleotide. For example, a SENP1 or telomerase polynucleotide can be detected using a primer to initiate a primer extension reaction. Successful extension of the primer by a nucleic acid polymerase indicates the presence of the SENP1 or telomerase polynucleotide. Other examples of single primer or probe detection methods that describe methods that can be used as described or adapted by one of skill in the art to detect a SENP1 or telomerase polynucleotide can be found in U.S. Pat. Nos. 6,440,707, 6,379,888, 6,368,803, 6,365,724, 6,361,944, 6,352,827, 6,326,145, 6,312,906, 6,268,128, 6,261,784, 6,177,249, 6,140,055, 6,130,047, 6,124,090, 6,121,001, 6,110,677, 6,054,279, 6,022,686, 5,981,176, 5,958,700, 5,945,283, 5,935,791, 5,919,630, 5,888,739, 5,888,723, 5,882,867, 5,876,924, 5,866,336, 5,856,092, 5,853,990, 5,846,726, 5,814,447, 5,808,036, 5,800,989, 5,795,718, 5,792,614, 5,710,028, 5,683,875, 5,683,872, 5,679,510, 5,641,633, 5,597,696, 5,595,890, 5,571,673, 5,547,861, 5,525,462, 5,514,546, 5,491,063, 5,437,977, 5,294,534, 5,118,605, 5,102,784, 4,994,373, 4,851,331, 4,767,700.

b. Primers of the Invention

Exemplary oligonucleotide primers may comprise a sequence at least 70%, 75%, 80%, 85%, 90%, 95% or 100% identical to at least 5, 6, 7, 8, 9, 10, 11, 12, 13, 14, 15, 16, 17, 18, 19, 20, 21, 22, 23, 24, 25, 30, 40, 50, or other number of contiguous nucleotides of SENP1 polynucleotides or telomerase (e.g., TERC or TERT) polynucleotides or complements thereof.

The length and composition of the probe can be chosen to give sufficient thermodynamic stability to ensure hybridization of the probe to the template nucleic acid under the appropriate reaction conditions, which depend on the detection method to be performed. For example, probes with modified, non-standard, or derivatized nucleotides may be longer or shorter than those with conventional nucleotides while having similar thermodynamic hybridization properties. Examples of such non-standard bases may be found in U.S. Pat. Nos. 6,320,005, 6,174,998, 6,001,611, and 5,990,303. As another example, probes with G/C-rich sequences may anneal to target sequences at higher temperatures than a probe of similar length with A/T-rich sequences.

C. Probes of the Invention

Exemplary detectably-labeled oligonucleotide probes may comprise a sequence at least 70%, 75%, 80%, 85%, 90%, 95% or 100% identical to at least 5, 6, 7, 8, 9, 10, 11, 12, 13, 14, 15, 16, 17, 18, 19, 20, 21, 22, 23, 24, 25, 30, 40, 50, or other number of contiguous nucleotides of SENP1 polynucleotides or telomerase (e.g., TERC or TERT) polynucleotides or complements thereof.

In addition to the probe nucleotide sequence as described herein, the probe can comprise additional nucleotide sequences or other moieties that do not inhibit the methods of the instant invention. In some embodiments of the invention, the probe can comprise additional nucleotide sequences or other moieties that facilitate the methods of the instant invention. For instance, the probe can be blocked at its 3' terminus to prevent undesired nucleic acid polymerization priming by the probe. Also, moieties may be present within the probe that stabilize or destabilize hybridization of the probe or probe fragments with the nucleotide sequence. The probes of the invention can also comprise modified, non-standard, or derivatized nucleotides as defined above.

In certain embodiments of the invention, the probe can comprise a detectable moiety. The detectable moiety can be any detectable moiety known by one of skill in the art without limitation. Further, the detectable moiety can be detectable by any means known to one of skill in the art without limitation. For example, the detectable moiety can be detectable by spectroscopic, photochemical, biochemical, immunochemical, or chemical means.

A variety of detectable moieties that can be used to detect the probes of the invention, as well as methods for their linkage to the probe, are known to the art and include, but are not limited to, enzymes (e.g., alkaline phosphatase and horseradish peroxidase) and enzyme substrates, radioactive moieties, fluorescent moieties, chromophores, chemiluminescent labels, electrochemiluminescent labels, such as Origin™ (Igen, Rockville, Md.), ligands having specific binding partners, or any other labels that may interact with each other to enhance, alter, or diminish a signal. Of course, if a 5' nuclease reaction is performed using a thermostable DNA polymerase at elevated temperatures, in some embodiments, the detectable moiety is not degraded or otherwise rendered undetectable by such elevated temperatures.

In certain embodiments, the detectable moiety can be a fluorescent moiety. The fluorescent moiety can be any fluorescent moiety known to one of skill in the art without limitation. In some embodiments, fluorescent moieties with wide Stokes shifts are used, allowing for the use of fluorometers with filters rather than monochromometers and increasing the efficiency of detection. In certain embodiments, the fluorescent moiety can be selected from the group consisting of fluorescein-family dyes (Integrated DNA Technologies, Inc., Coralville, Iowa), polyhalofluorescein-family dyes, hexachlorofluorescein-family dyes, coumarin-family dyes (Molecular Probes, Inc., Eugene, Oreg.), rhodamine-family dyes (Integrated DNA Technologies, Inc.), cyanine-family dyes, oxazine-family dyes, thiazine-family dyes, squaraine-family dyes, chelated lanthanide-family dyes, and BODIPY®-family dyes (Molecular Probes, Inc.). In some embodiments, the fluorescent moiety is 6-carboxyfluorescein (FAM™) (Integrated DNA Technologies, Inc.). Other examples of fluorescent moieties that can be used in the probes, methods, and kits of the invention can be found in U.S. Pat. Nos. 6,406,297, 6,221,604, 5,994,063, 5,808,044, 5,880,287, 5,556,959, and 5,135,717.

In other embodiments, the detectable moiety can be a detectable moiety other than a fluorescent moiety. Among radioactive moieties, $^{32}$P-labeled compounds are preferred. Any method known to one of skill in the art without limitation may be used to introduce $^{32}$P into a probe. For example, a probe may be labeled with $^{32}$P by 5' labeling with a kinase or by random insertion by nick translation. Detectable moieties that are enzymes can typically be detected by their activity. For example, alkaline phosphatase can be detected by measuring fluorescence produced by action of the enzyme on appropriate substrate compounds. Where a member of specific binding partners is used as detectable moieties, the presence of the probe can be detected by detecting the specific binding of a molecule to the member of the specific binding partner. For example, an antigen can be linked to the probe, and a monoclonal antibody specific for that antigen can be used to detect the presence of the antigen and therefore the probe. Other specific binding partners that can be used as detectable moieties include biotin and avidin or streptavidin, IgG and protein A, and numerous other receptor-ligand couples well-known to the art. Still other examples of detectable moieties that are not fluorescent moieties can be found in U.S. Pat. Nos. 5,525,465, 5,464,746, 5,424,414, and 4,948,882.

The above description of detectable moieties is not meant to categorize the various labels into distinct classes, as the same label may serve in several different modes. For example, $^{125}$I may serve as a radioactive moiety or as an electron-dense reagent. Horseradish peroxidase may serve as enzyme or as antigen for a monoclonal antibody. Further, one may combine various detectable moieties for desired effect. For example, one might label a probe with biotin, and detect its presence with avidin labeled with $^{125}$I, or with an anti-biotin monoclonal antibody labeled with horseradish peroxidase. Other permutations and possibilities will be readily apparent to those of ordinary skill in the art, and are considered as equivalents within the scope of the instant invention.

The method of linking or conjugating the detectable moiety to the probe depends, of course, on the type of detectable moiety or moieties used and the position of the detectable moiety on the probe.

The detectable moiety may be attached to the probe directly or indirectly by a variety of techniques. Depending on the precise type of detectable moiety used, the detectable moiety can be located at the 5' or 3' end of the probe, located internally in the probe's nucleotide sequence, or attached to spacer arms of various sizes and compositions to facilitate signal interactions. Using commercially available phosphoramidite reagents, one can produce oligonucleotides containing functional groups (e.g., thiols or primary amines) at either terminus via an appropriately protected phosphoramidite, and can attach a detectable moiety thereto using protocols described in, for example, PCR PROTOCOLS: A GUIDE TO METHODS AND APPLICATIONS (ed., Innis et al. (1990)).

Methods for introducing oligonucleotide functionalizing reagents to introduce one or more sulfhydryl, amino or hydroxyl moieties into the oligonucleotide probe sequence, typically at the 5' terminus are described in U.S. Pat. No. 4,914,210. A 5' phosphate group can be introduced as a radioisotope by using polynucleotide kinase and [gamma-$^{32}$P]ATP to provide a reporter group. Biotin can be added to the 5' end by reacting an aminothymidine residue or alkylamino linker, introduced during synthesis, with an N-hydroxysuccinimide ester of biotin. Other methods of attaching a detectable moiety, including a fluorescent moiety, to the probe can be found in U.S. Pat. No. 5,118,802.

It is also possible to attach a detectable moiety at the 3' terminus of the probe by employing, for example, polynucleotide terminal transferase to add a desired moiety, such as, for example, cordycepin $^{35}$S-dATP, and biotinylated dUTP.

Oligonucleotide derivatives are also detectable moieties that can be used in the probes, methods and kits of the present invention. For example, etheno-dA and etheno-A are known fluorescent adenine nucleotides which can be incorporated into an oligonucleotide probe. Similarly, etheno-dC is another analog that could be used in probe synthesis. The probes containing such nucleotide derivatives can be degraded to release mononucleotides that are much more strongly fluorescent than the intact probe by, for example, a polymerase's 5' to 3' nuclease activity.

In certain embodiments of the invention, a probe can be labeled with more than one detectable moiety. In certain of such embodiments, each detectable moiety can be individually attached to different bases of the probe. In other embodiments, more than one detectable moiety can be attached to the same base of the probe.

In certain embodiments, the detectable moiety can be attached to the 5' end of the probe. In other embodiments, the detectable moiety can be attached to the probe at a residue that is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, about 40 residues or other number of residues from the 5' end of the probe. The detectable moiety can be attached to any portion of a residue of the probe. For example, the detectable moiety can be attached to a sugar, phosphate, or base moiety of a nucleotide in the probe. In other embodiments, the detectable moiety can be attached between two residues of the probe.

In certain embodiments of the invention, the probe can comprise a fluorescent moiety and a quencher moiety. In such embodiments, the fluorescent moiety can be any fluorescent moiety known to one of skill in the art, as described above. Further, the quencher moiety can be any quencher moiety known to one of skill in the art without limitation. In certain embodiments, the quencher moiety can be selected from the group consisting of fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, and non-fluorescent quencher moieties. In certain embodiments, the non-fluorescent quencher moieties can be BHQ™-family dyes, Iowa Black™, or Dabcyl (Integrated DNA Technologies, Inc.). Other examples of specific quencher moieties include, for example, but not by way of limitation, TAMRA (N,N,N',N'-tetramethyl-6-carboxyrhodamine) (Molecular Probes, Inc.), DABCYL (4-(4'-dimehtylaminophenylazo)benzoic acid), Iowa Black™ (Integrated DNA Technologies, Inc.), Cy3™ (Integrated DNA Technologies, Inc.) or Cy5™ (Integrated DNA Technologies, Inc.). In a preferred embodiment, the quencher moiety is Cy5™. Other examples of quencher moieties that can be used in the probes, methods, and kits of the invention can be found in U.S. Pat. Nos. 6,399,392, 6,348,596, 6,080,068, and 5,707,813, each of which is hereby incorporated by reference in its entirety.

In certain embodiments, the quencher moiety can be attached to the 3' end of the probe. In other embodiments, the quencher moiety can be attached to the probe at a residue that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, about 35, about 40 or other number of residues from the 5' end of the probe. In a preferred embodiment, the fluorescent moiety is attached to the 5' end of the probe and the quencher moiety is attached to a residue that is within about 9 residues of the 5' end of the probe. The quencher moiety can be attached to any portion of a residue of the probe. For example, the quencher moiety can be attached to a sugar, phosphate, or base moiety of a nucleotide in the probe. In other embodiments, the quencher moiety can be attached between two residues of the probe.

While not intending to be bound to any particular theory or mechanism of action, it is believed that when the probe is intact, a photon emitted by the fluorescent moiety can be absorbed and thus quenched by the quencher moiety. The quencher moiety then either releases the energy of the photon as a photon of different wavelength or as heat. Thus, the quencher moiety can also be a fluorescent moiety. As described above, this phenomenon is termed fluorescence resonance energy transfer ("FRET"). Cleaving the probe between the fluorescent moiety and quencher results in a reduction in quenching of the fluorescent moiety's emitted fluorescence by the quencher moiety.

Generally, transfer of energy between the fluorescent moiety and the quencher moiety depends on the distance between the fluorescent moiety and the quencher moiety and the critical transfer distance of the particular fluorescent moiety-quencher moiety pair. The critical transfer distance is both characteristic and constant for a given fluorescent moiety paired with a given quencher moiety. Further, the spatial relationship of the fluorescent moiety in reference to the quencher moiety can be more sensitively determined when the critical transfer distance of the fluorescent moiety-quencher moiety pair is close to the distance between the fluorescent moiety and the quencher moiety. Accordingly, the skilled practitioner can select the fluorescent moiety and the quencher moiety to have a critical transfer distance that is close to the distance separating the fluorescent moiety from the quencher moiety on the probe. Critical transfer distances of particular fluorescent moiety-quencher moiety pairs are well known in the art and can be found, for example, in an article by Wu and Brand, *Anal. Biochem.* 218:1-13 (1994).

Other criteria for section of particular fluorescent moiety-quencher moiety pairs include, for example, the quantum yield of fluorescent emission by the fluorescent moiety; the wavelength of fluorescence emitted by the fluorescent moiety; the extinction coefficient of the quencher moiety; the wavelength of fluorescence, if any, emitted by the quencher moiety; and the quantum yield of fluorescent emission, if any, by the quencher moiety. In addition, if the quencher moiety is also a fluorescent moiety, the quencher moiety and the fluorescent moiety can be selected so that fluorescence emitted by one can easily be distinguished from fluorescence emitted by the other. Further guidance on the selection of particular fluorescent moiety-quencher moiety pairs may be found in a review article by Klostermeier and Millar, *Biopolymers* 61:159-179 (2002) y.

Exemplary combinations of fluorescent moieties and quencher moieties that can be used in this aspect of the invention include, but are not limited to the fluorescent moiety rhodamine 590 and the quencher moiety crystal violet. A preferred combination of fluorescent and quencher moieties is the fluorescent moiety 6-carboxyfluorescein and the quencher moiety Cy5™. Other examples of fluorescent moiety-quencher moiety pairs that can be used in the probes, methods, and kits of the invention can be found in U.S. Pat. No. 6,245,514.

Examples of molecules that can be used as both fluorescent or quencher moieties in FRET include fluorescein, 6-carboxyfluorescein, 2'7'-dimethoxy-4'5'-dichloro-6-carboxyfluorescein, rhodamine, 6-carboxyrhodamine, 6-carboxy-X-rhodamine, and 5-(2'-aminoethyl)aminonaphthalene-1-sulfonic acid (EDANS). Whether a fluorescent moiety is a donor or an acceptor is defined by its excitation and emission spectra, and the fluorescent moiety with which it is paired. For example, FAM™ is most efficiently excited by light with a wavelength of 488 nm, and emits light with a spectrum of 500 to 650 nm, and an emission maximum of 525 nm. Accordingly, FAM™ is a suitable fluorescent moiety for use with, for example, with TAMRA as quencher moiety, which has at its excitation maximum 514 nm.

2. Hybridization-Based Assays

Methods of detecting and/or quantifying the level of SENP1 or telomerase polynucleotides (RNA or cDNA made therefrom) using nucleic acid hybridization techniques are known to those of skill in the art (see, Sambrook et al., (1989) *Molecular Cloning: A Laboratory Manual,* 2d Ed., vols 1-3, Cold Spring Harbor Press, New York). Biological samples can be screened using a SENP1 or telomerase-specific probe. Such probes correspond in sequence to a region of the SENP1 or telomerase RNA, or their complement. Under defined conditions, specific hybridization of such a probe to test nucleic acid is indicative of the presence of the SENP1 or telomerase polynucleotide in a sample. Defined conditions will be sufficient to allow for hybridization of the probe to its target without significantly hybridizing to other polynucleotides in a complex mixture (e.g. genomic DNA from a cell). If desired, more than one probe may be used on the same test sample. The probe may comprise as few as 8, 15, 20, 50 or 100 or other number of nucleotides of the SENP1 or telomerase RNA sequence or its complement or may comprise as many as 500, 1 kb or the entire RNA sequence or its complement. In some embodiments, the probe is between 12 and 100 nucleotides, or 16-50 nucleotides or 18-40 nucleotides long.

One method for evaluating the presence, absence, and/or quantity of SENP1 or telomerase polynucleotides involves a Northern blot: mRNA is isolated from a given biological sample, separated by electrophoresis and transferred from the gel to a solid suppor (e.g., a nitrocellulose membrane). Labeled SENP1 or telomerase probes are then hybridized to the membrane to identify and/or quantify the mRNA.

Expression of SENP1 or telomerase polynucleotides can also be analyzed by other techniques known in the art, e.g., dot blotting, in situ hybridization, RNase protection, probing DNA microchip arrays, and the like.

An alternate method that is quite useful when large numbers of different probes are to be used is a "reverse" dot blot format, in which the amplified sequence contains a label, and the probe is bound to the solid support. This format would be useful if the assay methods of the present invention were used as one of a battery of methods to be performed simultaneously on a sample. In this format, the unlabeled probes are bound to the membrane and exposed to the labeled sample under appropriately stringent hybridization conditions. Unhybridized labeled sample is then removed by washing under suitably stringent conditions, and the filter is then monitored for the presence of bound sequences.

Both the forward and reverse dot blot assays can be carried out conveniently in a microtiter plate; see U.S. patent application Ser. No. 07/695,072 and U.S. Pat. No. 5,232,829. The probes can be attached to bovine serum albumin (BSA), for example, which adheres to the microliter plate, thereby immobilizing the probe. Another example of a method of using a probe of the invention to detect a SENP1 or telomerase polynucleotide is described in U.S. Pat. No. 6,383,756, which provides a method for detecting a nucleic acid bound to a membrane.

In another example, a SENP1 or telomerase polynucleotide can be detected using branched-DNA-based methods. In such methods, a dendrimer monomer is constructed of two DNA strands that share a region of sequence complementarity located in the central portion of each strand. When the two strands anneal to form the monomer the resulting structure has a central double-stranded center bordered by four single-stranded ends. A dendrimer can be assembled from monomers by hybridization of the single stranded ends of the monomers to each other, while still leaving many single-stranded ends free. These free single-stranded ends can have the sequences of any of the primers or probes of the invention. A dendrimer can be detectably-labeled with any detectable moiety known to one of skill in the art without limitation, as described above in connection with the probes of the invention.

Dendrimers can then be used as a probe, in, for example, the "dot blot" assays described below. In addition, a dendrimer can be used as a probe in any method known to one of skill in the art in which the probe is directly detected. A probe is directly detected when the presence of the probe can be determined without any subsequent reaction or modification, such as a dot blot or Southern hybridization. Further guidance on the selection and use of dendrimers as probes may be found in U.S. Pat. No. 6,261,779 and in Nilsen et al., *J. Theoretical Biology* 187:273-284 (1997), Capaldi et al., *Nucleic. Acids Res.*, 28(7):21e (2000), Wang et al., *J. Am. Chem. Soc.* 120:8281-8282 (1998), and Wang et al., *Electroanalysis* 10(8):553-556 (1998).

B. Detection of SENP1 DNA

In some cases, it will be advantageous to detect and analyze genomic DNA encoding SENP1. For example, it can be useful to determine the structure and/or nucleotide sequence of a genomic sequence encoding SENP1 or comprising SENP1 regulatory sequences to identify mutations associated with cancer or other diseases. Similarly, SENP1 cDNA sequences can be analyzed and/or nucleotide sequenced.

In some cases, SENP1 genomic sequences are analyzed to identify polymorphisms (e.g., variants) between commonly occurring alleles and alleles associated with cancer. Types of molecular analyses include, but are not limited to: RFLP analysis, PCR-based analyses, SNP analyses, etc.

C. Detection and Quantification of SENP1 or Telomerase Polypeptides

In addition to the detection of SENP1 or telomerase polynucleotides, one can also use affinity assays such as immunoassays to detect SENP1 or telomerase polypeptides. Immunoassays will typically be used to quantify SENP1 or telomerase polypeptides in a sample. A general overview of the applicable technology can be found in Harlow & Lane, *Antibodies: A Laboratory Manual* (1988).

Methods of producing polyclonal and monoclonal antibodies that react specifically with SENP1 or telomerase polypeptides are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256: 495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

SENP1 and/or telomerase polypeptides may be used to produce antibodies specifically reactive with SENP1 or telomerase, respectively. For example, a recombinant SENP1 or an antigenic fragment thereof, is isolated and purified, e.g., following recombinant expression in eukaryotic or prokaryotic cells. The product is then injected into an animal capable of producing antibodies. Either monoclonal or polyclonal antibodies may be generated, for subsequent use in immunoassays to measure the protein.

Monoclonal antibodies and polyclonal sera can be collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-SENP1 or telomerase proteins, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

Once SENP1 and/or telomerase-specific antibodies are available, SENP1 or telomerase polypeptides can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

SENP1 and/or telomerase polypeptides can be detected and/or quantified using any of a number of well recognized immunological binding assays (see, e.g., U.S. Pat. Nos. 4,366,241; 4,376,110; 4,517,288; and 4,837,168). For a review of the general immunoassays, see *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the SENP1 or telomerase polypeptides or antigenic subsequence thereof). The antibody (e.g., anti-SENP1 or anti-telomerase) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled SENP1 or telomerase polypeptide or a labeled anti-SENP1 or anti-telomerase antibody. Alternatively, the labeling agent may be a third moiety, such a secondary antibody, that specifically binds to the antibody/SENP1 or antibody/telomerase complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Immunoassays for detecting SENP1 or telomerase polypeptides in samples may be either competitive or noncompetitive. Noncompetitive immunoassays are assays in which the amount of antigen is directly measured. In "sandwich" assays, for example, the anti-SENP1 or anti-telomerase antibodies can be bound directly to a solid substrate on which they are immobilized. These immobilized antibodies then capture SENP1 or telomerase polypeptides present in the test sample. The SENP1 or telomerase polypeptide thus immobilized is then bound by a labeling agent, such as a second anti-SENP1 or anti-telomerase antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

In competitive assays, the amount of SENP1 or telomerase polypeptide present in the sample is measured indirectly by measuring the amount of a known, added (exogenous) SENP1 or telomerase polypeptide displaced (competed away) from an anti-SENP1 or anti-telomerase antibody by the unknown SENP1 or telomerase polypeptide present in a sample. In one competitive assay, a known amount of SENP1 or telomerase polypeptide is added to a sample and the sample is then contacted with an antibody that specifically binds to the SENP1 or telomerase polypeptide. The amount of exogenous SENP1 or telomerase polypeptide bound to the antibody is inversely proportional to the concentration of SENP1 or telomerase polypeptide present in the sample. In some embodiments, the antibody is immobilized on a solid substrate. The amount of SENP1 or telomerase polypeptide bound to the antibody may be determined either by measuring the amount of SENP1 or telomerase polypeptide present in a SENP1/antibody or telomerase/antibody complex, or alternatively by measuring the amount of remaining uncomplexed protein.

Western blot (immunoblot) analysis can also be used to detect and quantify the presence of SENP1 or telomerase polypeptides in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind SENP1 or telomerase. The anti-SENP1 or anti-telomerase antibodies specifically bind to the SENP1 or telomerase on the solid support. These antibodies may be directly labeled or, alternatively, may be subsequently detected using labeled antibodies (e.g., labeled sheep anti-mouse antibodies) that specifically bind to the anti-SENP1 or anti-telomerase antibodies.

One of skill in the art will appreciate that it is often desirable to minimize non-specific binding in immunoassays. Particularly where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes, radiolabels, enzymes, and colorimetric labels such as colloidal gold or colored glass or plastic beads.

D. Detection and Quantification of SENP1 or Telomerase Activity

The quantity of SENP1 or telomerase can also be determined by detecting the activity of the proteins.

SENP1 is a protease that removes sentrins from proteins. See, e.g., U.S. Pat. No. 6,596,527; Gong et al., *J. Biol Chem.* 275(5):3355-3359 (2000); and Bailey et al., *J. Biol Chem.* 279(1):692-703 (2004). For instance, SENP1 activity can be detected by detecting removal of sentrins from a known amount of sentrinized protein in the sample.

Telomerase activity can be measured by any number of assays known in the art. See, e.g., Hiyama et al., *Cancer Lett.* 194(2):221-33 (2003). For example, TRAP (telomeric repeat amplification protocol) can be used for detecting telomerase activity with a high sensitivity by using PCR. See, Kim N. W. et al., *Science* 206:2011-2015 (1994); Piatyszek M. A. et al., *Meth. Cell Sci.*, 17:1-15 (1995); Woodring et al., *Nuc. Acids Res.* 23(18):3794-3795 (1995); U.S. Pat. Nos. 6,551,774; 6,391,554; and 5,837,453. This method involves the detection of telomerase by a single primer extension assay system and is roughly divided in three steps. First, telomerase is extracted from cells. Then, an extension reaction of a TTAGGG chain by the telomerase is carried out and the reaction products are amplified by PCR using two primers. Finally, the amplified products are electrophoresed to detect the telomerase activity by confirming ladders in autoradiography.

A variation of TRAP involves SYBR Green in real-time to quantify telomerase activity. See, e.g., Wege et al., *Nuc. Acids Res.* 31(2):e3 (2003).

Another variation of TRAP is called telomeric extension-PCR (PTEP). See, e.g., Chen et al., *Biotechniques* 35(1):158-62 (2003). Similar to TRAP, this method is based on PCR amplification following the in vitro telomerase reaction, while the in vitro telomerase reaction here is prematurely, rather than randomly, terminated. Apart from this, the telomeric extension products are used as initial primers, instead of as templates, to trigger the amplification with a specially constructed plasmid DNA as the template that cannot be directly amplified with the telomerase primer. The end product is a specific DNA fragment that reflects telomerase activity.

Those of skill in the art will recognize that other methods can also be used to detect telomerase activity. See, e.g., U.S. patent Publication No. 2002/0025518.

III. Quantification Standards for Assays of the Inventions

In many embodiments of the invention, the quantity of SENP1 or telomerase in a biological sample is compared to one or more standard values. In general, the standard value will represent the quantity of SENP1 or telomerase found in biological samples from a healthy individual (e.g., not diagnosed with cancer and/or not containing a significant number of cancer cells). Different standard values will be appropriate depending on a number of factors. For example, the quantity of SENP1 or telomerase in a sample from a healthy individual can vary depending on the method used for quantifying SENP1 or telomerase. Moreover, the standard value can vary depending on the proportion of false positives and false negatives that will be provided in a diagnostic assay. For example, if the standard value is set at a low value, the number of false negatives will decrease but the proportion of false positives (those without cancer that are scored as having cancer cells) will increase. Thus, a user can compare SENP1 or telomerase quantity in a sample to different standard values depending on the tolerance for false negative or false positive results.

In some cases, the standard value will be determined based on the average, median, or other statistical calculation based on a plurality of samples either known to lack cancer cells or known to contain cancer cells. The standard value need not be recalculated for each assay, but can be a pre-determined single value or range. The standard value can be stored in a computer memory and accessed as necessary.

In other embodiments, the standard value is determined for each biological sample each time a set of biological samples are processed. In these cases, the standard value is the quantity of SENP1 or telomerase in a sample known, or at least suspected, to not contain cancer cells. In some embodiments, these standard samples will be collected from the same individual as is tested for cancer. For example, a solid tumor and a non-cancer-containing sample can be obtained from the same individual and the quantity of SENP1 and/or telomerase in the non-cancer-containing sample can form the basis of the standard value. In other embodiments, the standard samples will be obtained from another individual or individuals.

In some cases, the quantities of SENP1 or telomerase (both from the biological sample of interest and the non-cancer standard) are normalized to a second value. Normalization is useful, for example, to remove or minimize error introduced by a user or assays into the amounts detected or to minimize error caused by varying numbers of cells in a sample. Normalization is typically based on a value that incorporates some of the same errors. For example, the quantity of a second transcript in the same biological sample can be used to normalize SENP1 or telomerase values. Typically, the second transcript is known or suspected not to be effected by the presence or absence of cancer cells in the sample. Exemplary "normalizing transcripts" (also known as transcripts of "housekeeping genes") include, but are not limited to, the following human proteins: protein phosphatase 1, catalytic subunit, alpha isoform (PPP1CA), TATA box binding protein (e.g., M55654), HPRT1 (e.g., M26434), β-glucuronidase, β2-microglobulin, phosphoglycerol kinase 1 (e.g., NM_000291), β-actin (e.g., NM_001101), transferrin receptor (e.g., NM_003234), glyceraldehyde-3-phosphate dehydrogenase (e.g., NM_002046), human serum albumin (e.g., NM_000477), tubulin, hypoxantine phosphoribosyl-transferase (e.g., NM_000194), mitochondrial ribosomal protein L32 (e.g., NM_031903), 28S RNA, 18S RNA, 5-aminolevulinate synthase, and porphobilinogen deaminase. See also, LightCycler h-Housekeeping Gene Selection Set (Roche Applied Sciences, catalog no. 3310159); Thellin, O. et al., *J. Biotechnol.* 75:291 (1999); Warrington, J. A. et al., *Physiol. Genomics* 2:143 (2000). Those of skill in the art will recognize that many house keeping genes, among others, will provide equivalent normalizing values. Values can be normalized according to any generally known statistical methods, including by simply dividing values by the quantity of the normalizing transcript or protein.

IV. Recording a Diagnosis, Prognosis or Stage of Cancer

The methods of the invention may involve recording the quantity of SENP1 and/or telomerase in a sample and/or a diagnosis, prognosis, or stage of cancer, including, e.g., bladder cancer, breast cancer, colon cancer, kidney cancer, lung cancer, ovarian cancer, pancreatic cancer, and small intestine cancer.

This information may be recorded as text or data and may be stored in a computer readable form. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system also be linked to a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of quantification of SENP1 or telomerase in a biological sample. Thus in an exemplary embodiment, the genotype results are provided to a computer where a central processor is executes a computer program for determining a diagnosis, prognosis or determination of the stage of a particular cancer, e.g., selected from bladder cancer, breast cancer, colon cancer, kidney cancer, lung cancer, ovarian cancer, pancreatic cancer, and small intestine cancer.

V. Diagnosing Cancer

The present methods can be used in the diagnosis, prognosis, classification, and treatment of a number of types of cancers. A cancer at any stage of progression can be detected, such as primary, metastatic, and recurrent cancers. Information regarding numerous types of cancer can be found, e.g., from the American Cancer Society (world wide web at cancer.org), or from, e.g., Wilson et al. (1991) *Harrison's Principles of Internal Medicine*, 12th Edition, McGraw-Hill, Inc. Exemplary cancers that can be detected include, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, and non-Hodgkin's lymphoma. See, CANCER: PRINCIPLES AND PRACTICE (DeVita, V. T. et al. eds 1997) for additional cancers.

The present invention provides methods for determining whether or not a mammal (e.g., a human) has cancer, whether or not a biological sample contains cancerous cells, estimating the likelihood of a mammal developing cancer, and monitoring the efficacy of anti-cancer treatment in a mammal with cancer. Such methods are based on the discovery that cancer cells have an elevated level of SENP1 polynucleotide and/or polypeptide. Accordingly, by determining whether or not a cell contains elevated levels of SENP1 or telomerase, it is possible to determine whether or not the cell is cancerous. Further, the presence of cancerous cells can be determined indirectly, e.g., in certain embodiments a biological sample that does not itself contain cancerous cells, but which has been taken from an animal with cancerous cells elsewhere in its body, may contain elevated levels of SENP1 or telomerase reflecting the presence of the cancerous cells.

In numerous embodiments of the present invention, the level and/or presence of SENP1 or telomerase will be detected in a biological sample, thereby detecting the presence or absence of cancerous cells in the biological sample, or, in certain embodiments, in the mammal from which the biological sample was removed. In some embodiments, the biological sample will comprise a tissue sample from a tissue suspected of containing cancerous cells. For example, in an individual suspected of having bladder cancer, bladder tissue is biopsied, or urine is obtained. In other embodiments, the quantity of SENP1 or telomerase is determined in a bodily fluid (e.g., urine sediment (see, e.g., Melissourgos et al., *Urology* 62(2):362-7 (2003)), saliva, blood, semen, etc.). In some embodiments, the quantity of SENP1 in a biopsy from a tissue selected from breast, colon, kidney, lung, ovarian, pancreatic, and small intestine is used to detect cancer in that tissue. In some embodiments, the quantity of SENP1 in a bronchial lavage is determined, e.g., to diagnose lung cancer. In some embodiments, the quantity of SENP1 is determined from a stool sample, e.g., to diagnose colon or small intestine cancer. In other embodiments, a tissue sample known to contain cancerous cells, e.g., from a tumor, will be analyzed for SENP1 or telomerase levels to determine information about the cancer, e.g., the efficacy of certain treatments, the survival expectancy of the animal, etc. Often, the methods will be used in conjunction with additional diagnostic methods, e.g., detection of other cancer markers, etc.

Further, the present methods may be used to assess the efficacy of a course of treatment. For example, in a mammal with cancer from which a biological sample has been found to contain an elevated amount of a SENP1 or telomerase, the efficacy of an anti-cancer treatment can be assessed by monitoring SENP1 or telomerase levels over time. For example, a reduction in SENP1 or telomerase levels in a biological sample taken from a mammal following a treatment, compared to a level in a sample taken from the mammal before, or earlier in, the treatment, indicates efficacious treatment.

The methods detecting cancer can comprise the detection of one or more other cancer-associated polynucleotide or polypeptides sequences. Accordingly, SENP1 or telomerase can be used either alone, together or in combination with other markers for the diagnosis or prognosis of cancer.

The methods of the present invention can be used to determine the optimal course of treatment in a mammal with cancer. For example, the presence of an elevated level of SENP1 or telomerase can indicate a reduced survival expectancy of a mammal with cancer, thereby indicating a more aggressive treatment for the mammal. In addition, a correlation can be readily established between levels of SENP1 or telomerase, or the presence or absence of a diagnostic presence of SENP1 or telomerase (i.e., a quantity of SENP1 or telomerase over the standard value), and the relative efficacy of one or another anti-cancer agent. Such analyses can be performed, e.g., retrospectively, i.e., by detecting SENP1 or telomerase levels in samples taken previously from mammals that have subsequently undergone one or more types of anti-cancer therapy, and correlating the SENP1 or telomerase levels with the known efficacy of the treatment.

In making a diagnosis, prognosis, risk assessment or classification, based on expression of SENP1 and/or telomerase, the quantity of SENP1 and/or telomerase expression may be compared to a standard value, as discussed above. In some cases, a diagnosis or prognosis of cancer can be made if SENP1 and/or telomerase expression in the biological sample is higher than the standard value. In some cases, the quantity of SENP1 and/or telomerase expression in the biological sample is at least 10% more, 25% more, 50% more, 75% more, 90% more, 2-fold, 3-fold, 5-fold, 10-fold, 50-fold, or more than 100-fold compared to the standard value (or a value representing SENP1 and/or telomerase expression in a non-cancer containing sample).

VI Sample Preparation and Nucleic Acid Amplification

Samples are generally derived or isolated from subjects, typically mammalian subjects, more typically human subjects. Essentially any technique for acquiring these samples is optionally utilized including, e.g., biopsy, scraping, venipuncture, swabbing, or other techniques known in the art.

Methods of storing specimens, culturing cells, isolating and preparing nucleic acids from these sources are generally known in the art and many of these are described further in the references and/or examples provided herein.

To further illustrate, prior to analyzing the target nucleic acids described herein, those nucleic acids may be purified or isolated from samples that typically include complex mixtures of different components. Cells in collected samples are typically lysed to release the cell contents. For example, cells in urine sediment can be lysed by contacting them with various enzymes, chemicals, and/or lysed by other approaches known in the art. In some embodiments, nucleic acids are analyzed directly in the cell lysate. In other embodiments, nucleic acids are further purified or extracted from cell lysates prior to detection. Essentially any nucleic acid extraction methods can be used to purify nucleic acids in the samples utilized in the methods of the present invention. Exemplary techniques that can be used to purifying nucleic acids include, e.g., affinity chromatography, hybridization to probes immobilized on solid supports, liquid-liquid extraction (e.g., phenol-chloroform extraction, etc.), precipitation (e.g., using ethanol, etc.), extraction with filter paper, extraction with micelle-forming reagents (e.g., cetyl-trimethyl-ammonium-bromide, etc.), binding to immobilized intercalating dyes (e.g., ethidium bromide, acridine, etc.), adsorption to silica gel or diatomic earths, adsorption to magnetic glass particles or organo silane particles under chaotropic conditions, and/or the like. Sample processing is also described in, e.g., U.S. Pat. Nos. 5,155,018, 6,383,393, and 5,234,809.

To further exemplify, unmodified nucleic acids can bind to a material with a silica surface. Many of the processes that are optionally adapted for use in performing the methods of the present invention are described in the art. To illustrate, Vogelstein et al. (1979) *Proc. Natl. Acad. Sci. USA* 76:615-619 describes the purification of nucleic acids from agarose gels in the presence of sodium iodide using ground flint glass. Marko et al. (1982) *Anal. Biochem.* 121:382-387 describes the purification of nucleic acids from bacteria on glass dust in the presence of sodium perchlorate. In DE-A 3734442 nucleic acids are isolated on glass fiber filters. The nucleic acids bound to these glass fiber filters are washed and then eluted with a methanol-containing Tris/EDTA buffer. A similar procedure is described in Jakobi et al. (1988) *Anal. Biochem.* 175:196-201. In particular, Jakobi et al. describes the selective binding of nucleic acids to glass surfaces in chaotropic salt solutions and separating the nucleic acids from contaminants, such as agarose, proteins, and cell residue. To separate the glass particles from the contaminants, the particles can be centrifuged or fluids can be drawn through the glass fiber filters. In addition, the use of magnetic particles to immobilize nucleic acids after precipitation by adding salt and ethanol is described in, e.g., Alderton et al. (1992) *Anal. Biochem.* 201:166-169 and PCT/GB91/00212. In this procedure, the nucleic acids are agglutinated along with the magnetic particles. The agglutinate is separated from the original solvent by applying a magnetic field and performing one or more washing steps. After at least one wash step, the nucleic acids are typically dissolved in a Tris buffer.

Magnetic particles in a porous glass matrix that is covered with a layer that includes, e.g., streptavidin can also be utilized in certain embodiments of the invention. These particles can be used, e.g., to isolate biotin-conjugated nucleic acids and proteins. Ferrimagnetic, ferromagnetic, and superparamagnetic particles are also optionally utilized. Magnetic glass particles and related methods that can be adapted for using in performing the methods described herein are also described in, e.g., WO 01/37291.

VII. Kits

The present invention also provides for kits for diagnosing cancer by detecting SENP1 and telomerase (e.g., polynucleotides, polypeptides, or activity). The kits of the invention will generally comprise reagents for detecting SENP1 and/or telomerase polypeptides and/or SENP1 and/or telomerase polynucleotides, and will optionally contain written instructions for their use.

In some embodiments, the kits of the invention will comprise reagents to amplify SENP1 and/or telomerase polynucleotides. Such reagents can include, e.g., SENP1 and/or telomerase-specific primers and/or detectably labeled probes (e.g., 5' exonuclease, molecular beacon or Scorpion probes). The kits can optionally include amplification reagents such as thermostable polymerases, reverse transcriptase, nucleotides, buffers and salts or other components as described herein or known in the art.

In some cases, the kits will comprise at least one oligonucleotide comprising a sequence at least 70%, 75%, 80%, 85%, 90% or 95% identical to at least 5, 6, 7, 8, 9, 10, 11, 12, 13, 14, 15, 16, 17, 18, 19, 20, 25, 35, 50 or more contiguous nucleotides of SEQ ID NO:1, or a complement thereof, such that when the oligonucleotide and a polynucleotide comprising SEQ ID NO:1 are submitted to an amplification reaction, the oligonucleotide primes amplification of at least a fragment of SEQ ID NO:1.

In some cases, the kits will also comprise the detectably-labeled oligonucleotide comprising a sequence at least 70%, 75%, 80%, 85%, 90% or 95% identical to at least 5, 6, 7, 8, 9, 10, 11, 12, 13, 14, 15, 16, 17, 18, 19, 20, 25, 35, 50 or more contiguous nucleotides of SEQ ID NO:1, or a complement thereof.

In some cases, the kits will comprise at least one oligonucleotide comprising a sequence at least 70%, 75%, 80%, 85%, 90% or 95% identical to at least 5, 6, 7, 8, 9, 10, 11, 12, 13, 14, 15, 16, 17, 18, 19, 20, 25, 35, 50 or more contiguous nucleotides of:

i) human telomerase RNA (TERC);
ii) human telomerase reverse transcriptase protein (TERT) mRNA;
iii) a complement of TERC; or
iv) a complement of TERT such that when the oligonucleotide and TERC or TERT mRNA are submitted to an amplification reaction, the oligonucleotide primes amplification of at least a fragment of TERC or TERT mRNA.

In some cases, the kits will comprise the detectably-labeled oligonucleotide comprising a sequence at least 70%, 75%, 80%, 85%, 90% or 95% identical to at least 5, 6, 7, 8, 9, 10, 11, 12, 13, 14, 15, 16, 17, 18, 19, 20, 25, 35, 50 or more contiguous nucleotides of:

i) human telomerase RNA (TERC);
ii) human telomerase reverse transcriptase protein (TERT) mRNA;
iii) a complement of TERC; or
iv) a complement of TERT.

In other embodiments, the kits of the invention comprise reagents that specifically bind to SENP1 or telomerase polypeptides. For example, in some embodiments, the kits of the invention comprise a first antibody that specifically binds to SENP1 or telomerase. The kits can also comprise a second antibody that binds to the first antibody (i.e., from a different species) and a detectable label.

VIII. Screening for Antagonists of SENP1

A number of different screening protocols can be utilized to identify agents that modulate the level of activity of SENP1 in cells, e.g., in mammalian cells, e.g., in human cells. In general terms, the screening methods may involve screening a plurality of agents to identify an agent that interacts with SENP1, for example, by binding to SENP1 and preventing activity of SENP1 or by preventing an activator of SENP1 from activating SENP1.

1. SENP1 Binding Assays

Preliminary screens can be conducted by screening for agents capable of binding to SENP1, as at least some of the agents so identified may be SENP1 antagonists. The binding assays usually involve contacting aSENP1 protein with one or more test agents and allowing sufficient time for the protein and test agents to form a binding complex. Any binding complexes formed can be detected using any of a number of established analytical techniques. Protein binding assays include, but are not limited to, immunohistochemical binding assays, flow cytometry or other assays which maintain conformation of SENP1. SENP1 utilized in such assays can be naturally expressed, cloned or synthesized.

Binding assays are also useful, e.g., for identifying endogenous proteins that interact with SENP1.

2. Cells and Reagents

The screening methods of the invention can be performed as in vitro or cell-based assays. Cell-based assays can be performed in any cells in which a SENP1 polypeptide is endogenously or exogenously expressed. In some embodiments, the cell-based assays may be performed using cells that have reduced or no detectable telomerase activity or expression and/or that have a neoplastic phenotype. In some embodiments, TERT expression-negative immortal cell lines are tested for susceptibility to potential SENP1 inhibitors. These telomerase-negative cell lines are proposed to be useful in such a screen since they likely replicate their telomeres by a telomerase-independent mechanism (Alternative Lengthening of Telomeres or "ALT"). Without intending to limit the scope of the invention to a particular mechanism of action, we propose that SENP1 is involved in the maintenance of ALT. Inhibition of ALT by a SENP1 inhibitor would then be predicted to result in an alteration of the telomere structure with an eventual inhibition of division of these cells. In contrast, in cases where telomerase is active in cell-lines, the telomerase would continue to allow for cell division even in the presence of a SENP1 inhibitor.

Examples of cells that do not express telomerase ("ALT" cells) are known in the literature. See, e.g., Tsutsui, T et al. *Carcinogenesis* 24:953-65 (2003); Bryan, T M., *Hum Mol*

*Genet* 6:921-6 (1997); Guilleret, I et al., *Carcinogenesis* 23:2025-2030 (2002). Examples of ALT cell lines include, but are not limited to, SUSM-1, WI38 VA13/2RA, BET-3M, GM847, MeT-4A, IIICF/c, IIICF-T/A6, MDAH 087, Saos-2 and U-2 cells.

Inhibition of ALT can be detected by assaying for a change in telomere length (see, e.g., the TeloTAGGG Telomere Length Assay from Roche Applied Biosystems or Tsutsui, T et al *Carcinogenesis* 24:953-965 (2003)), or a change in morphological markers such as the presence of PML bodies that are "donut-shaped" in ALT cells instead of the normally punctate appearance of PML-NB in cells not undergoing ALT (see, e.g., Yeager T R, et al., *Cancer Res.* 59:4175-4179 (1999), inhibition of cell division (determined by, e.g., counting the number of cells at different time points (e.g., using Guava Technology™ products), using soft agar based assays to count the number of colonies at different time points, using cell staging technology to determine the stage of the cell cycle the cells are in, visually analyzing cell using microscopy, chromosomal analyses or Cellomics™ technology, or analyzing protein expression, e.g., via western blotting or immunohistochemical analyses).

Cell-based assays may involve whole cells or cell fractions containing SENP1 to screen for agent binding or modulation of SENP1 activity by the agent. Cells used in the cell-based assays may be primary cells or tumor cells or other types of immortal cell lines. Of course, SENP1 can be expressed in cells that do not endogenously express SENP1.

3. Signaling Activity or Downstream Events

Signaling activity or other downstream events regulated by SENP1 can also be monitored to identify SENP1 antagonists. Thus, in some embodiments, a plurality of agents are contacted to a cell expressing SENP1 and the cells are subsequently screened for a change in signaling or a downstream event. The pool of agents that modulate a downstream event regulated by SENP1 are typically enriched for SENP1 antagonists because at least some of the identified agents are likely to directly antagonize SENP1. Downstream events include those activities or manifestations that occur as a result of inhibition of SENP1, and may include, e.g.: reduced cell growth (measured, e.g., as colony counts in soft agar or using cell analysis systems such as those from Guava Technologies, Hayward, Calif.), changes in cell cycle stage (measured, e.g., using HT antibody staining image analysis, e.g., from Cellomics, Pittsburgh, Pa., or by standard cytological methods); or changes in protein expression, including, e.g., by western blotting or microscopy.

Soft Agar Growth or Colony Formation in Suspension

Normal cells require a solid substrate to attach and grow. Neoplastic cells have lost this phenotype and grow detached from the substrate. For example, neoplastic cells can grow in stirred suspension culture or suspended in semi-solid media, such as semi-solid or soft agar. The neoplastic cells, when transfected with tumor suppressor genes or when contacted with a SENP1 antagonist, may regenerate normal phenotype and may require a solid substrate to attach and grow. Thus, soft agar growth or colony formation in suspension assays can be used to identify agents that reduce or eliminate abnormal cellular proliferation and transformation, including soft agar growth.

Techniques for soft agar growth or colony formation in suspension assays are described in Freshney, *Culture of Animal Cells a Manual of Basic Technique* (3$^{rd}$ ed., 1994), herein incorporated by reference.

Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with ($^3$H)-thymidine at saturation density can be used to measure density limitation of growth. See Freshney (1994), supra. The transformed cells, when transfected with tumor suppressor genes, regenerate a normal phenotype and become contact inhibited and would grow to a lower density.

Labeling index with ($^3$H)-thymidine at saturation density may be used to measure density limitation of growth. For example, transformed host cells may be contacted with a candidate SENP1 antagonist and then grown for a period of time (e.g., 24 hours) to saturation density in non-limiting medium conditions. The percentage of cells labeling with ($^3$H)-thymidine may be determined autoradiographically. See, Freshney (1994), supra.

Growth Factor or Serum Dependence

Transformed cells have a lower serum dependence than their normal counterparts (see, e.g., Temin, *J. Natl. Cancer Insti.* 37:167-175 (1966); Eagle et al., *J. Exp. Med.* 131:836-879 (1970)); Freshney, supra. This is in part due to release of various growth factors by the transformed cells. Growth factor or serum dependence of cells contacted with a candidate SENP1 antagonist can be compared with that of control.

Tumor Specific Markers Levels

Tumor or neoplastic cells release an increased amount of certain factors (hereinafter "tumor specific markers") than their normal counterparts. For example, plasminogen activator (PA) is released from human glioma at a higher level than from normal brain cells (see, e.g., Gullino, *Angiogenesis, tumor vascularization, and potential interference with tumor growth*. in *Biological Responses in Cancer*, pp. 178-184 (Mihich (ed.) 1985)). Similarly, Tumor angiogenesis factor (TAF) is released at a higher level in tumor cells than their normal counterparts. See, e.g., Folkman, *Angiogenesis and Cancer, Sem Cancer Biol.* (1992)).

Various techniques which measure the release of these factors are described in Freshney (1994), supra. Also, see, Unkless et al., *J. Biol. Chem.* 249:4295-4305 (1974); Strickland & Beers, *J. Biol. Chem.* 251:5694-5702 (1976); Whur et al., Br. *J. Cancer* 42:305-312 (1980); Gullino, *Angiogenesis, tumor vascularization, and potential interference with tumor growth*. in *Biological Responses in Cancer*, pp. 178-184 (Mihich (ed.) 1985); Freshney *Anticancer Res.* 5:111-130 (1985).

Invasiveness into Matrigel

The degree of invasiveness into Matrigel or some other extracellular matrix constituent can be used in an assay to identify SENP1 antagonists. Tumor cells exhibit a good correlation between malignancy and invasiveness of cells into Matrigel or some other extracellular matrix constituent. In this assay, neoplastic cells may be used, wherein a decrease invasiveness of the cells following contacted with an agent may indicate that the agent is a SENP1 antagonist.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

4. Validation

Agents that are initially identified by any of the foregoing screening methods can be further tested to validate the apparent activity. In some embodiments, such studies are conducted with suitable animal models. The basic format of such methods involves administering a lead compound identified during an initial screen to an animal that serves as a model for human disease to be treated and then determining if SENP1 is in fact modulated and/or the disease or condition is ameliorated. The animal models utilized in validation studies generally are mammals of any kind. Specific examples of suitable animals include, but are not limited to, primates, mice and rats.

5. Agents that Interact with SENP1

The agents tested as modulators of SENP1 can be any small chemical compound, or a biological entity, such as a polypeptide (e.g., a peptide), sugar, nucleic acid (including, e.g., siRNAs or antisense polynucleotides) or lipid. Essentially any chemical compound can be used as a potential modulator (e.g., antagonist) or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, the agents have a molecular weight of less than 1,500 daltons, and in some cases less than 1,000, 800, 600, 500, or 400 daltons. The relatively small size of the agents can be desirable because smaller molecules have a higher likelihood of having physiochemical properties compatible with good pharmacokinetic characteristics, including oral absorption than agents with higher molecular weight. For example, agents less likely to be successful as drugs based on permeability and solubility were described by Lipinski et al. as follows: having more than 5 H-bond donors (expressed as the sum of OHs and NHs); having a molecular weight over 500; having a LogP over 5 (or MLogP over 4.15); and/or having more than 10 H-bond acceptors (expressed as the sum of Ns and Os). See, e.g., Lipinski et al. *Adv Drug Delivery Res* 23:3-25 (1997).

In some embodiments, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C & E N, Jan. 18, 1993 page 33; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

SENP1 is structurally related to the ubiquitin family of proteins and this similarity can be used to assist in designing SENP1 antagonists. The family of Small Ubiquitin-Like (Ubl) Modifiers (SUMO; reviewed in Muller, S., et al., *Nat Rev Mol Cell Biol* 2(3):202-10 (2001) and Yeh, E. T., et al., *Gene* 248(1-2):1-14 (2000)), of which SENP1 is a member, is related to the Ubiquitin family. Although sequence identity between the two families is <20%, the overall structures are very similar (2.1 Å rmsd for core residues [21-93 and 1-72 of SUMO-1 and ubiquitin, respectively] (Bayer, P., et al., *J. Mol Biol.* 280(2):275-86 (1998))). Both proteins become covalently attached via their C-terminal —COOH group to the $\epsilon$-$NH_2$ group of a Lysine side chain (isopeptide bond) of the target protein. Ubiquitin and SUMO possess conserved di-Glycine motifs near the C-terminus. The conjugation of Ubiquitin and SUMO is a complex process that involves several steps: C-tail cleavage, activation and final transfer (Johnson, E. S., et al., *Embo J* 16(18):5509-19 (1997); Gong, L., et al., *FEBS Lett* 448(1):185-9 (1999)).

Unlike ubiquitin, SUMOs do not form polymeric attachments due to substitution of the equivalent to Ubiquitin Lys-48 with Gln. The SUMO and ubiquitin pathways differ primarily in the consequence of the modification: the most well characterized result of ubiquitination is the targeting of the tagged protein to the 26 S proteasome for degradation. SUMOylated proteins are not destined for degradation.

Three SUMO genes have been identified in humans (see Table 1 for accession numbers). There is 62.0/49.0% sequence similarity/identity between Smt3 and human SUMO-1 (see Table 2). The solution structure for human SUMO-1 has been solved (Bayer, P., et al., *J Mol Biol.* 280 (2):275-86 (1998)).

TABLE 1

Sequences (SWISSPROT accession numbers), Pfam motifs and Structures (PDB files).

| Sequence/Motif/Structure | Description |
| --- | --- |
| YEASTGP:ULP1 | *S. cerevisiae* Ulp1 |
| YEASTGP:ULP2 | *S. cerevisiae* Ulp1 |
| SW_HUM:SEN1_HUMAN | *H. sapiens* SENP1 |
| SW_HUM:SEN2_HUMAN | *H. sapiens* SENP2 |
| SW_HUM:SEN3_HUMAN | *H. sapiens* SENP3 |
| SW_HUM:SEN5_HUMAN | *H. sapiens* SENP5 |
| SW_HUM:SEN6_HUMAN | *H. sapiens* SENP6 |
| SW_HUM:SEN7_HUMAN | *H. sapiens* SENP7 |
| SW_HUM:SEN8_HUMAN | *H. sapiens* SENP8 |
| PF02902 | Pfam Ulp1_C (SENP family) |
| 1euv.pdb | Yeast Ulp1-Smt3 X-ray structure |

TABLE 1-continued

Sequences (SWISSPROT accession numbers), Pfam motifs and Structures (PDB files).

| Sequence/Motif/Structure | Description |
| --- | --- |
| PF00443 | Pfam Ubiquitin carboxyl-terminal hydrolase (UCH family) |
| SW_HUM:UBL3_HUMAN (P15374) | *H. sapiens* Ubiquitin carboxyl-terminal hydrolase isozyme L3 |
| SW_HUM:UBL1_HUMAN (P09936) | *H. sapiens* Ubiquitin carboxyl-terminal hydrolase isozyme L1 |
| SW_HUM:UBL5_HUMAN (Q9y5k5) | *H. sapiens* Ubiquitin carboxyl-terminal hydrolase isozyme L5 |
| 1uch.pdb | *H. sapiens* UCH-L3 X-ray structure |
| 1cmx.pdb | Yeast UCH-ubiquitin aldehyde X-ray structure |
| SW_HUM:SM33_HUMAN | *H. sapiens* SUMO-1 |
| SW_HUM:SM32_HUMAN | *H. sapiens* SUMO-? (Sentrin 2) |
| SW_HUM:SM31_HUMAN | *H. sapiens* SUMO-? |
| YEASTGP:SMT3 | *S. cerevisiae* Smt3 |
| SW_HUM:UBIQ_HUMAN | *H. sapiens* Ubiquitin |
| PF00240 | Pfam Ubiquitin family |
| 1a5r.pdb | NMR Structure of *H. sapiens* SUMO-1 (Sm33) |

TABLE 2

Sequence Similarity/Identity Matrix for *H. sapiens* Sm (SUMO) and *S. cerevisiae* Smt3. e.g.: Sm31 and Sm32 have 98.94% similarity and 96.81% identity.

| | sm31_human | sm32_human | sm33_human | 1a5r | 1euv | ubiq_human | |
| --- | --- | --- | --- | --- | --- | --- | --- |
| sm31_human | | 96.81 | 48.96 | 48.96 | 48.10 | 15.79 | 3 gaps |
| sm32_human | 98.94 | | 50.00 | 50.00 | 46.84 | 15.79 | 3 gaps |
| sm33_human | 65.62 | 64.89 | | 100.00 | 50.63 | 18.42 | 3 gaps |
| 1a5r | 65.62 | 64.89 | 100.00 | | 50.63 | 18.42 | 2 gaps |
| 1euv | 62.03 | 63.29 | 65.82 | 65.82 | | 13.33 | 4 gaps |
| ubiq_human | 39.47 | 39.47 | 42.11 | 42.11 | 37.33 | | 2 gaps |

SUMOylation is a dynamic, reversible process. The cleavage of SUMO from its target (deSUMOylation) is catalyzed by cysteine proteases termed ULP (for Ubiquitin-like proteases) in yeast and SENPs or SUSPs in human (for sentrin/SUMO-specific proteases) (Li, S. J. and M. Hochstrasser, *Nature* 398(6724):246-51 (1999); Bailey, D. and P. O'Hare, *J Biol Chem* 279(1):692-703 (2004)). Two ULPs have been identified in yeast (Ulp1 and Ulp2) and at least seven SENPs in human (see Table 1). These proteases play a dual role in the SUMOylation pathway: C-terminal tail processing to generate the di-Glycine motif and de-conjugation by hydrolysis of the Gly-Lys isopeptide bond. They do not cleave ubiquitin isopeptide bonds. In yeast, the deconjugating function of Ulp1 is essential (Li, S. J. and M. Hochstrasser, *Nature* 398 (6724):246-51 (1999)). It is reasonable to speculate that the various distinct SENPs in mammals have evolved to work with the distinct SUMO forms. Additionally, sub-cellular localization places a physiologically significant restraint on SUMO isopeptidase specificity. For example, SENP1 can deconjugate SUMO-1 from Ran GAP1 in vitro, but not in vivo. This is attributed to the fact that Ran GAP1 is attached to the cytoplasmic fibrils of the nuclear pore complex, while SENP1 is localized to the nucleus (Gong, L., et al., *J Biol Chem* 275(5): p. 3355-9 (2000)). A nuclear localization signal (NLS1) is found in SENP1 at position 171-177.

An alignment of the seven human SENP and two ULP sequences indicates that there is conservation among the core C-terminal catalytic domain (residues 420-643 in SENP1; see Table 3) which possesses the absolutely conserved Cys, His, and Asp residues that form the catalytic triad and a Gln that forms the oxyanion hole in the active site (Gong, L., et al., *J Biol Chem* 275(5): p. 3355-9 (2000)). The variable N-terminal domain is believed to play a regulatory role since expression of the C-terminal catalytic domain alone leads to lower levels of SUMO-1, indicative of constitutive catalytic activity (Bailey, D. and P. O'Hare, *J Biol Chem* 279(1):692-703 (2004)).

TABLE 3

Sequence Similarity/Identity (lower/upper) Matrix for *H. sapiens* SENP and *S. cerevisiae* ULP families. e.g.: SENP1 and SENP2 have 73.71% similarity and 60.3% identity.

|  | senp1_human | senp2_human | senp3_human | senp5_human | senp6_human | senp7_human | senp8_human | ulp2_yeast | 1euv |  |
|---|---|---|---|---|---|---|---|---|---|---|
| senp1_huma |  | 60.31 | 43.62 | 43.62 | 30.21 | 31.41 | 21.79 | 27.03 | 37.57 | 24 gaps |
| senp2_huma | 73.71 |  | 37.23 | 36.17 | 30.73 | 30.37 | 20.11 | 27.57 | 35.84 | 23 gaps |
| senp3_huma | 65.96 | 56.38 |  | 62.18 | 29.79 | 26.74 | 22.29 | 27.07 | 27.75 | 23 gaps |
| senp5_huma | 62.23 | 55.85 | 76.68 |  | 31.91 | 30.11 | 22.29 | 25.56 | 28.32 | 24 gaps |
| senp6_huma | 56.77 | 52.08 | 52.66 | 54.79 |  |  | 57.43 | 24.86 | 29.63 | 29.94 | 14 gaps |
| senp7_huma | 53.93 | 50.26 | 48.13 | 52.15 | 72.28 |  | 22.95 | 29.26 | 31.43 | 17 gaps |
| senp8_huma | 40.22 | 36.87 | 44.00 | 39.43 | 44.32 | 46.45 |  | 21.71 | 21.39 | 18 gaps |
| ulp2_yeast | 50.81 | 45.41 | 51.38 | 46.67 | 54.50 | 50.00 | 40.00 |  | 30.99 | 15 gaps |
| 1euv | 54.34 | 54.91 | 46.24 | 46.82 | 48.02 | 51.43 | 38.73 | 47.95 |  | 19 gaps |

The structure of a complex between yeast Ulp1 and Smt3 has been solved (see, e.g., Mossessova, E. and C. D. Lima, *Mol Cell* 5(5):865-76 (2000)). This structure and the sequence alignments described above were used to generate homology models of human SENP1 and SUMO-1 using Moloc (Gerber, P. R. and K. Muller, *J Comput Aided Mol Des* 9(3):251-68 (1995)). The interactions observed in the active site of the modeled human SENP1 with the SUMO-1 substrate are very similar in the experimental yeast and modeled human structures (see Table 4). There are multiple hydrogen bonds involving the Glu93 and Gln94 residues of SUMO-1, but very little interaction with Thr95. Table 4 also lists the homologous residues in other members of the SENP family and makes a prediction about whether these hydrogen bond interactions with Glu93-Gln94 are preserved. Based on this analysis, very little cross reactivity is predicted for SUMO-1 with other members of the SENP family since two of the four critical hydrogen bonds are missing. Specifically, this analysis indicates that an EQTGG (SEQ ID NO:12) substrate/inhibitor would be highly specific for SENP1 and Ulp1 and would not crossreact with other members of the human sentrin/SUMO-specific protease family. Thus, in some embodiments, the SENP1 antagonists of the invention comprise the sequence EQTGG (SEQ ID NO:12), or mimetics thereof.

TABLE 4

Hydrogen Bond Interactions of homology modeled SENP1/SUMO-1 complex with -EQTGG (SEQ ID NO: 12) partial sequence of substrate/proposed inhibitor.

| SENP1 residue | N467 | K455 | T499 | T495 |
|---|---|---|---|---|
| Interaction details (SENP1res:atom-SUMOres:atom) | N467:Nδ2-E93:Oε1 | K455:Nζ-E93:Oε2 | T499:Oδ1-Q94:Nε2 | T495:Oδ1-Q94:Oε1 |
| SENP2 residue | N412 | G400 | P444 | T440 |
| SENP3 residue | N403 | D391 | D431 | S427 |
| SENP5 residue | N584 | D572 | R612 | S608 |
| SENP6 residue | N683 | E671 | K716 | S712 |
| SENP7 residue | N711 | E699 | K744 | S740 |

TABLE 4-continued

Hydrogen Bond Interactions of homology modeled SENP1/SUMO-1 complex with -EQTGG (SEQ ID NO: 12) partial sequence of substrate/proposed inhibitor.

| SENP8 residue | N28 | S16 | Q60 | P56 |
|---|---|---|---|---|
| Ulp1 residue | N450 | R438 | T477 | S473 |

Bold text indicates that the H-bond interaction is preserved with this residue.

As described above, in view of this information there are several approaches to develop an inhibitor for SENP1. In some embodiments, since the structures are available both for human SUMO-1 (C-terminal domain, NMR (Bayer, P., et al. *J Mol Biol.* 280(2): p. 275-86 (1998)) and for the yeast homolog of the SENP1/SUMO-1 complex (X-ray (Mossessova, E. and C. D. Lima, *Mol Cell* 5(5):865-76 (2000)), one of skill in the art may perform structure-based inhibitor design as well as perform virtual screening of compounds for a predicted inhibitory effect.

In some embodiments, the SENP1 antagonists of the invention comprise an aldehyde. Aldehydes are potent inhibitors of cysteine proteases because they form thiohemiacetals. These stable covalent adducts mimic the transition state. Examples in which aldehydes have been used to elucidate the mechanism of cysteine proteases include papain (Schroder, E., et al., *FEBS Lett,* 315(1):38-42 (1993)) and ubiquitin carboxyl-terminal hydrolase (Pickart, C. M. and I. A. Rose, *J Biol Chem* 261(22):10210-7 (1986)). Reduction of the Smt3 substrate by $NaBH_4$ to the C-terminal aldehyde was used to generate a stable transition state analog for cocrystalization studies with yeast Ulp1 (Mossessova, E. and C. D. Lima, *Mol Cell* 5(5): 865-76 (2000)). Therefore, a Gly-Gly aldehyde could serve as a potent inhibitor of the SENP1 cysteine protease.

The three amino acids upstream to the C-terminal Gly-Gly of SUMO-1 (Glu-Gln-Thr), or a mimetic thereof, may be utilized in an inhibitor since these residues contribute significantly to the specificity of the SENP1/SUMO-1 interaction (Table 4 and Table 5). Although Thr95 does not interact strongly with SENP1, it provides the proper spacing between the scissile peptide bond and Glu93-Gln95 residues.

TABLE 5

Figure 3A:
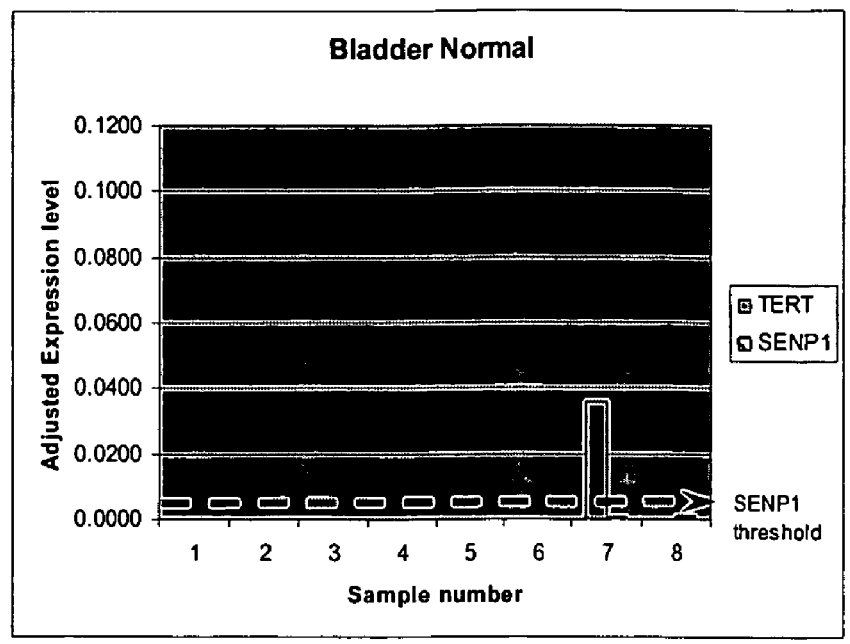
FIGS. 3A and 3B depict the expression level of SENP1 and TERT relative to adjusted GAPDH expression in normal bladder tissue and bladder tumor tissue. For convenience of graphing on the same axis, TERT expression has been multiplied by a factor of $1\times10^5$.
Figure 3B:
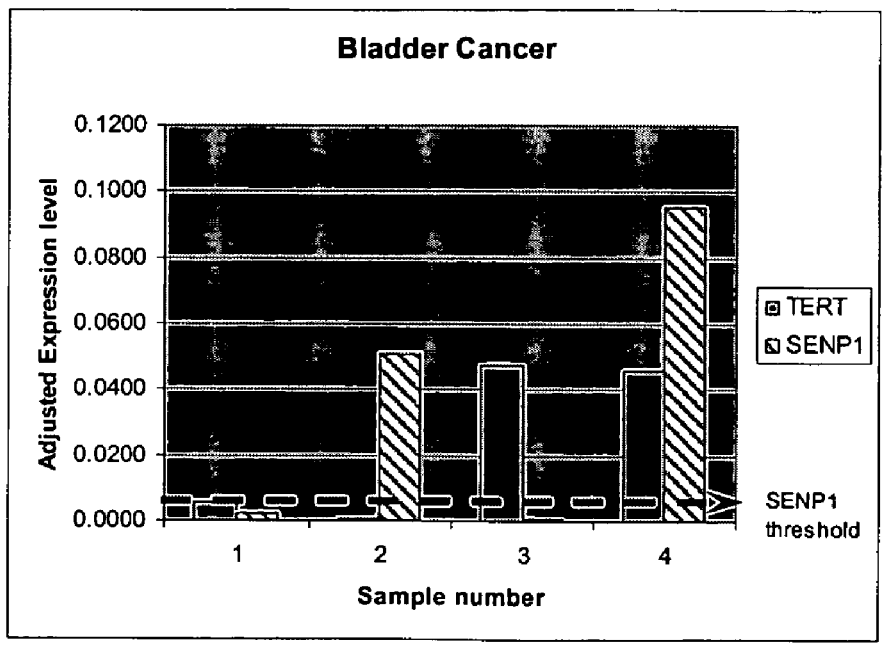
Figure 4A:
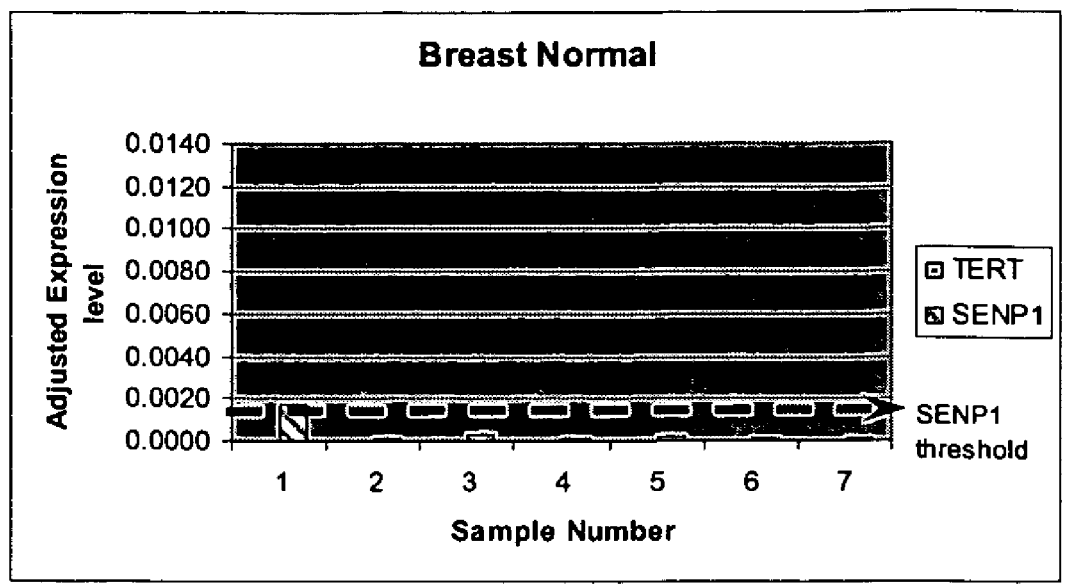
FIGS. 4A and 4B depict the expression level of SENP1 and TERT relative to adjusted GAPDH expression in normal breast tissue and breast tumor tissue. For convenience of graphing on the same axis, TERT expression has been multiplied by a factor of $1\times10^4$.
Figure 4B:
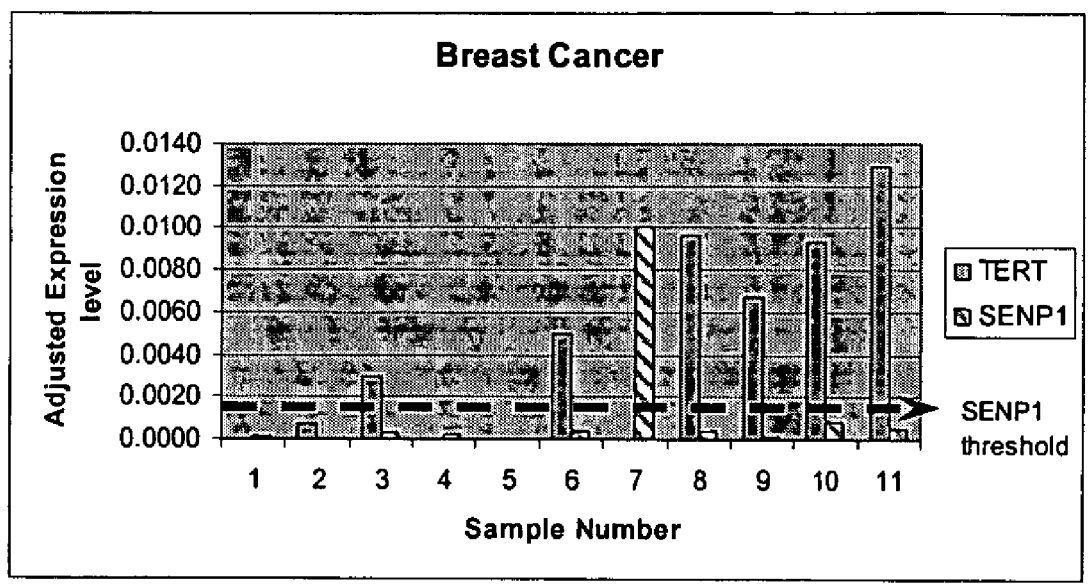
Figure 5A:
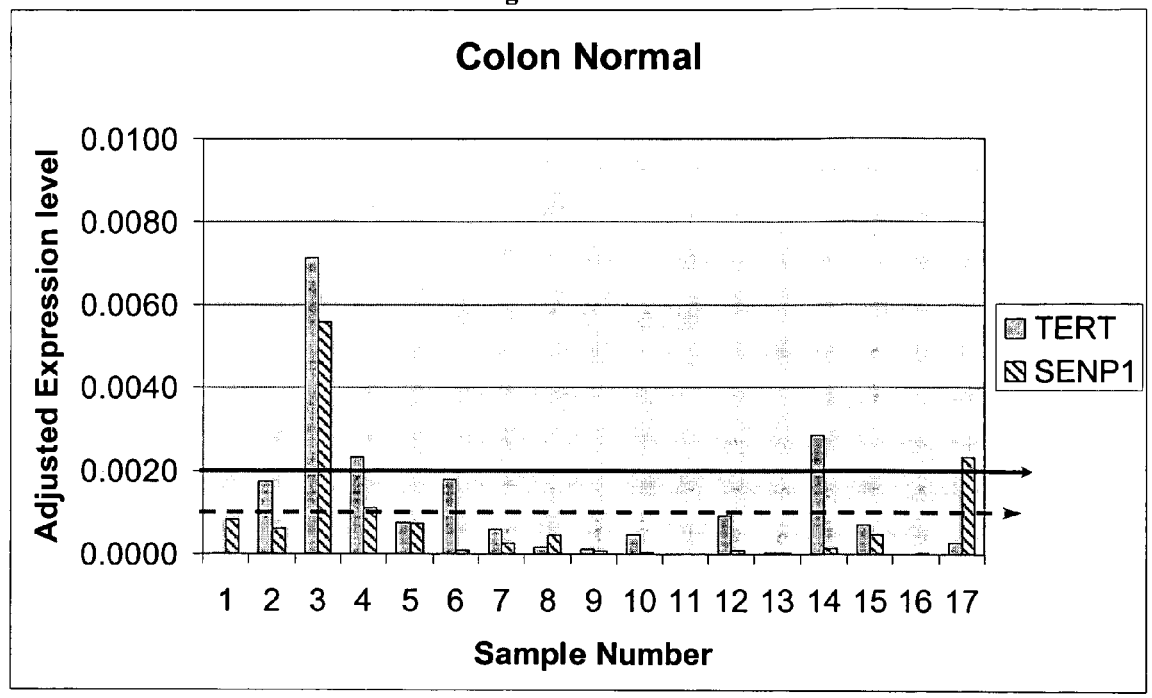
FIGS. 5A and 5B depict the expression level of SENP1 and TERT relative to adjusted GAPDH expression in normal colon tissue and colon tumor tissue. For convenience of graphing on the same axis TERT expression has been multiplied by a factor of $1\times10^3$.
Figure 5B:
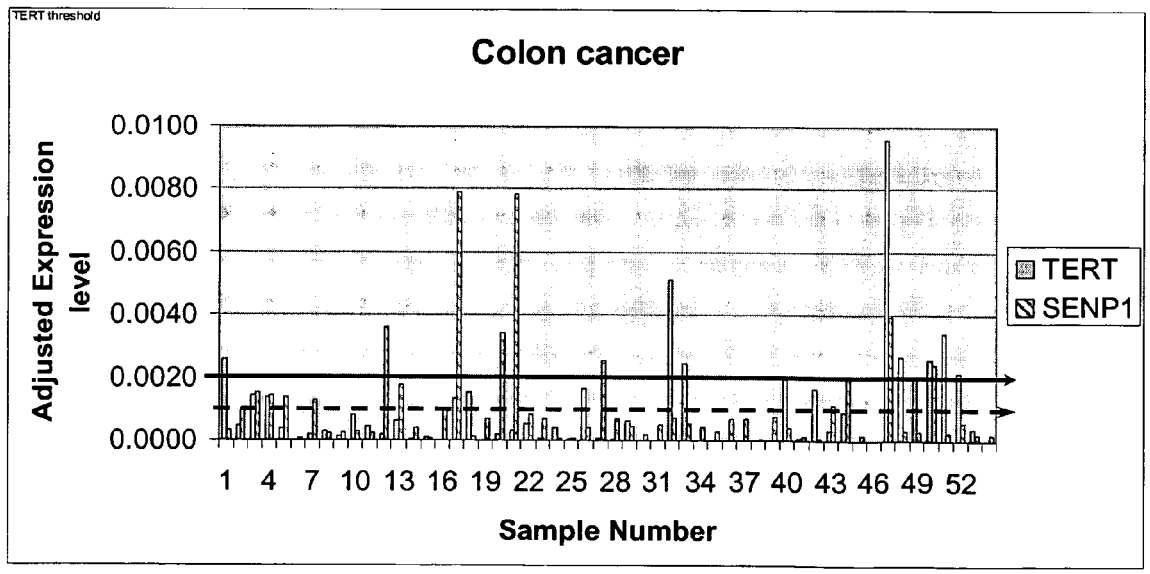
Figure 6A:
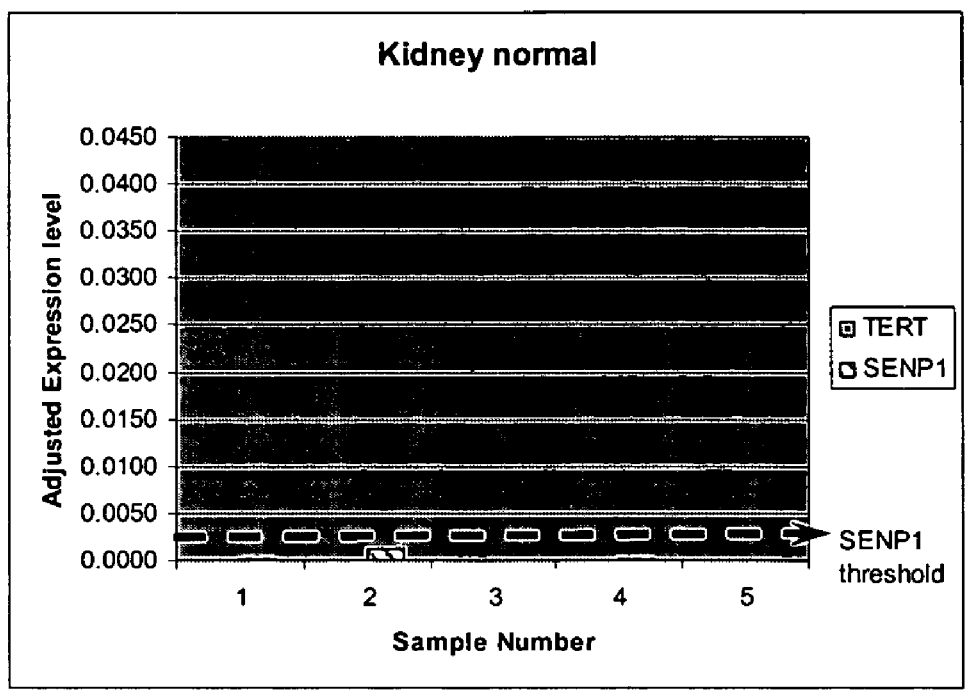
FIGS. 6A and 6B depict the expression level of SENP1 and TERT relative to adjusted GAPDH expression in normal kidney tissue and kidney tumor tissue. For convenience of graphing on the same axis, TERT expression has been multiplied by a factor of $1\times10^4$. Note that sample #3 has a value that falls off the linear scale shown.
Figure 6B:
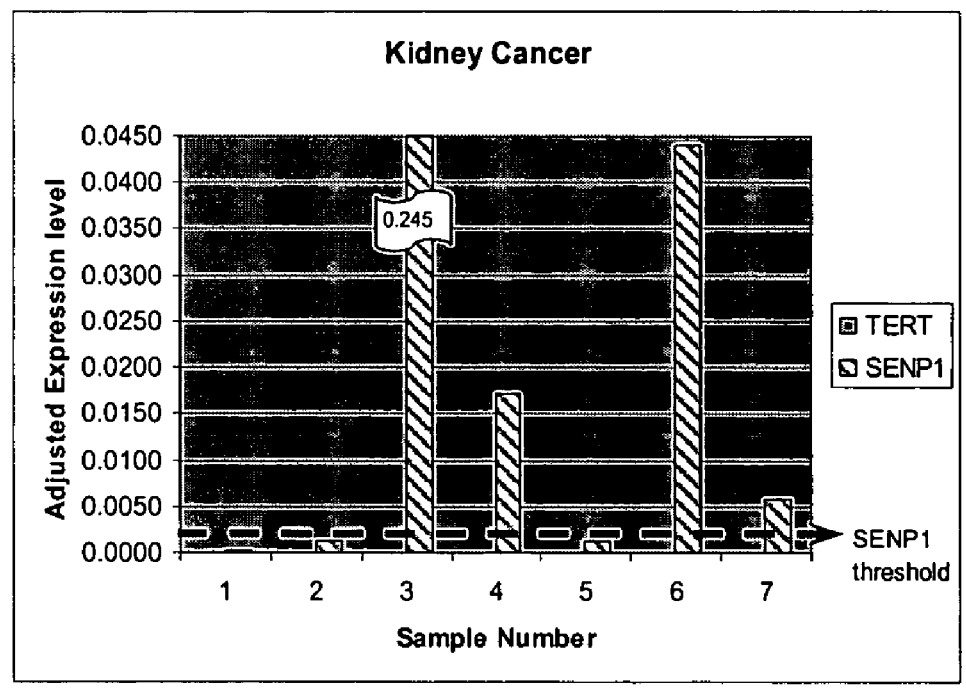
Figure 7A:
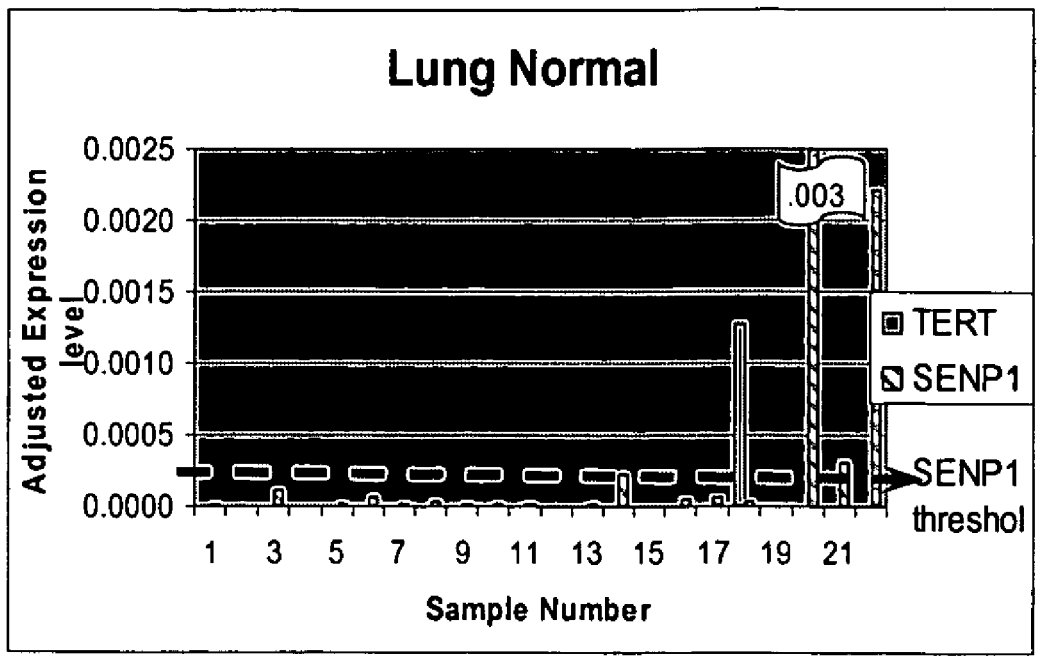
FIGS. 7A and 7B depict the expression level of SENP1 and TERT relative to adjusted GAPDH expression in normal lung tissue and lung tumor tissue. For convenience of graphing on the same axis, TERT expression has been multiplied by a factor of $1\times10^4$. Note that sample #1 and #20 have values that fall off the linear scale as shown.
Figure 7B:
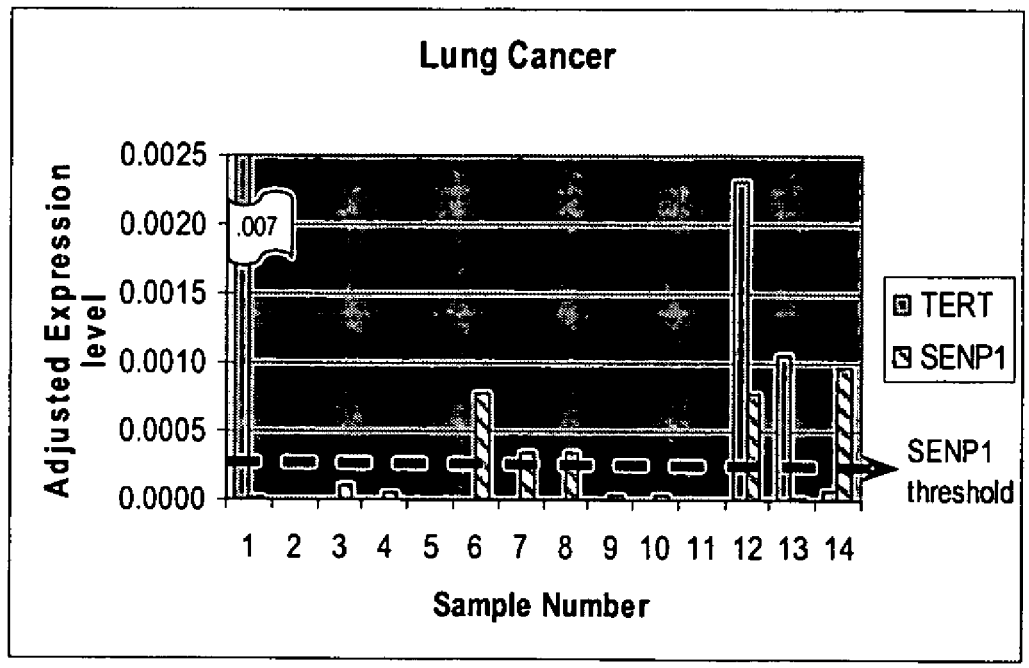
Figure 8A:
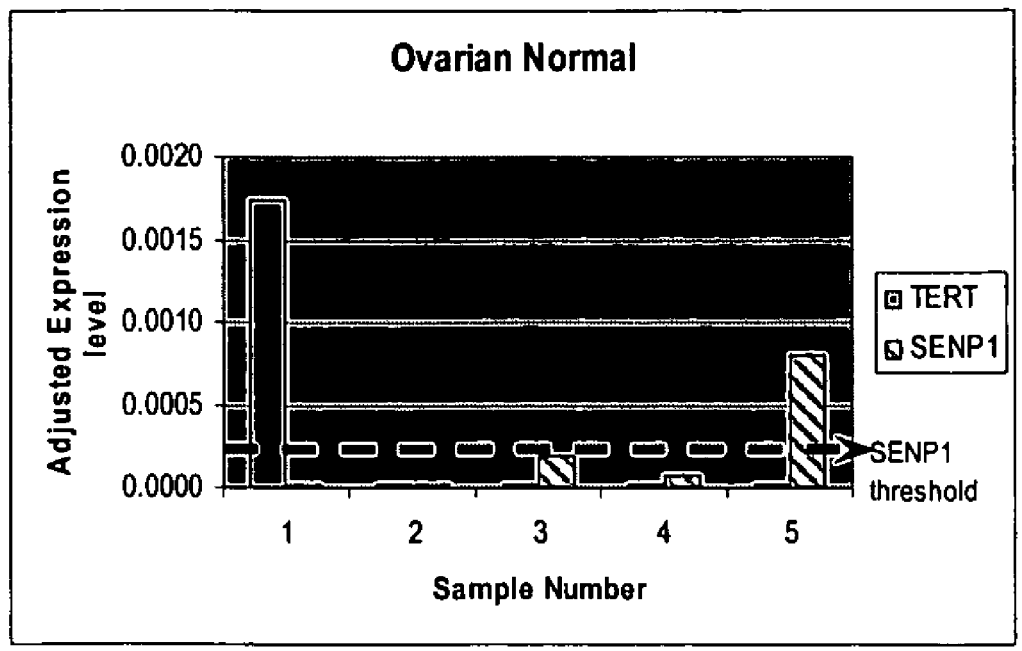
FIGS. 8A and 8B depict the expression level of SENP1 and TERT relative to adjusted GAPDH expression in normal ovarian tissue and ovarian tumor tissue. For convenience of graphing on the same axis, TERT expression has been multiplied by a factor of $1\times10^5$.
Figure 8B:
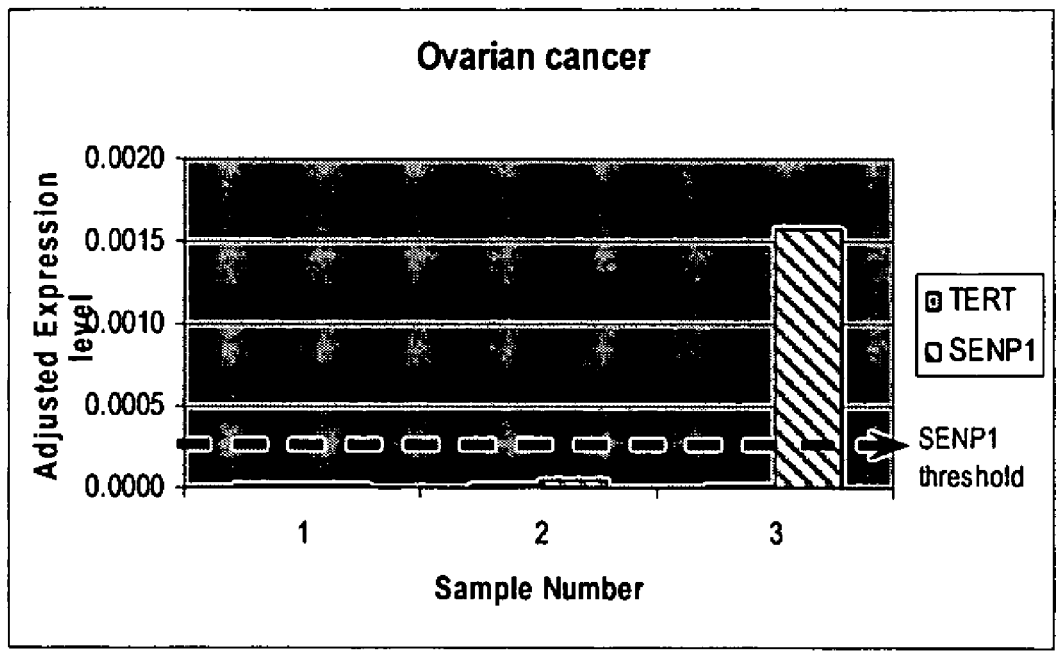
Figure 9A:
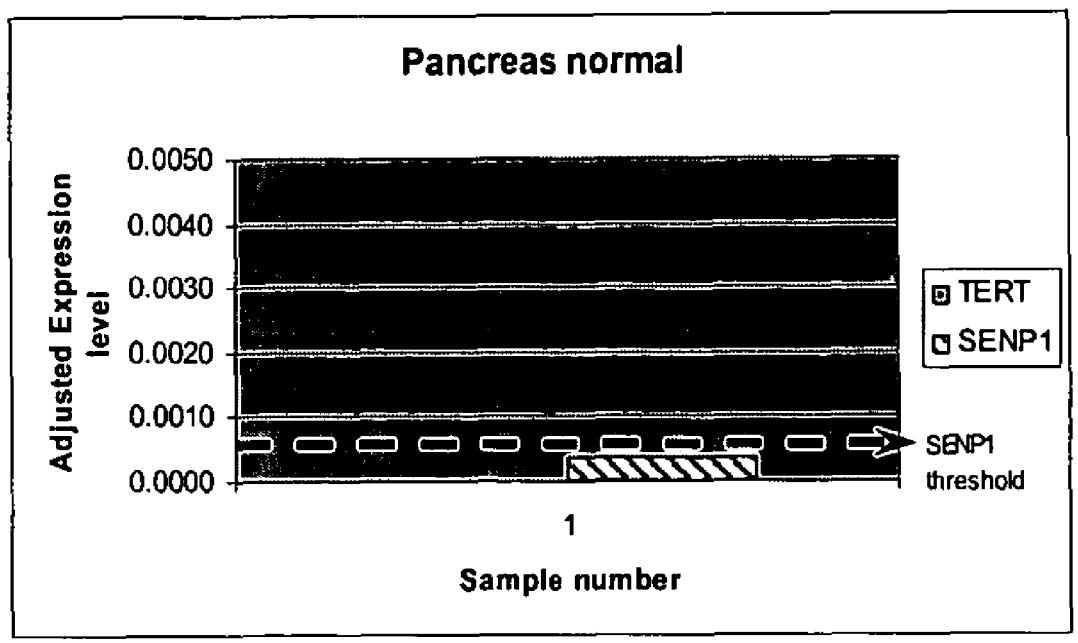
FIGS. 9A and 9B depict the expression level of SENP1 and TERT relative to adjusted GAPDH expression in normal pancreatic tissue and pancreatic tumor tissue. For convenience of graphing on the same axis, TERT expression has been multiplied by a factor of $1\times10^5$.
Figure 9B:
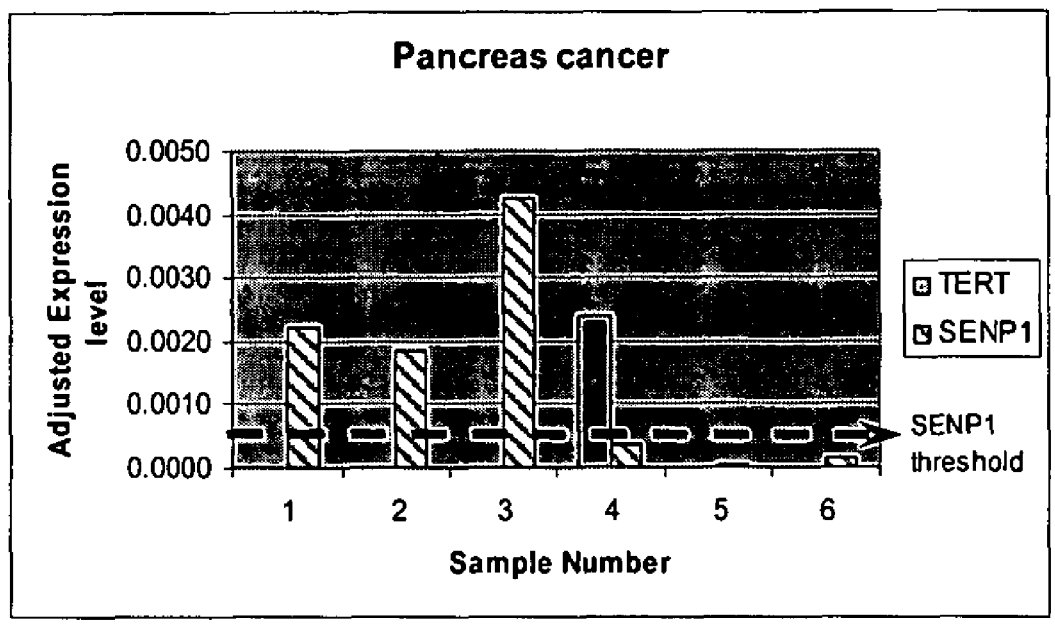
Figure 10A:
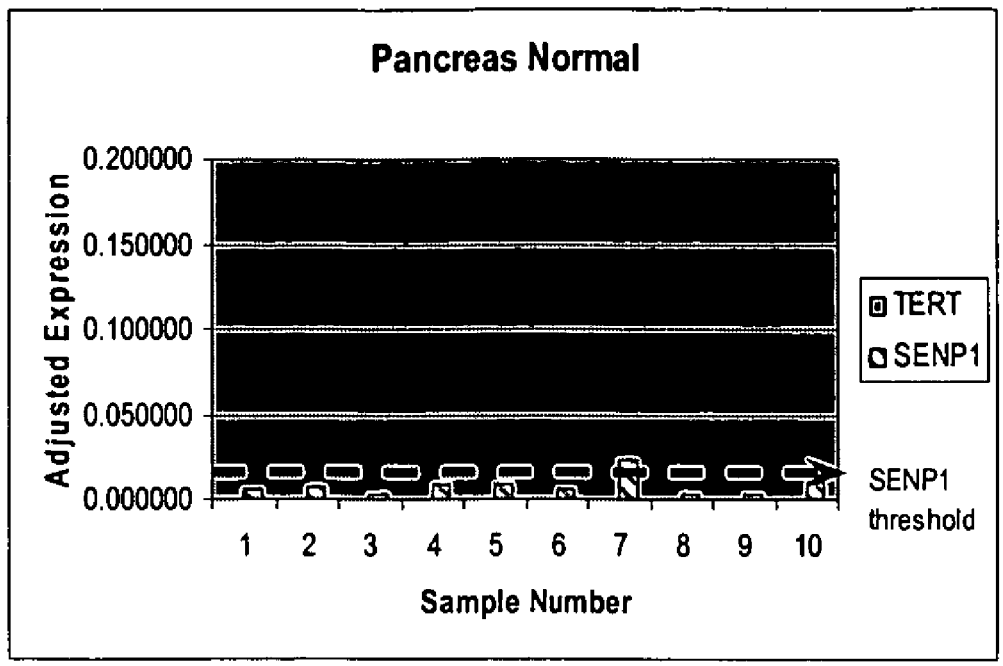
FIGS. 10A and 10B depict the expression level of SENP1 and TERT relative to adjusted GAPDH expression in normal pancreatic tissue (second set) and pancreatic tumor tissue (second set). For convenience of graphing on the same axis TERT expression has been multiplied by a factor of $1\times10^4$.
Figure 10B:
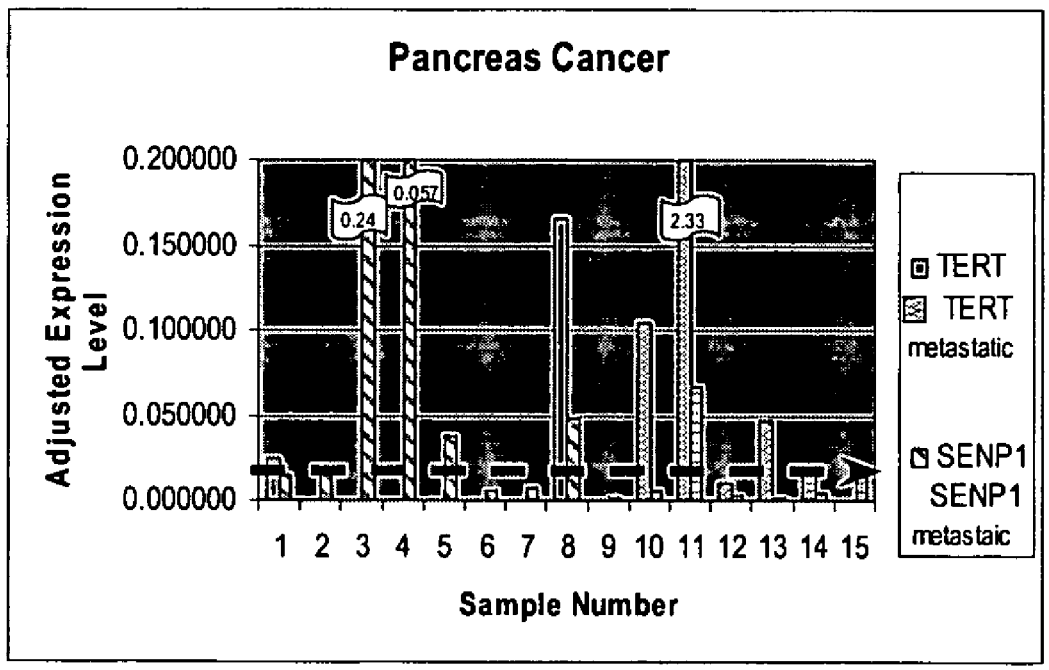
Figure 11A:
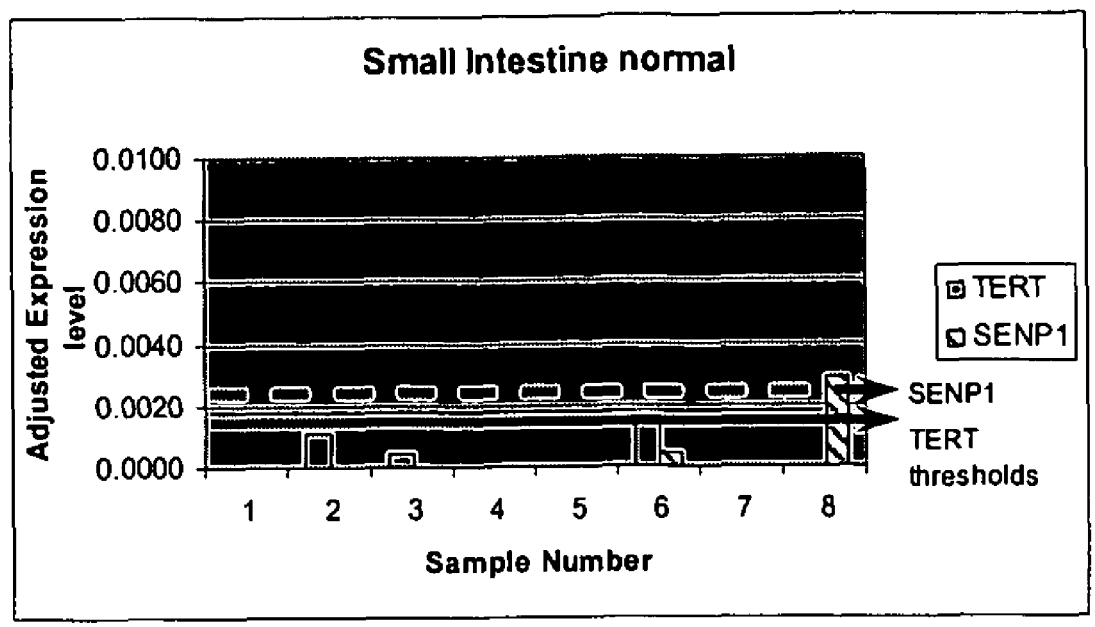
FIGS. 11A and 11B depict the expression level of SENP1 and TERT relative to adjusted GAPDH expression in normal small intestine tissue and small intestine tumor tissue. For convenience of graphing on the same axis TERT expression has been multiplied by a factor of $1\times10^3$.
Figure 11B:
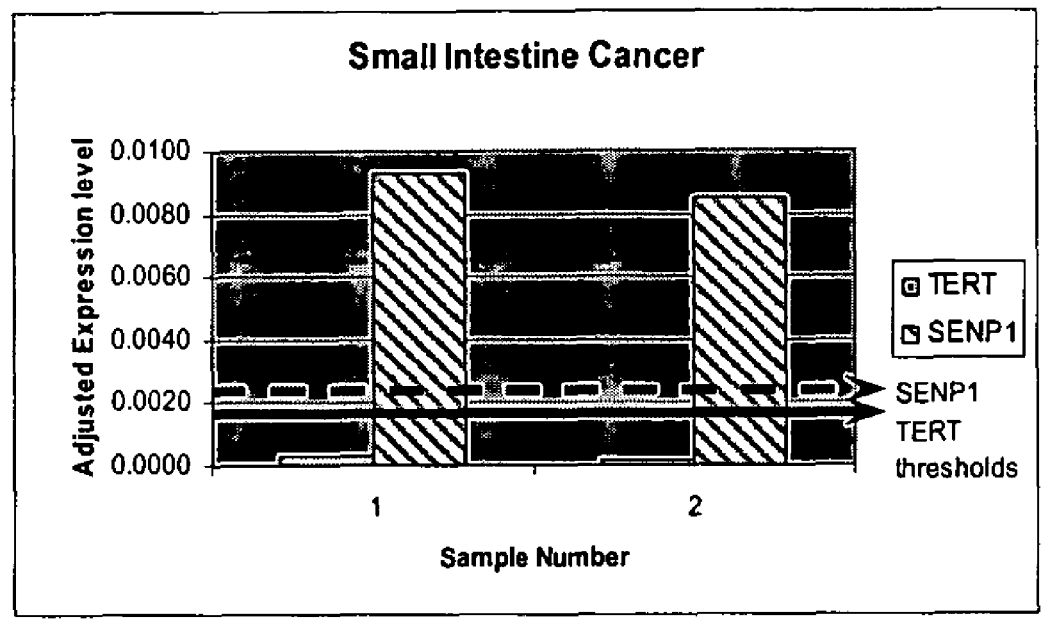

C-terminal sequence of the three SUMO proteins from *H. sapiens* (SEQ ID NOS: 14-17). The sequence corresponding to x1-x3 in FIG. 3 is underlined; the di-Glycine motif is in bold.

| Sm31 | TIDVFQQQTGGVPESSLAGHSF |
|---|---|
| Sm32 | TIDVFQQQTGGVY |

TABLE 5-continued

C-terminal sequence of the three SUMO proteins
from *H. sapiens* (SEQ ID NOS: 14-17). The sequence
corresponding to x1-x3 in FIG. 3 is underlined;
the di-Glycine motif is in bold.

| Sm33 | VIEVYQ<u>EQT</u>GGHSTV |
|------|-----------------------------|
| Smt3 | IIEAHR<u>EQI</u>GGATY |

Although the structure of the SENP1/SUMO-1 complex indicates that the lysine and its flanking residues of the target protein do not interact with SENP1, an alternative inhibitor design could include these amino acids or moieties to mimic their functional groups.

One possible means to validate specificity is to virtually screen for binding of the proposed SENP1 inhibitor to a family of proteins highly related to SENP1 in structure, function and mechanism, such as ubiquitin carboxyl-terminal hydrolases (Pfam motif UCH; PF00443). A search of the Swissprot database reveals three sequences belonging to the UCH family in humans (Table 1). The structure of several UCHs have been solved, including the human UCH-L3 isozyme (Johnston, S. C., et al., *Embo J,* 16(13):3787-96 (1997)) and the yeast enzyme in complex with ubiquitin C-terminal aldehyde (Johnston, S. C., et al., *Embo J.* 18(14): p. 3877-87 (1999)). Homology models for the other family members could be constructed using these X-ray structures as a template. A highly specific inhibitor of SENP1 inhibitor would interact favorably with SENP1, but not with any UCH. Thus, in some embodiments, the screening methods of the invention further comprises selecting an agent that binds and/or inhibits SENP1 but does not inhibit at least one ubiquitin carboxyl-terminal hydrolase.

The nuclear localization of SENP1 plays a role in its substrate specificity. Therefore, in some embodiments, to ensure minimal cross reactivity of the proposed inhibitor with other cysteine proteases, one may utilize SENP1's own nuclear localization sequence (NLS1; PKKTQRR; SEQ ID NO:13) as part of the inhibitor in a Trojan Horse design. This heptapeptide sequence, when modeled onto the SUMO-1 structure of the SENP1-SUMO1 homology modeled complex, shows only one steric overlap involving Inhibitor Arg6' with SENP1 Lys500. However, there would be sufficient space for the heptapeptide to make conformational adjustments in order to avoid such unfavorable steric or charge interactions since the first 92 amino acids of SUMO-1 would be missing. Accordingly, in some cases, an inhibitor of SENP1 comprises one or more of the following: 1) a Gly Gly aldehyde, 2) the Glu-Gln-Thr sequence, or a mimetic thereof, and/or 3) a nuclear localization signal such as PKKTQRR (SEQ ID NO:13).

IX. Pharmaceutical Compositions and Administration

Antagonists of SENP1 can be administered directly to the mammalian subject for treating cancers, including, e.g., bladder cancer, breast cancer, colon cancer, kidney cancer, lung cancer, ovarian cancer, pancreatic cancer, and small intestine cancer. Administration may be by any of the routes normally used for introducing a chemotherapeutic or other anti-cancer drug into ultimate contact with the tissue to be treated. Although more than one route can be used to administer a particular composition, a particular route can often provide a more immediate and more effective reaction than another route. SENP1 antagonists may be administered to an individual either as the sole active ingredient or in combination with chemotherapeutic or other anti-cancer agents.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences,* 17$^{th}$ ed. 1985)).

The SENP1 antagonists, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of antagonists can be presented in unit-dose or multi-dose sealed containers, such as ampoules and vials. Solutions and suspensions can be prepared from sterile powders, granules, and tablets of the kind previously described. The antagonists can also be administered as part a of prepared food or drug.

The dose administered to a patient, in the context of the present invention should be sufficient to effect a beneficial response in the subject over time. The optimal dose level for any patient will depend on a variety of factors including the efficacy of the specific antagonist employed, the age, body weight, physical activity, and diet of the patient, on a possible combination with other drugs, and on the severity of a particular disease. The size of the dose also will be determined by the existence, nature, and extent of any adverse side-effects that accompany the administration of a particular compound or vector in a particular subject.

In determining the effective amount of the antagonist to be administered a physician may evaluate circulating plasma levels of the antagonist, antagonist toxicity, and the production of anti-antagonist antibodies. In general, the dose equivalent of a antagonist is from about 1 ng/kg to 10 mg/kg for a typical subject. Administration can be accomplished via single or divided doses.

EXAMPLES

Example 1

Association of SENP1/Telomerase Expression with Bladder Cancer

Our work shows that an increased level of the sentrin/SUMO-specific protease (SENP1) mRNA is present in the urine sediment of bladder cancer patients, who have tumors that do not express measurable telomerase (TERT) mRNA in the urine sediment. Thus, measurement of SENP1 can be used to diagnose, monitor and assess prognosis of cancers, particularly, though not necessarily exclusively, in cases where TERT is not expressed.

Our current work shows that an increase in expression of SENP1 mRNA is associated with cells from tumors not expressing detectable levels of telomerase mRNA. To the best of our knowledge, this is the first demonstration that SENP1 is elevated in telomerase-negative samples from cancer patients. In this context, SENP1 provides a useful marker in diagnostic, monitoring and prognostic tests for cancer. Also, it is worth noting that the expression of telomerase in tumors does not necessarily preclude the overexpression of SENP1. Therefore, overexpression of SENP1 is a useful marker for detection of some tumors that are telomerase positive.

Urine (100 ml) was obtained from human subjects who were healthy or were diagnosed with bladder cancer. Cells from these samples were collected by low speed centrifugation (700×g for 10 minutes), and rinsed twice with phosphate buffered saline. Cells were lysed in lysis buffer provided in the Roche HighPure total RNA kit. Total RNA was purified using the Roche HighPure total RNA kit. Samples were assayed by quantitative real-time reverse transcription polymerase chain reaction (RT-PCR) for expression of the gene encoding telomerase reverse transcriptase (TERT), and expression of protein phosphatase 1, catalytic subunit, alpha isoform (PPP1CA), a gene used to monitor the yield of RNA from the samples.

For the current study, nineteen telomerase-negative samples from bladder cancer patients and nineteen telomerase-negative samples from healthy subjects were analyzed by quantitative real-time RT-PCR. Experimental conditions were as follows in each assay: 100 µl reactions contained 50 mM bicine, pH 8.0, 115 mM potassium acetate, 8% glycerol, 3 mM manganese acetate, 200 uM each deoxyadenosine triphosphate, deoxycytidine triphospate, deoxyguanosine triphosphate, and 500 uM of deoxyuridine triphosphate, 2 Units of uracil N-glycosylase (UNG) from Applied Biosystems, 10 Units of rTth DNA polymerase (recombinant form of DNA polymerase from *Thermus thermophilus* from Applied Biosystems), 10 nM 5' nuclease probe, 200 nM each primer, forward and reverse. SENP1 RNA was reverse transcribed, amplified and detected with a fluorescently-labeled probe.

Assays were run in the ABI Prism 7700 with cycling conditions as follows: An initial incubation step at 50° C. for 2 minutes to allow UNG-mediated elimination of any contamination by carryover PCR product, denaturation for 1 minute at 95° C., and a reverse transcription step of 30 minutes at 60° C., were followed by 50 cycles of denaturation at 95° C. for 20 seconds and annealing/extension at 60° C. for 40 seconds. It is worth noting that these fixed assay conditions are arbitrary and that the same results could be obtained with a variety of buffers, salts, glycerol/DMSO concentrations, nucleotide concentrations, primer and probe concentrations, reverse transcriptases, DNA polymerase enzymes, two-enzyme/one-tube or two-enzyme/two-tube methods for RT-PCR, with and without UNG, using magnesium or manganese as the divalent cation, various primer/probe concentrations, sequences and thermocycling conditions. Sequences of primers and probes were as follows: For SENP1 CAAGAAGTGCAGCTTATAATCCAA (SEQ ID NO:6; forward "sense" primer) and GTCTTTCGGGTTTCGAGGTAA (SEQ ID NO:7; reverse "antisense" primer), CTCAGACAGTTTTCTTGGCTCAGGCG (SEQ ID NO:8; probe); for PPP1CA GAGCACACCAGGTGGTAGAA (SEQ ID NO:9; forward primer), GGGCTTGAGGATCTGGAAA (SEQ ID NO:10; reverse primer), GAGTTTGACAATGCTGGCGCCATGATGAGT (SEQ ID NO:11; probe).

Levels of SENP1 mRNA were measured by quantitative real-time RT-PCR. Relative copy numbers of SENP1 were determined based on RNA quantification standards. These standards consist of PPP1CA run-off transcripts of known concentrations, reverse transcribed and amplified by PCR under the same conditions as the experimental samples. Cycle threshold (Ct) values were calculated to provide a measure of the amount of mRNA that was present at the beginning of the amplification reaction. Since efficiencies in amplification reactions are rarely, if ever, exactly the same with different primer/probe sets or in standards versus samples from human subjects due to the possible presence of inhibitors of reverse transcription that might carry through the sample preparation in the latter case, copy numbers are stated as relative copies of a given transcript in a sample rather than as an absolute copy number.

As shown in Table I, the median number of copies of SENP1 in healthy subjects is 4, the median in bladder cancer telomerase-negative patients is 1899 copies. The median is calculated rather than the mean in order to mitigate the effect of outliers on calculations. The receiver-operator characteristic curve for these samples (FIG. 1) (as determined according to the methods of A. Agresti, CATEGORICAL DATA ANALYSIS (2002) p. 228-230) shows that the telomerase-negative bladder cancer patients can be distinguished from the telomerase-negative healthy subjects on the basis of SENP1. To a first approximation this subset of patients can be distinguished from one another with a 100% sensitivity and a 90% specificity.

TABLE I

Relative copies of SENP1 mRNA in healthy subjects vs. telomerase negative bladder cancer patients

| | Bladder Cancer Patients-Telomerase Negative SENP1 Copies | Healthy Subjects SENP1 Copies |
|---|---|---|
| | 125 | 0 |
| | 201 | 0 |
| | 240 | 0 |
| | 304 | 0 |
| | 322 | 0 |
| | 655 | 0 |
| | 1184 | 0 |
| | 1413 | 0 |
| | 1499 | 3 |
| | 1899 | 4 |
| | 2708 | 4 |
| | 2873 | 5 |
| | 4113 | 10 |
| | 4610 | 10 |
| | 5188 | 12 |
| | 5839 | 21 |
| | 6195 | 26 |
| | 9941 | 380 |
| | 14173 | 1675 |
| Median | 1899 | 4 |

Figure 2:
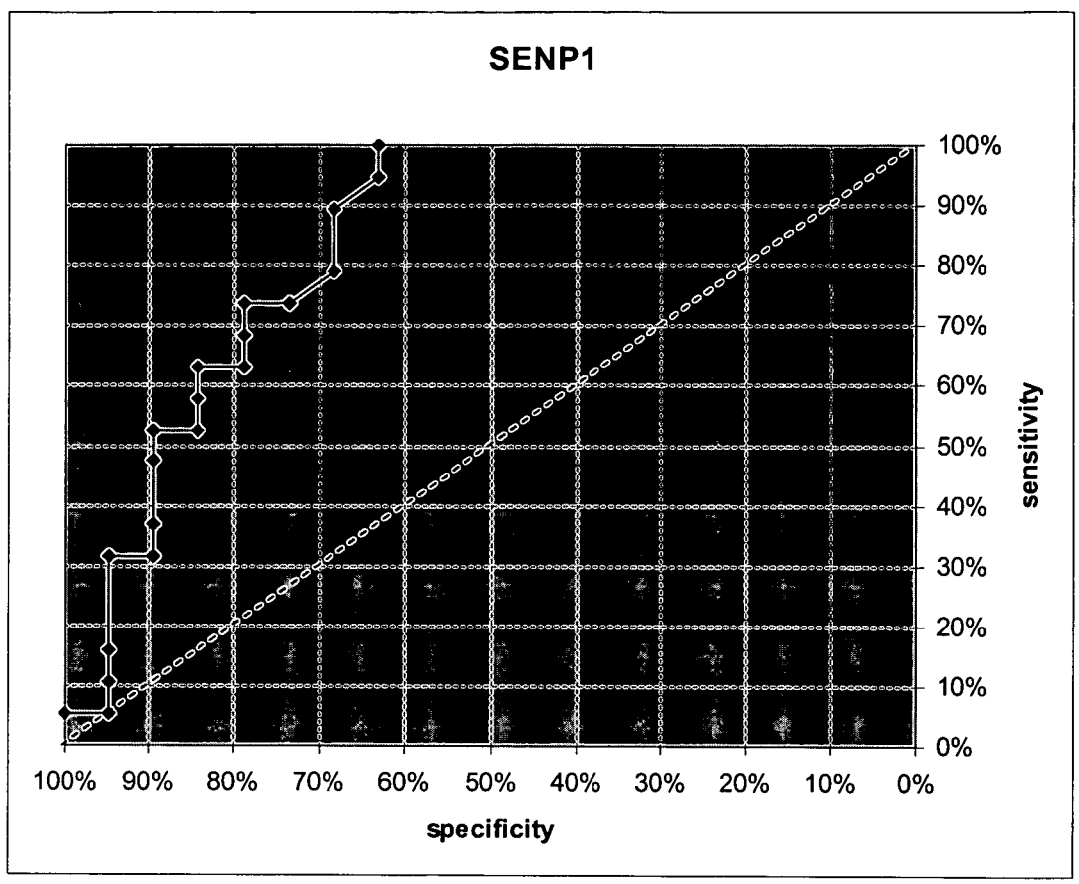
FIG. 2 depicts a receiver-operator curve of SENP1 normalized to the housekeeping gene protein phosphatase 1, catalytic subunit, alpha isoform (PPP1CA).

This data can also be normalized to the level of a housekeeping gene present in each sample. Such normalization controls for variations in the number of cells in the initial sample, an RNA degradation, or the presence of inhibitors in a sample. In this case, the level of PPP1CA previously measured, under the same conditions, was used for normalization. Calculations were as follows: The relative number of copies of SENP1 mRNA in a given sample was divided by the relative number of copies of PPP1CA mRNA in the same sample. For ease of manipulation and recording, this number was multiplied by $1 \times 10^5$. Thus, the normalized copy number for SENP1 mRNA shown in Table II represents the number of copies of SENP1 mRNA per $1 \times 10^5$ copies of PPP1CA mRNA. The median normalized copy number for SENP1 mRNA in healthy subjects is 1096, the median in bladder cancer telomerase-negative patients is 11994. The receiver-operator characteristic curve for these data (FIG. 2) shows that the telomerase-negative bladder cancer patients can be distinguished from the telomerase-negative healthy subjects on the basis of SENP1. To a first approximation this subset of patients can be distinguished from one another with a sensitivity of 90% and a specificity of 70%.

TABLE II

Relative copies of SENP1 mRNA normalized to levels of the housekeeping gene PPP1CA in healthy subjects vs. telomerase negative bladder cancer patients

| Bladder Cancer Patients- Telomerase Negative SENP1 Copies | Healthy Subjects SENP1 Copies |
|---|---|
| 2017 | 0 |
| 2344 | 0 |
| 3242 | 0 |
| 3379 | 0 |
| 3509 | 0 |
| 5095 | 0 |
| 6892 | 0 |
| 8182 | 0 |
| 10413 | 137 |
| 11994 | 1096 |
| 15370 | 1445 |
| 16401 | 1592 |
| 17827 | 2257 |
| 22070 | 3688 |
| 22378 | 4561 |
| 23384 | 7639 |
| 26195 | 10591 |
| 33182 | 19453 |
| 76298 | 47093 |
| Median 11994 | 1096 |

Our results indicate that SENP1 can be used as a marker to differentiate cancer patients from healthy patients on the basis of mRNA found in cells in samples from the patients.

Example 2

Association of SENP1 and/or Telomerase Expression with Breast Cancer, Colon Cancer, Kidney Cancer, Lung Cancer, Ovarian Cancer, Pancreatic Cancer, and Small Intestine Cancer 100 mg of frozen solid tissues were homogenized in 7.5 ml of Ultraspec solution (Biotexc) for 30 seconds. Total RNA was extracted using the Biotecx Ultraspec® RNA kit. RNA was further purified using the QIAGEN RNeasy mini kit. (for a maximum of 100 ug of total RNA), including a QIAGEN DNase treatment.

cDNA was synthesized using 3-50 ug of total RNA per reaction, based on the method described in the Invitrogen Superscript™ Double-Strand cDNA synthesis kit. Reagents were purchased from Invitrogen unless otherwise stated. In the first strand synthesis reaction, the final concentrations of reagents was as follows: 5 pM Poly dT primer (Affymetrix #900375), 1× First Strand Buffer, 0.01M DTT, 0.5 mM each of dATP, dCTP, dGTP and dTTP, 400 Units of SuperScript™ II RNase H-Reverse Transcriptase (SSRT), total reaction volume was 20 µl. First strand primer (1 µl) was incubated with total RNA (plus RNase free water to bring volume to 10 µl) at 70° C. for 10 min., followed by incubation on ice for 2 min. First Strand Buffer, DTT and dNTPs were added followed by incubation at 42° C. for 2 min. After addition of SSRT II samples were incubated for 1 hr at 42° C.

Second strand synthesis was then performed. To the entire 20 µl reaction from first strand synthesis the following reagents were added to the final concentrations indicated: 1× Second Strand buffer, 0.2 mM each of dATP, dCTP, dGTP, and dTTP, 10 U of E. coli DNA Ligase, 40 U of E. Coli DNA Polymerase I, 2 U of RNase H, 20 U of T4 DNA Polymerase, total reaction volume was 150 µl. All reagents except the T4 DNA Polymerase were mixed and incubated for 2 hr at 16° C. T4 DNA Pol was then added followed by a 16° C. incubation for 5 min.

For each sample the entire 150 µl of resulting ds cDNA was purified by use of Phase Lock Gel (available through Brinkmann) as follows: 150 ul of ds cDNA was mixed with an equal volume of phenol-chloroform-isoamyl alcohol. The aqueous phase was transferred to a new tube and the RNA was precipitated by standard methods using ammonium acetate and ethanol, followed by two washes with ice cold 100% ethanol. The pellet was dried and resuspended in 2-10 ul of RNase free deionized water. cDNA was quantitated by measuring the OD260.

Quantitative PCR was run on samples under the following conditions: 7 ng of cDNA, 1× TaqMan® Universal Master Mix (purchased stock available from Applied Biosytems was considered 2×), 2.4 µM each forward and reverse human GAPDH primers, and 0.5 uM human GAPDH TaqMan probe, and the primers and probe for a given gene of interest was added to the same reaction tube at concentrations described for GAPDH primers and probes. Sequences of these primers and probes were: For SENP1, CAAGAAGTG-CAGCTTATAATCCAA (SEQ ID NO:6; forward "sense" primer) and GTCTTTCGGGTTTCGAGGTAA (SEQ ID NO:7; reverse "antisense" primer), CTCAGACAGTTTTCT-TGGCTCAGGCG (SEQ ID NO:8; TaqMan probe); for TERT, TGGGCACGTCCGCA (SEQ ID NO:18; forward), GGCGTGGTGGCACATGAA (SEQ ID NO:19; reverse), TCATCGAGCAGAGCTCCTCCCTGAATGAGG (SEQ ID NO:20; TaqMan probe). All primers and probes, including those for a panel of seven housekeeping genes (see below) were purchased from ABI. Total volume of each assay was 20 µl. Cycling was performed on an ABI Prism®7900 HT Sequence Detection System. An initial incubation of 2 minutes at 50° C. was followed by 10 minutes at 95° C. then 40-55 cycles of 95° C. for 15 sec and 60° C. for 1 min.

Relative expression levels of SENP1 and TERT mRNA (referred to as genes of interest or GOI) were calculated in the following way: Cycle threshold (Ct) values were determined from RT-PCR for SENP1 and TERT, GAPDH and a panel of seven "housekeeping" human genes. The seven genes were hypoxanthine phosphoribosyl transferase, β-glucuronidase, β2-microglobulin, phosphoglyceratekinase, cyclophilin, β-actin, and large ribosomal protein PO. Based on the Cts of the panel of housekeeping genes, the GAPDH Ct was adjusted to give the expected value. This adjustment compensates for any small unexpected differences in the GAPDH Ct that could be explained by GAPDH not behaving as the "average" housekeeping gene in a particular sample. The relative expression level of the GOI is then calculated as:

$Ct(\text{adjusted GAPDH}) - Ct(GOI) = \Delta Ct$ $2^{\Delta\Delta Ct}$=relative expression level of GOI As shown in FIGS. 3 through 11 and in Table III, our current data shows that in a variety of cancers some, but not all, tumors show telomerase (TERT) expression elevated above that in normal cells. Likewise, some tumors, but not all, show an increase in SENP1 expression. Use of both SENP1 and TERT in combination as molecular markers for cancer allows for a greater number of samples from tumor tissue to be identified as cancer positive than use of either marker alone. Thus, a molecular assay in which the up-regulation of either marker was scored as positive for cancer would show an increased sensitivity for cancer detection. This increased sensitivity would, not surprisingly, come at a cost of a somewhat decreased specificity (i.e. an increased number of subjects who did not have cancer would be identified as having cancer). To use an assay for a given diagnostic setting, one would choose standardized values for positive and negative calls that would maximize correct calls, thus maximizing sensitivity and specificity. In the examples shown, threshold values were chosen that, for each individual marker, would give approximately 80% specificity. Unless otherwise shown, the threshold for detection of TERT is zero.

Table III provides a summary of performance of telomerase and senp1 as single markers or as combined markers. Sensitivity is the number of cancer positive samples of a given tissue type that are called cancer positive divided by the total number of cancer positive samples of that tissue type. Specificity is the number of cancer negative (or normal) samples of a given tissue type that are called cancer negative divided by the total number of cancer negative samples of that tissue type. The "accuracy" of a given assay is defined as the sum of its sensitivity and specificity.

TABLE III

| Cancer Type | Telomerase | | | SENP1 | | | Combined | | |
|---|---|---|---|---|---|---|---|---|---|
| | Sensitivity | Specificity | Accuracy | Sensitivity | Specificity | Accuracy | Sensitivity | Specificity | Acccuracy |
| Bladder | 3/4 | 7/8 | 162% | 2/4 | 8/8 | 150% | 4/4 | 7/8 | 187% |
| | 75% | 87% | | 50% | 100% | | 100% | 87% | |
| Breast | 7/11 | 7/7 | 163% | 1/11 | 6/7 | 94% | 8/11 | 6/7 | 157% |
| | 63% | 100% | | 9% | 85% | | 72% | 85% | |
| Colon | 9/54 | 14/17 | 98% | 14/54 | 14/17 | 108% | 21/54 | 13/17 | 114% |
| | 16% | 82% | | 26% | 82% | | 38% | 76% | |
| Kidney | 0/7 | 5/5 | 100% | 4/7 | 5/5 | 157% | 4/7 | 5/5 | 157% |
| | 0% | 100% | | 57% | 100% | | 57% | 100% | |
| Lung | 3/14 | 20/21 | 116% | 5/14 | 17/21 | 116% | 7/14 | 16/21 | 126% |
| | 21% | 95% | | 36% | 80% | | 50% | 76% | |
| Ovarian | 0/3 | 4/5 | 80% | 1/3 | 4/5 | 113% | 1/3 | 3/5 | 93% |
| | 0% | 80% | | 33% | 80% | | 33% | 60% | |
| Pancreatic | 1/6 | 1/1 | 116% | 3/6 | 1/1 | 150% | 4/6 | 1/1 | 166% |
| | 16% | 100% | | 50% | 100% | | 66% | 100% | |
| Pancreatic (2nd set) | 2/9 | 10/10 | 122% | 4/9 | 9/10 | 134% | 5/9 | 9/10 | 146% |
| | 22% | 100% | | 44% | 90% | | 56% | 90% | |
| Pancreatic (metastatic) | 5/6 | 100% | 183% | 1/6 | 90% | 107% | 5/6 | 90% | 173% |
| | 83% | | | 17% | | | 83% | | |
| Small Intestine | 0/2 | 7/8 | 87% | 2/2 | 7/8 | 187% | 2/2 | 7/8 | 187% |
| | 0% | 87% | | 100% | 87% | | 100% | 87% | |
| FOR ALL CANCERS | 30/116 | 75/82 | 117% | 36/116 | 71/82 | 118% | 59/116 | 67/82 | 133% |
| | 26% | 91% | | 31% | 87% | | 51% | 82% | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. (C) A method for detecting SENP1 and telomerase in a biological sample, comprising detecting the quantity of SENP1 and telomerase in a biological sample from an individual, wherein:
   the quantity of SENP1 is detected by detecting an RNA encoding human SENP1 in the sample,
   the quantity of telomerase is detected by detecting an RNA encoding telomerase in the sample;
   the sample is from an individual having or suspected of having bladder cancer, and
   the sample is urine.

2. The method of claim 1, wherein the detecting comprises amplifying the polynucleotide in an amplification reaction to produce an amplification product.

3. The method of claim 2, wherein the amplification reaction comprises at least two different oligonucleotides such that during the amplification reaction the oligonucleotides prime amplification of at least a fragment of SEQ ID NO:1.

4. The method of claim 2, wherein the amplification product of the amplification reaction is detected in a step comprising hybridizing a detectably-labeled oligonucleotide to the product.

5. The method of claim 4, wherein the amplification reaction comprises a template-dependent nucleic acid polymerase with 5'-3' exonuclease activity under conditions that allow the polymerase to fragment the detectably-labeled oligonucleotide.

6. The method of claim 1, wherein the method further comprises comparing the quantity of SENP1 and telomerase in the sample to a SENP1 standard and a telomerase standard, respectively, wherein the SENP1 standard represents SENP1 from urine of healthy subjects without cancer and the telomerase standard represents telomerase quantities from urine of healthy subjects without cancer.

7. The method of claim 1, wherein the telomerase comprises SEQ ID NO:3.

8. The method of claim 1, wherein the RNA is a TERT RNA.

9. The method of claim 1, wherein the RNA is a TERC RNA.

10. The method of claim 1, wherein the SENP1 RNA encodes a protein comprising SEQ ID NO:2.

* * * * *